United States Patent
Zhang et al.

(10) Patent No.: US 12,398,400 B2
(45) Date of Patent: Aug. 26, 2025

(54) HERBICIDE-RESISTANT ACETYL-CoA CARBOXYLASE (ACC) MUTANT AND USE THEREOF

(71) Applicant: SHANDONG SHUNFENG BIOTECHNOLOGY CO., LTD., Jinan (CN)

(72) Inventors: Jinshan Zhang, Jinan (CN); Limei Wang, Jinan (CN)

(73) Assignee: SHANDONG SHUNFENG BIOTECHNOLOGY CO., LTD., Jinan (CN)

( * ) Notice: Subject to any disclaimer, the term of this patent is extended or adjusted under 35 U.S.C. 154(b) by 848 days.

(21) Appl. No.: 17/454,487

(22) Filed: Nov. 11, 2021

(65) Prior Publication Data

US 2022/0145321 A1    May 12, 2022

Related U.S. Application Data

(63) Continuation of application No. PCT/CN2021/119678, filed on Sep. 22, 2021.

(30) Foreign Application Priority Data

Sep. 23, 2020 (CN) .......................... 202011012066.4
Sep. 18, 2021 (CN) .......................... 202111097312.5

(51) Int. Cl.
  *C12N 15/82* (2006.01)
  *C12N 9/00* (2006.01)

(52) U.S. Cl.
  CPC ............ *C12N 15/8274* (2013.01); *C12N 9/93* (2013.01); *C12N 15/8213* (2013.01); *C12Y 604/01002* (2013.01)

(58) Field of Classification Search
  None
  See application file for complete search history.

(56) References Cited

FOREIGN PATENT DOCUMENTS

WO    2019104058 A1    5/2019

OTHER PUBLICATIONS

Li et al (2018 Genome Biology 19:1-9 (Year: 2018).*
Liu et al (2020 Plant Biotechnology Journal 18:1845-1847, published Jan. 2020 (Year: 2020).*
Winston X. Yan, et al., Functionally diverse type V CRISPR-Cas systems, Science, 2018, pp. 1-8.
Patrick Pausch, et al., CRISPR-CasΦ from huge phages is a hypercompact genome editor, Science, 2020, pp. 333-337, 369.

* cited by examiner

*Primary Examiner* — Brent T Page
(74) *Attorney, Agent, or Firm* — Bayramoglu Law Offices LLC

(57) ABSTRACT

A mutant acetyl-CoA carboxylase (ACC) protein, a nucleic acid encoding the mutant ACC protein, and use thereof are provided. Specifically, compared with a parent ACC protein, the mutant ACC protein has mutations at amino acids corresponding to amino acid 1,879 and/or amino acid 2,186 of SEQ ID NO: 1. An ACC-mutated plant shows high herbicide resistance, and thus the present disclosure has very promising application prospects in the cultivation of an herbicide-resistant plant.

8 Claims, 3 Drawing Sheets

Specification includes a Sequence Listing.

I1879V-quizalofop-p

I1879V-fenoxaprop-p-ethyl

C2186R-Quizalofop-p

C2186R-fenoxaprop-p-ethyl

HERBICIDE-RESISTANT ACETYL-CoA CARBOXYLASE (ACC) MUTANT AND USE THEREOF

TECHNICAL FIELD

The present disclosure belongs to the fields of biotechnology and crop genetic breeding, and specifically relates to an acetyl-CoA carboxylase (ACC) mutant protein, a nucleic acid encoding the ACC mutant protein, and a method and use for improving the resistance of a plant to a herbicide.

BACKGROUND

*Oryza sativa* is consumed by two-thirds of the world's population and is the main energy source in the diet of at least half of the two-thirds of the world's population. Rice is a low-cost food that is easily and rapidly prepared, which can be eaten together with various dishes.

The use of an herbicide to control weeds or plants in a crop has become an almost universal practice. As an important part of the modern agricultural production system, herbicides are considered as the most reliable and economical means among farmland weeding techniques. Since 2,4-dichlorophenoxyacetic acid (2,4-D) was first used in the 1940s, the herbicide industry has been developed for more than 60 years, and a large number of selective herbicides have been successfully developed. The research on acetyl-CoA carboxylase (ACC) inhibitors began in the 1970s. ACC herbicides are divided into the following 4 types: aryloxyphenoxypropionates (APPs), cyclohexanedione oximes (CHDs), aryloxyphenyl-cyclohexanediones (APCHDs), and cyclict riketones (CTRs). ACC herbicides can inhibit the synthesis of fatty acids in gramineous plants with high selectivity, can be transduced in plants, and can control annual or perennial gramineous weeds post-emergence. ACC herbicides have the advantages of high efficiency, low toxicity, long application period, safety to subsequent crops, and the like, and thus occupy an important position in the herbicide market.

ACC is an important target of chemical herbicides, which is a biotin-containing enzyme discovered in 1958. ACC catalyzes the carboxylation of acetyl-CoA in an organism to form malonyl-CoA, which provides a substrate for the synthesis of fatty acids and many secondary metabolites. ACC is a key enzyme or a rate-limiting enzyme for the biosynthesis of fatty acids. The carboxylase involves a two-step reversible reaction, including adenosine triphosphate (ATP)-dependent carboxylation of a biotin group on a substrate domain through biotin-carboxylase enzymatic activity, and transfer of carboxyl from biotin by carboxyltransferase to obtain an acetyl-CoA substrate. ACC is a key enzyme for the biosynthesis of fatty acids in a plant, which occurs in chloroplasts and mitochondria. Moreover, ACC also plays a role in the formation of long-chain fatty acids and flavonoids and the malonylation in cytoplasm.

SUMMARY

The present disclosure is intended to provide a mutant ACC protein capable of imparting herbicide resistance to a plant or a polynucleotide encoding the same, and use thereof.

In the present disclosure, ACC refers to acetyl CoA carboxylase.

Mutant ACC

In an aspect, the present disclosure provides a mutant ACC, and compared to an amino acid sequence of a parent ACC, the mutant ACC has mutation at amino acid corresponding to amino acid 1,879 and/or amino acid 2,186 of an amino acid sequence shown in SEQ ID NO: 1.

In an embodiment, the amino acid 1,879 of the parent ACC may be isoleucine (I), and the amino acid 2,186 may be cysteine (C).

In an embodiment, the isoleucine (I) at position 1,879 may be mutated into an amino acid other than isoleucine (I), and the amino acid other than isoleucine (I) may be one or more selected from the group consisting of alanine (A), valine (V), glycine (G), leucine (L), glutamine (Q), phenylalanine (F), tryptophan (W), tyrosine (Y), aspartic acid (D), asparagine (N), glutamic acid (E), lysine (K), methionine (M), serine (S), threonine (T), cysteine (C), proline (P), histidine (H), and arginine (R).

In a preferred embodiment, the isoleucine (I) at position 1,879 may be mutated into valine (V).

In an embodiment, the cysteine (C) at position 2,186 may be mutated into an amino acid other than cysteine (C), and the amino acid other than cysteine (C) may be one or more selected from the group consisting of alanine (A), valine (V), glycine (G), leucine (L), isoleucine (I), phenylalanine (F), tryptophan (W), tyrosine (Y), aspartic acid (D), asparagine (N), lysine (K), glutamine (Q), methionine (M), serine (S), threonine (T), glutamic acid (E), proline (P), histidine (H), and arginine (R).

In a preferred embodiment, the cysteine (C) at position 2,186 may be mutated into arginine (R).

In an embodiment, the mutation may be selected from the group consisting of I1879V, C2186R, and a combination thereof.

In an embodiment, the parent ACC may be derived from any plant.

In an embodiment, the parent ACC may be derived from one or more selected from the group consisting of a gramineous plant, a leguminous plant, a chenopodiaceous plant, and a cruciferous plant.

In an embodiment, the parent ACC may be derived from one or more selected from the group consisting of *Arabidopsis thaliana* (*A. thaliana*), *Oryza sativa*, *Nicotiana tabacum*, *Zea mays*, *Sorghum bicolor*, *Hordeum vulgare*, *Triticum aestivum*, *Setaria italica*, *Glycine max*, *Lycopersicon esculentum*, *Solanum tuberosum*, *Chenopodium quinoa*, *Lactuca sativa*, *Brassica napus*, *Brassica pekinensis*, and *Fragaria ananassa*.

In a preferred embodiment, the parent ACC of the present disclosure may be derived from *Oryza* L., especially *Oryza sativa*.

In an embodiment, the parent ACC may have ACC activity, and an amino acid sequence of the parent ACC may have at least 80%, at least 85%, at least 90%, at least 95%, at least 96%, at least 97%, at least 98%, or at least 99% sequence identity with the amino acid sequence shown in SEQ ID NO: 1.

In a preferred embodiment, the amino acid sequence of the parent ACC may have the sequence shown in SEQ ID NO: 1, or the amino acid sequence of the parent ACC may be shown in SEQ ID NO: 1.

In an embodiment, the mutant ACC may have at least 60%, preferably at least 70%, preferably at least 80%, and preferably at least 90% (such as 95%, 97%, or 99%) homology with a sequence shown in any one of SEQ ID NOs.: 2-4.

In an embodiment, the mutant ACC may be a polypeptide with an amino acid sequence shown in any one of SEQ ID NOs.: 2-4, an active fragment thereof, or a conservative variant polypeptide thereof.

In an embodiment, the mutant ACC may have an amino acid sequence shown in any one of SEQ ID NOs.: 2-4.

Fusion Protein

In another aspect, the present disclosure provides a fusion protein including the mutant ACC protein of the present disclosure. Further, the fusion protein may also include: a tag peptide, such as a histidine tag or 6×His; a plastid-targeted peptide, such as a chloroplast-targeted peptide; or a regulatory element, such as a promoter sequence, a terminator sequence, a leader sequence, a polyadenylation sequence, or a marker gene.

Polynucleotide

In another aspect, the present disclosure provides a polynucleotide encoding the mutant ACC protein or an active fragment thereof.

In an embodiment, the polynucleotide may be selected from the group consisting of:

(a) a polynucleotide encoding a protein shown in any one of SEQ ID NOs.: 2-4;

(b) a polynucleotide with a sequence shown in any one of SEQ ID NOs.: 5-7;

(c) a polynucleotide that has a nucleotide sequence of homology ≥80% (preferably ≥90%, more preferably ≥95%, and most preferably ≥98%) with a sequence shown in SEQ ID NO: 5 and encodes a protein shown in SEQ ID NO: 2; or, a polynucleotide that has a nucleotide sequence of homology ≥80% (preferably ≥90%, more preferably ≥95%, and most preferably ≥98%) with a sequence shown in SEQ ID NO: 6 and encodes a protein shown in SEQ ID NO: 3; or, a polynucleotide that has a nucleotide sequence of homology ≥80% (preferably ≥90%, more preferably ≥95%, and most preferably ≥98%) with a sequence shown in SEQ ID NO: 7 and encodes a protein shown in SEQ ID NO: 4; and (d) a polynucleotide complementary to any one selected from the group consisting of the polynucleotides described in (a) to (c).

In an embodiment, the polynucleotide may be selected from the group consisting of a genomic sequence, a cDNA sequence, an RNA sequence, and a combination thereof.

In an embodiment, the polynucleotide may preferably be single-stranded or double-stranded.

In an embodiment, the polynucleotide may make an auxiliary element selected from the group consisting of a signal peptide, a secretory peptide, a tag sequence (such as 6His), a nuclear localization signal (NLS), and a combination thereof additionally included at a flank of an open reading frame (ORF) of the mutant protein.

In an embodiment, the polynucleotide may further include a promoter operably linked to the ORF sequence of the mutant polypeptide.

In an embodiment, the promoter may be selected from the group consisting of a constitutive promoter, a tissue-specific promoter, an inducible promoter, and a strong promoter.

Nucleic Acid Construct

In another aspect, the present disclosure provides a nucleic acid construct, including the polynucleotide and a regulatory element operably linked thereto.

In an embodiment, the regulatory element may be one or more selected from the group consisting of an enhancer, a transposon, a promoter, a terminator, a leader sequence, a polyadenylate sequence, and a marker gene.

Vector

The present disclosure also provides a vector including a nucleic acid sequence encoding the mutant ACC or the fusion protein of the present disclosure. Preferably, the vector may further include an expression regulation element operably linked to the aforementioned nucleic acid sequence.

In an embodiment, the vector may include a cloning vector, an expression vector, a shuttle vector, and an integration vector.

In an embodiment, the vector may be a vector for gene editing of the endogenous ACC gene in a host cell.

In an embodiment, the vector may include a polynucleotide encoding a polypeptide shown in any one of SEQ ID NOs.: 2-4.

In an embodiment, the expression vector may also include at least one replication origin to realize self-replication.

In an embodiment, the vector may be a vector that will be integrated into a genome of a host cell when introduced into the host cell and then replicates together with a chromosome into which the vector is integrated.

The vector can be, for example, a plasmid, a virus, a cosmid, a phage, and the like, which are well known to those skilled in the art.

Preferably, the vector in the present disclosure may be a plasmid.

Edit Vector System

In another aspect, the present disclosure provides an edit vector system that can produce the above-mentioned mutant ACC in a plant. The edit vector system may include one or more vectors, and the one or more vectors may at least include a guide sequence targeting the parent ACC.

The guide sequence may include a part of the nucleotide sequence of the parent ACC, preferably at least 15 bp of the ACC nucleotide sequence and more preferably at least 20 bp of the ACC nucleotide sequence. In an embodiment, the edit vector may further include a gene editing enzyme. The gene editing enzyme may include nucleases suitable for CRISPR, transcription activator-like (TAL) effector nuclease (TALEN), zinc-finger nuclease (ZFN), and other editing tools.

Preferably, the gene editing enzyme may be a Cas protein, also known as a CRISPR enzyme or a Cas effector protein, including but not limited to: a Cas9 protein, a Cas12 protein, a Cas13 protein, a Cas14 protein, a Csm1 protein, and an FDK1 protein.

Preferably, the Cas protein may be operably linked to a first regulatory element.

In an embodiment, the gene editing enzyme may be a Cas9 protein, and the vector may further include a Scaffold sequence that can specifically bind to the Cas9 protein. The Scaffold sequence and the guide sequence are operably linked to form a gRNA. Preferably, the gRNA may be operably linked to a second regulatory element.

In other embodiments, the gene editing enzyme may be a Cas12 protein, such as Cas12a, Cas12b, and Cas12i, and the vector may further include a direct repeat that specifically binds to the Cas12 protein. The direct repeat and the guide sequence are operably linked to form a gRNA. Preferably, the gRNA may be operably linked to the second regulatory element.

The above-mentioned regulatory elements may include a promoter, a terminator sequence, a leader sequence, a polyadenylation sequence, a signal peptide coding region, a marker gene, an enhancer, an internal ribosome entry site (IRES), and other expression control elements (for example, a transcriptional termination signal, such as a polyadenylation signal and a poly-U sequence).

Preferably, the edit vector system may further include a base editing element, which is adenine deaminase and/or cytosine deaminase.

In an embodiment, the edit vector may also include a resistance gene to facilitate screening; and the resistance gene may include hyg, bar, kana, rif, spec, and amp, which are well known to those skilled in the art.

Preferably, the guide sequence of gRNA may be A-ACC1879: GAGAATATACATGGAAGTGC; A-ACC2186: ATAGCACTCAATGCGGTCTG; or a combination thereof.

Preferably, the Cas protein may be nCas9 or another Cas9 protein with nick activity. The "n" stands for nick, that is, the "n" indicates a Cas protein with only single-strand cleavage activity.

Host Cell

In another aspect, the present disclosure provides a host cell, where the host cell includes one or more selected from the group consisting of the mutant ACC, the gene encoding the mutant ACC, the fusion protein, the vector, and the nucleic acid construct; or, the polynucleotide is integrated into a genome of the host cell.

In an embodiment, the host cell may be a prokaryotic cell, such as *Escherichia coli* (*E. coli*).

In an embodiment, the host cell may be a plant cell, and the plant may include an angiosperm and a gymnosperm.

In an embodiment, the plant may include a monocotyledonous plant and a dicotyledonous plant.

In an embodiment, the plant may include an herbaceous plant and a woody plant.

In an embodiment, the plant may include *A. thaliana, Nicotiana tabacum, Oryza sativa, Zea mays, Sorghum bicolor, Hordeum vulgare, Triticum aestivum, Setaria italica, Glycine max, Lycopersicon esculentum, Solanum tuberosum, Chenopodium quinoa, Lactuca sativa, Brassica napus, Brassica pekinensis,* and *Fragaria ananassa.*

Resistant Plant

In another aspect, the present disclosure provides an herbicide-resistant plant, where the herbicide-resistant plant includes one or more selected from the group consisting of the mutant ACC, the polynucleotide encoding the mutant ACC, the fusion protein, the vector, and the nucleic acid construct; or, the polynucleotide is integrated into a genome of the plant.

The term "substantially identical" means that two amino acid sequences have 85%, 90%, 95%, 96%, 97%, 98%, or 99% identify.

Method for Preparing the Mutant Polypeptide

In another aspect, the present disclosure provides a method for preparing the mutant ACC polypeptide or an active fragment thereof, including the following step:

(a) under conditions suitable for expression, cultivating a host cell including the mutant ACC polypeptide to express the mutant ACC polypeptide; and preferably, the method may further include:

(b) isolating the mutant ACC polypeptide.

Method for Acquiring the Herbicide-Resistant Plant

In another aspect, the present disclosure provides a plant cell, a plant seed, a plant tissue, a plant part, or a plant with herbicide resistance, where the plant cell, the plant tissue, the plant seed, the plant part, or the plant includes the mutant ACC polypeptide or a polynucleotide sequence encoding the same.

In another aspect, the present disclosure provides a method for acquiring or preparing a plant cell, a plant seed, a plant tissue, a plant part, or a plant with herbicide resistance, including: introducing the mutant ACC polypeptide or a polynucleotide sequence encoding the same into the plant cell, the plant seed, the plant tissue, the plant part, or the plant.

In an embodiment, the introducing the ACC mutant polypeptide of the present disclosure may include the following step: allowing the ACC mutant polypeptide to express in the plant cell, the plant seed, the plant tissue, the plant part, or the plant. For example, the mutant polypeptide is expressed by an expression vector, or the mutant polypeptide is integrated into a plant genome for expression.

In a preferred embodiment, the above method may include the following steps:

(1) providing *Agrobacterium tumefaciens* (*A. tumefaciens*) carrying an expression vector, where the expression vector includes a DNA coding sequence of the mutant ACC polypeptide or an active fragment thereof;

(2) contacting the plant cell, the plant tissue, or the plant part with the *A. tumefaciens* in step (1), such that the DNA coding sequence of the mutant ACC polypeptide or the active fragment thereof is transformed into the plant cell and integrated on a chromosome of the plant cell; and (3) screening out a plant cell transformed with the DNA coding sequence of the mutant ACC polypeptide or the active fragment thereof.

In an embodiment, the introducing the mutant ACC polypeptide may include the following step: allowing endogenous ACC of the plant to mutate to introduce the mutant polypeptide. Preferably, the mutant polypeptide may be introduced by gene editing.

In another preferred embodiment, the method may include: allowing an endogenous ACC coding sequence in the plant cell, the plant seed, the plant tissue, or the plant part to mutate at positions corresponding to amino acid 1,879 and/or amino acid 2,186 of SEQ ID NO: 1.

In another preferred embodiment, the method may include following steps:

(1) introducing the aforementioned edit vector system into the plant cell, the plant seed, the plant tissue, or the plant part; and (2) allowing a gene editing tool to act on an endogenous ACC coding sequence, such that the endogenous ACC coding sequence mutates at positions corresponding to amino acid 1,879 and/or amino acid 2,186 of the amino acid sequence shown in SEQ ID NO: 1.

Further, the above method may also include the following step: screening a mutant plant cell, plant tissue, or plant part, and optionally, isolating the gene editing tool.

In another preferred embodiment, the gene editing tool may include CRISPR, TALEN, and ZFN.

In another preferred embodiment, the plant may include an angiosperm and a gymnosperm.

In another preferred embodiment, the plant may include a monocotyledonous plant and a dicotyledonous plant.

In another preferred embodiment, the plant may include an herbaceous plant and a woody plant.

In another preferred embodiment, the plant may include *A. thaliana, Nicotiana tabacum, Oryza sativa, Zea mays, Sorghum bicolor, Hordeum vulgare, Triticum aestivum, Setaria italica, Glycine max, Lycopersicon esculentum, Solanum tuberosum, Chenopodium quinoa, Lactuca sativa, Brassica napus, Brassica pekinensis,* and *Fragaria ananassa.*

In an embodiment, compared with the maximum tolerated herbicide concentration of the parent plant, the maximum tolerated herbicide concentration of the plant with the mutant polypeptide may be increased by at least 1 to 4 times, such as 2, 3, or 4 times. When an herbicide is applied, the plant with the mutant polypeptide of the present disclosure can tolerate the herbicide at a concentration least 2 to 4 times a recommended concentration of the herbicide, while the parent plant cannot tolerate the herbicide at this concentration.

Method for Controlling Weeds

In another aspect, the present disclosure also provides a method for controlling the growth of weeds near a plant, including:

a) providing the above-mentioned herbicide-resistant plant; and b) applying an effective amount of the herbicide to the plant and weeds nearby to control the weeds.

The plant may preferably be *Oryza sativa*.

The herbicide may include one or more selected from the group consisting of APP, CHD, APCHD, and CTR. Preferably, the herbicide may include one or more selected from the group consisting of alloxydim, butroxydim, clethodim, cyclohexenone, cycloxydim, sethoxydim, tepraloxydim, tralkoxydim, phenthodim, chloroazifop-propynyl, clodinafop-propargyl, clofop, diclofop-methyl, fenoxaprop-ethyl, fenoxaprop-p-ethyl, fenthiaprop-ethyl, fluazifop-butyl, fluazifop-p-butyl, haloxyfop-methyl, haloxyfop-p-methyl, clomazone, clefoxidim, propaquizafop, quizalofop, quizalofop-p, quizalofop-p-ethyl, quizalofop-p-tefuryl, trifluorophenoxy propionic acid, fenoxaprop, and a salt or ester thereof.

Preferably, the herbicide may be one or more selected from the group consisting of sethoxydim, phenthodim, and clethodim.

Use

In another aspect, the present disclosure provides use of the mutant ACC, the gene encoding the mutant ACC, the fusion protein, the vector, or the nucleic acid construct in a reagent or a kit for preparing an herbicide-resistant plant.

In another aspect, the present disclosure provides use of the mutant ACC, the gene encoding the mutant ACC, the fusion protein, the vector, or the nucleic acid construct for controlling weeds.

In another aspect, the present disclosure provides use of the mutant ACC, the gene encoding the mutant ACC, the fusion protein, the vector, or the nucleic acid construct in the preparation of an herbicide-resistant plant.

Herbicide

In an embodiment, the herbicide of the present disclosure may be an ACC-inhibiting herbicide, and the ACC-inhibiting herbicide includes, but is not limited to, one or more selected from the group consisting of APP, CHD, APCHD, and CTR.

Preferably, the herbicide of the present disclosure includes, but is not limited to, one or more selected from the group consisting of alloxydim, butroxydim, clethodim, cyclohexenone, cycloxydim, sethoxydim, tepraloxydim, tralkoxydim, phenthodim, chloroazifop-propynyl, clodinafop-propargyl, clofop, diclofop-methyl, fenoxaprop-ethyl, fenoxaprop-p-ethyl, fenthiaprop-ethyl, fluazifop-butyl, fluazifop-p-butyl, haloxyfop-methyl, haloxyfop-p-methyl, clomazone, clefoxidim, propaquizafop, quizalofop, quizalofop-p, quizalofop-p-ethyl, quizalofop-p-tefuryl, trifluorophenoxy propionic acid, fenoxaprop, and a salt or ester thereof. Preferably, the herbicide may be one or more selected from the group consisting of phenthodim, sethoxydim, and clethodim.

General Definitions

Unless defined otherwise, the technical and scientific terms used herein have the same meanings as commonly understood by one of ordinary skill in the art.

The terms "polynucleotide", "nucleotide sequence", "nucleic acid sequence", "nucleic acid molecule", and "nucleic acid" may be used interchangeably and include DNA, RNA, or a hybrid thereof, which may be double-stranded or single-stranded.

The term "homology" or "identity" used refers to sequence matching between two polypeptides or between two nucleic acids. Therefore, the composition and method of the present disclosure also include homologues of the nucleotide sequence and the polypeptide sequence (such as SEQ ID NOs: 1-7) of the present disclosure. "Homology" can be calculated by a known method including but not limited to: Computational Molecular Biology (edited by Lesk, A. M.), Oxford University Press, New York (1988); Biocomputing: Informatics and Genome Projects (edited by Smith, D. W.), Academic Press, New York (1993); Computer Analysis of Sequence Data, Part I (edited by Griffin, A. M. and Griffin, H. G.), Humana Press, New Jersey (1994); Sequence Analysis in Molecular Biology (edited by von Heinje, G.), Academic Press (1987); and Sequence Analysis Primer (edited by Gribskov, M. and Devereux, J.), Stockton Press, New York (1991).

A specific amino acid position (number) in the protein of the present disclosure is determined by aligning an amino acid sequence of the target protein with SEQ ID NO: 1 using a standard sequence alignment tool. For example, the Smith-Waterman algorithm or CLUSTALW2 algorithm is used to align two sequences, and the sequences are considered aligned when an alignment score is the highest. The alignment score can be calculated according to the method described in Wilbur, W. J. and Lipman, D. J. (1983) Rapid similarity searches of nucleic acid and protein data banks. Proc. Natl. Acad. Sci. USA, 80: 726-730. In the ClustalW2 (1.82) algorithm, default parameters may be preferably used: protein gap opening penalty=10.0; protein gap extension penalty=0.2; protein matrix=Gonnet; protein/DNA end gap=−1; and protein/DNAGAPDIST=4. The AlignX program (a part of the vectorNTI group) may preferably be used to align an amino acid sequence of a protein with SEQ ID No: 1 using default parameters suitable for multiple alignments (gap opening penalty: 10 og; and gap extension penalty: 0.05) to determine a position of a specific amino acid within the protein.

The term "encoding" refers to an inherent characteristic of a specific nucleotide sequence in a polynucleotide, such as a gene cDNA or mRNA, which serves as a template for the synthesis of a defined nucleotide sequence (namely, rRNA, tRNA, and mRNA) or a defined amino acid sequence and the synthesis of other polymers and macromolecules in a biological process of a biological characteristic thereof. Therefore, if the transcription and translation of mRNA corresponding to a gene produces a protein in a cell or another biological system, the gene encodes the protein.

The term "amino acid" refers to a carboxylic acid with amino. Various proteins in organisms are composed of 20 essential amino acids.

The terms "protein", "polypeptide", and "peptide" can be used interchangeably in the present disclosure and refer to a polymer of amino acid residues, including a polymer in which one or more amino acid residues are a chemical analogue of a natural amino acid residue. The protein and polypeptide of the present disclosure can be produced through recombination or chemical synthesis.

The term "mutant protein" refers to a protein that is obtained through substitution, insertion, deletion, and/or addition of one or more amino acid residues based on an amino acid sequence of a parent protein.

The term "AxxB" means that amino acid A at position xx is changed into amino acid B. For example, I1879V means that I at position 1,879 is changed into V, C2186R means that C at position 2,186 is changed into R, and so on. For double or multiple mutations, mutations are separated by a "/". For example, I1879V/C2186R indicates that, relative to the amino acid sequence of SEQ ID NO: 1, I at position 1,879 is substituted by V and C at position 2,186 is substituted by R, where both mutations are present in the specific mutant ACC protein.

As used herein, the term "regulatory element" is intended to include a promoter, a terminator sequence, a leader sequence, a polyadenylation sequence, a signal peptide coding region, a marker gene, an enhancer, an IRES, and other expression control elements (for example, a transcriptional termination signal, such as a polyadenylation signal and a poly-U sequence), and the detailed description can be seen in Goeddel, "*GENE EXPRESSION TECHNOLOGY: METHODS IN ENZYMOLOGY*" 185, Academic Press, San Diego, Calif. (1990). In some cases, the regulatory element includes sequences that guide the constitutive expression of a nucleotide sequence in many types of host cells and sequences that guide the expression of the nucleotide sequence only in some host cells (such as a tissue-specific regulatory sequence). A tissue-specific promoter can mainly guide the expression in a desired tissue of interest, such as muscles, neurons, bones, skin, blood, specific organs (such as liver and pancreas), or specific cell types (such as lymphocytes). In some cases, a regulatory element can also guide the expression in a time-dependent manner (such as in a cell cycle-dependent or developmental stage-dependent manner), which may be or may not be tissue or cell type-specific. In some cases, the term "regulatory element" covers enhancer elements, such as WPRE; CMV enhancer; R-U5' fragment in LTR of HTLV-I ((Mol. Cell. Biol., Vol 8 (1): 466-472, 1988); SV40 enhancer; and an intron sequence between exons 2 and 3 of rabbit β-globin (Proc. Natl. Acad. Sci. USA., Vol. 78 (3): 1527-31, 1981).

As used herein, the term "promoter" has the meaning well known to those skilled in the art, which refers to a non-coding nucleotide sequence located upstream of a gene and capable of promoting the expression of a downstream gene. A constitutive promoter is a nucleotide sequence that will result in the generation of a gene product in a cell under most or all physiological conditions of the cell after the promoter is operably linked to a polynucleotide encoding or defining the gene product. An inducible promoter is a nucleotide sequence that will cause the generation of a gene product in a cell only when there is an inducer corresponding to the promoter in the cell after the promoter is operably linked to a polynucleotide encoding or defining the gene product. A tissue-specific promoter is a nucleotide sequence that will cause the generation of a gene product in a cell basically only when the cell is a cell of the tissue type corresponding to the promoter after the promoter is operably linked to a polynucleotide encoding or defining a gene product.

"NLS" (Nuclear Localization Signal) is an amino acid sequence that tags a protein for import into the nucleus through nuclear transport, that is, a protein with NLS is transported to the nucleus. Typically, NLS may include positively charged Lys or Arg residues that are exposed on the surface of a protein. Exemplary NLS includes, but is not limited to, SV40 large T antigen, EGL-13, c-Myc, and TUS protein.

As used herein, the term "operably linked" means that a nucleotide sequence of interest is linked to one or more regulatory elements in a manner that allows the expression of the nucleotide sequence (for example, in an in vitro transcription/translation system or in a host cell when the vector is introduced into the host cell).

The term "vector" refers to an element that is allowed to be integrated into a genome of a host cell or to self-replicate within a cell independently of its genome. The vector may include any elements that guarantee the self-replication. The vector usually carries a gene that is not a part of the central metabolism of a cell and is usually in the form of double-stranded DNA. The selection of a vector generally depends on the compatibility of the vector with a host cell into which the vector is to be introduced. When a vector needs to be used, the selection of the vector depends on a method for transforming a host cell well known to those skilled in the art. For example, a plasmid vector can be used.

The term "ACC herbicide" refers to an herbicide that can inhibit the synthesis of fatty acids in gramineous plants with high selectivity, can be transduced in plants, and can control annual or perennial gramineous weeds post-emergence. The ACC herbicides have the advantages of high efficiency, low toxicity, long application period, safety to subsequent crops, and the like, and thus occupy an important position among herbicides.

The ACC herbicides can be divided into the following 4 types: APPs, CHDs, APCHDs, and CTRs, which are shown as follows.

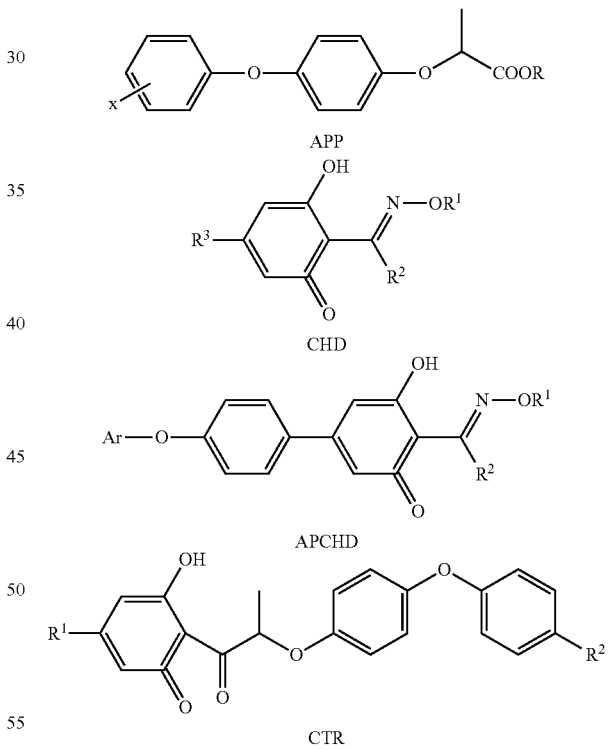

The herbicide includes, but is not limited to, alloxydim, butroxydim, clethodim, cyclohexenone, cycloxydim, sethoxydim, tepraloxydim, tralkoxydim, chloroazifop-propynyl, clodinafop-propargyl, clofop, diclofop-methyl, fenoxaprop-ethyl, fenoxaprop-p-ethyl, fenthiaprop-ethyl, fluazifop-butyl, fluazifop-p-butyl, haloxyfop-methyl, haloxyfop-p-methyl, clomazone, clefoxidim, propaquizafop, quizalofop, quizalofop-p, quizalofop-p-ethyl, quizalofop-p-tefuryl, trifluorophenoxy propionic acid, and fenoxaprop.

The "herbicide resistance" refers to the genetic ability of a plant to survive and reproduce after the plant is exposed to an herbicide at a dosage that is usually lethal to the wild-type plant. In plants, the herbicide resistance can be naturally produced or induced by a technique such as genetic engineering or screening a variant produced by tissue culture or mutagenesis. Unless otherwise stated, the herbicide resistance is heritable and allows a plant to grow and reproduce in the presence of a typical effective herbicidal treatment for a given plant by the herbicide, as suggested by the current version of "Herbicide Manual" when the present disclosure is filed. As recognized by those skilled in the art, a plant can still be considered "resistant", even if a specified degree of plant damage due to herbicide exposure is obvious. As used herein, the term "tolerance" includes "resistance" or "resistant plant" as defined herein, and the improved ability of a specific plant to tolerate various degrees of damage induced by an herbicide (typically ethyl) at the same herbicide dosage as the wild-type plant of the same genotype.

The term "parent ACC polypeptide" refers to a polypeptide derived from the ACC mutant polypeptide. In a preferred embodiment, the parent ACC polypeptide is a protein (polypeptide) that can be found in nature or is encoded by a nucleic acid that can be found in nature, where nucleotides of the nucleic acid can be obtained through genetic engineering such as genome sequencing and polymerase chain reaction (PCR), and an amino acid sequence of the protein can be deduced from the nucleotide sequence. An amino acid sequence of the wild-type ACC polypeptide is shown in SEQ ID NO: 1, for example. In some embodiments, the parent ACC polypeptide may be obtained by changing one or more amino acid residues of the wild-type ACC polypeptide without affecting the enzymatic activity.

The terms "mutant ACC protein", "mutant ACC", "mutant ACC enzyme", "mutant protein", "mutant polypeptide", "polypeptide of the present disclosure", "protein of the present disclosure", and the like can be used interchangeably. Preferably, the mutant protein may be obtained through mutation of amino acid 1,879 and/or amino acid 2,186 of the sequence shown in SEQ ID NO: 1.

The term "host organism" should be understood as any unicellular or multicellutar organism into which a nucleic acid encoding the mutant ACC protein can be introduced, including, for example, bacteria such as *E. coli*, fungi such as yeast (such as *Saccharomyces cerevisiae* (*S. cerevisiae*)), molds (such as *Aspergillus*), plant cells, and plants.

The term "plant" should be understood as any differentiated multicellular organism capable of photosynthesis, including: crop plants at a mature or developmental stage, especially monocotyledonous or dicotyledonous plants; vegetable crops including artichoke, turnip cabbage, arugula, leek, asparagus, lettuce (such as head lettuce, leaf lettuce, and romaine lettuce), bok choy, malanga, melons (such as cantaloupe, watermelon, crenshaw melon, honeydew melon, and Roman cantaloupe), rape crops (such as Brussels sprout, cabbage, cauliflower, broccoli, borecole, kale, Chinese cabbage, and bok choy), cardoon, carrot, napa, okra, onion, celery, parsley, chickpea, parsnip, chicory, pepper, *Solanum tuberosum*, gourd (such as marrow squash, cucumber, zucchini, cushaw, and pumpkin), radish, dried ball onion, rutabaga, purple eggplant (also known as eggplant), salsify, lettuce, shallot, endive, garlic, spinach, green onion, cushaw, greens, beets (sugar beets and fodder beets), sweet potato, Swiss chard, wasabi, tomato, turnip, and spices; fruits and/or vine crops such as apple, apricot, cherry, nectarine, peach, pear, plum, prune, cherry, quince, almond, chestnut, hazelnut, pecan, pistachio, walnut, citrus, blueberry, boysenberry, cranberry, currant, loganberry, raspberry, strawberry, blackberry, grape, avocado, banana, kiwi, persimmon, pomegranate, pineapple, tropical fruit, pome, melon, mango, papaya, and lychee; field crops, such as clover, alfalfa, evening primrose, meadowfoam, corn/maize (forage corn, sweet corn, and popcorn), lupulus, jojoba, peanut, rice, safflower, small grain crops (*Hordeum vulgare*, oat, rye, *Triticum aestivum*, and the like), *Sorghum bicolor*, *Nicotiana tabacum*, kapok, legumes (beans, lentil, pea, and *Glycine max*), oil plants (canola, leaf mustard, poppy, olive, sunflower, coconut, castor oil plant, cocoa bean, and groundnut), *Arabidopsis*, fiber plants (cotton, flax, hemp, and jute), *Lauraceae* (cinnamon or camphor), or a plant such as coffee, sugar cane, tea, and natural rubber plants; and/or bedding plants such as a flowering plant, cactus, a succulent plant, and/or an ornamental plant, and trees such as forests (broad-leaved and evergreen trees, such as conifers), fruit trees, ornamental trees, nut-bearing trees, shrubs, and other seedlings.

The term "plant tissue" or "plant part" includes a plant cell, a protoplast, a plant tissue culture, a plant callus, a plant piece, a plant embryo, a pollen, an ovule, a seed, a leaf, a stem, a flower, a branch, a seedling, a fruit, a nucleus, a spike, a root, a root tip, an anther, and the like.

The term "plant cell" should be understood as any cell derived or found in a plant, which is capable of forming, for example, undifferentiated tissues such as calli, differentiated tissues such as embryos, constituent parts of a plant, plants, or seeds.

The gene editing technology includes CRISPR technology, TALEN technology, and ZFN technology. "CRISPR" refers to clustered regularly interspaced short palindromic repeat, which comes from the immune system of microorganisms. A gene editing tool includes gRNA and Cas protein (such as Cas9, Cpf1, and Cas12b). The gene editing tool of TALEN refers to a restriction enzyme that can cleave a specific DNA sequence, which includes a TAL effector DNA binding domain and a DNA cleavage domain. The gene editing tool of ZFN refers to a restriction enzyme that can cleave a specific DNA sequence, which includes a zinc-finger DNA binding domain and a DNA cleavage domain. It is well known to those skilled in the art that an intracellular genome can be edited by constructing nucleotides encoding a gene editing tool and other regulatory elements into a suitable vector and then transforming the vector into a cell; and a type of the editing includes gene knockout, insertion, and base editing.

As used herein, the term "gene editing enzyme" refers to a nuclease suitable for CRISPR, TALEN, ZFN, and other editing tools. Preferably, the gene editing enzyme may be a CRISPR enzyme, also known as a Cas protein, including but not limited to: a Cas9 protein, a Cas12 protein, a Cas13 protein, a Cas14 protein, a Csm1 protein, and an FDK1 protein. The Cas protein refers to a protein family. Cas proteins have different structures according to different sources, such as SpCas9 derived from *Streptococcus pyogenes* (*S. pyogenes*) and SaCas9 derived from *Staphylococcus aureus* (*S. aureus*). Cas proteins can also be classified based on structural characteristics (such as domains), for example, the Cas12 family may include Cas12a (also known as Cpf1), Cas12b, Cas12c, Cas12i, and the like. The Cas protein may be double-stranded or single-stranded or may have no cleavage activity. The Cas protein of the present disclosure may be wild-type or a mutant thereof. A mutation type of the mutant may include amino acid substitution, substitution, or deletion. The mutant may or may not change the enzyme cleavage activity of the Cas protein. Preferably, the Cas protein of the present disclosure may only have single-strand cleavage activity or may not have cleavage activity, which may be a mutant of the wild-type Cas protein. Preferably, the Cas protein of the present disclosure may be Cas9, Cas12, Cas13, or Cas14 with single-strand cleavage activity. In a preferred embodiment, the Cas9 protein of the present disclosure may include SpCas9n(D10A), nSpCas9NG, SaCas9n, ScCas9n, and XCas9n, where "n" stands for nick, indicating a Cas protein with only single-strand cleavage activity. The mutation of a known Cas protein to obtain a Cas protein with single-strand cleavage activity or without cleavage activity is a conventional technique in the art. Those skilled in the art know that a variety of Cas proteins with nucleic acid cleavage activity have been reported in the art; and the known proteins or modified variants can all achieve the functions of the present disclosure, which are incorporated into the protection scope of the present disclosure by reference.

For example, it is clear to those skilled in the art that a structure of a protein can be changed without adversely affecting the activity and functionality of the protein. For example, one or more conservative amino acid substitutions can be introduced into an amino acid sequence of a protein without adversely affecting the activity and/or three-dimensional (3D) configuration of the protein molecule. Those skilled in the art are aware of examples and implementations of the conservative amino acid substitutions. Specifically, an amino acid residue can be substituted by another amino acid residue that belongs to the same group as the amino acid residue to be substituted. That is, a nonpolar amino acid residue can be substituted by another nonpolar amino acid residue; an uncharged polar amino acid residue can be substituted by another uncharged polar amino acid residue; a basic amino acid residue can be substituted by another basic amino acid residue; and an acidic amino acid residue can be substituted by another acidic amino acid residue. Such substituted amino acid residues may be or may not be encoded by genetic codes. As long as a substitution does not damage the biological activity of a protein, a conservative substitution in which an amino acid is substituted by another amino acid belonging to the same group falls within the scope of the present disclosure. Therefore, in addition to the above-mentioned mutations, the mutant GBSS1 protein of the present disclosure may include one or more other mutations such as conservative substitutions in the amino acid sequence. In addition, the present disclosure covers mutant ACC proteins with one or more other non-conservative substitutions, as long as the non-conservative substitutions do not significantly affect the desired function and biological activity of the protein of the present disclosure.

As well known in the art, one or more amino acid residues can be deleted from the N and/or C terminus of a protein while still retaining its functional activity. Therefore, in another aspect, the present disclosure also relates to a fragment that is obtained through deletion of one or more amino acid residues from the N-terminus and/or C-terminus of the mutant ACC protein and retains the required functional activity (such as an amino acid fragment with the mutation site of the present disclosure), which is also within the scope of the present disclosure and is called a biologically-active fragment. In the present disclosure, the "biologically-active fragment" refers to a part of the mutant ACC protein of the present disclosure, which retains the biological activity of the mutant ACC protein of the present disclosure. For example, the biologically-active fragment of the mutant ACC protein may be obtained after one or more (for example, 1-50, 1-25, 1-10, or 1-5, such as 1, 2, 3, 4, or 5) amino acid residues are deleted from the N-terminus and/or C-terminus of the protein, which still retains the biological activity of the full-length protein.

In addition, the mutant protein of the present disclosure can be modified. Modified (usually without changing the primary structure) forms may include: chemically derived forms of the mutant protein in vivo or in vitro, such as acetylated or carboxylated form. The modification may also include glycosylation, such as glycosylation modification during the synthesis and processing or further processing of the mutant protein to produce a mutant protein. The modification can be accomplished by exposing the mutant protein to a glycosylase (such as a mammalian glycosylase or deglycosylase). The modified forms may also include sequences with phosphorylated amino acid residues (such as phosphotyrosine, phosphoserine, and phosphothreonine). The mutant protein can also be modified to increase its proteolysis resistance or optimize its solubility.

The present disclosure also provides a polynucleotide encoding the mutant ACC polypeptide, which may also include additional coding and/or non-coding sequences. Preferably, the mutant ACC polypeptide may be shown in SEQ ID NOs: 2-4. Those skilled in the art are well aware that, due to the degeneracy of genetic codes, there are many different nucleic acid sequences that can encode the amino acid sequence disclosed herein. Producing other nucleic acid sequences encoding the same protein is within the competence scope of those of ordinary skill in the art, and thus the present disclosure covers nucleic acid sequences encoding the same amino acid sequence due to the degeneracy of genetic codes. For example, in order to achieve the high expression of a heterologous gene in a target host organism such as a plant, the gene can be optimized using a codon preferred by the host organism to allow better expression.

The full-length sequence of the polynucleotide of the present disclosure can usually be obtained through PCR amplification, recombination, or artificial synthesis. For the PCR amplification, primers can be designed according to the relevant nucleotide sequence disclosed in the present disclosure, especially the ORF sequence, and a commercially available cDNA library or a cDNA library prepared by a conventional method known to those skilled in the art can be used as a template to amplify the relevant sequence. When the sequence is long, it is often necessary to conduct two or more PCR amplifications, and then amplified fragments are spliced together in a correct order. The obtained nucleotide sequence can be cloned into a vector and then transformed into a cell, and then a large number of related sequences can be isolated from proliferated host cells by a conventional method. The mutation site of the present disclosure can also be introduced through artificial synthesis.

One or more copies of the polynucleotide of the present disclosure can be inserted into a host cell to increase a yield of a gene product. The copy number of the polynucleotide can be increased by integrating at least one additional copy of the sequence into a host cell genome or by integrating an amplifiable selectable marker gene with the polynucleotide, where in the latter case, a cell with the amplified copy of the selectable marker gene and the resulting additional copy of the polynucleotide can be selected by artificially cultivating the cell in the presence of a suitable selectable agent.

Methods well known to those skilled in the art can be used to construct a vector that includes a DNA sequence encoding the ACC mutant polypeptide and an appropriate transcription/translation control signal. The methods include in vitro recombinant DNA technology, DNA synthesis technology, and in vivo recombination technology. The DNA sequence can be effectively linked to an appropriate promoter in a vector to guide mRNA synthesis. The vector may also include a ribosome binding site (RBS) for translation initiation and a transcription terminator.

The vectors applicable in the present disclosure may include commercially available plasmids, such as but not limited to: pBR322 (ATCC37017), pKK223-3 (Pharmacia Fine Chemicals, Uppsala, Sweden), GEM1 (Promega Biotec, Madison, Wis., USA), pQE70, pQE60, pQE-9 (Qiagen), pD10, psiX174pBluescript II KS, pNH8A, pNH16a, pNH18A, pNH46A (Stratagene), ptrc99a, pKK223-3, pKK233-3, pDR540, pRIT5 (Pharmacia), pKK232-8, pCM7, pSV2CAT, pOG44, pXT1, pSG (Stratagene), pSVK3, pBPV, pMSG, and pSVL (Pharmacia).

The present disclosure also provides a host cell carrying a nucleic acid sequence, a nucleic acid construct, or an expression vector encoding the ACC mutant polypeptide of the present disclosure. A vector carrying a nucleic acid encoding the protein of the present disclosure is introduced into a host cell, such that the vector exists as a part of a chromosomal integration or exists as a self-replicating extra-chromosomal vector described early, or the vector can achieve gene editing on the endogenous ACC gene of the host cell. The host cell may be any host cell familiar to those skilled in the art, including a prokaryotic cell and a eukaryotic cell.

The nucleic acid sequence, nucleic acid construct, or expression vector of the present disclosure can be introduced into a host cell through a variety of techniques, including transformation, transfection, transduction, viral infection, gene gun or Ti-plasmid-mediated gene delivery, calcium phosphate transfection, DEAE-dextran-mediated transfection, lipofection, electroporation, or the like.

In the production method of the present disclosure, the cells are cultivated on a nutrient medium suitable for the production of the polypeptide by a method well known in the art. If the polypeptide is secreted into the nutrient medium, the polypeptide can be directly recovered from the medium. If the polypeptide is not secreted into the medium, the polypeptide can be recovered from a cell lysate.

As used herein, the terms "gRNA", "mature crRNA", and "guide sequence" can be used interchangeably and have the meaning commonly understood by those skilled in the art. Generally, a gRNA can include direct repeats and guide sequences, or may be basically composed of or may be composed of direct repeats and guide sequences (also called spacers in the context of endogenous CRISPR systems).

In some cases, the guide sequence can be any polynucleotide sequence that shows sufficient complementarity with a target sequence to hybridize with the target sequence and guide the specific binding of the CRISPR/Cas complex to the target sequence. In an embodiment, under optimal alignment, a complementarity degree between the guide sequence and a corresponding target sequence may be at least 50%, at least 60%, at least 70%, at least 80%, at least 90%, at least 95%, or at least 99%. Determining the optimal alignment is within the competence of those of ordinary skill in the art. For example, there are published and commercially available alignment algorithms and programs, including but not limited to Smith-Waterman, Bowtie, Geneious, Biopython, and SeqMan in ClustalW and matlab.

| Sequence Listing | | |
|---|---|---|
| Sequence No. | Type | Content |
| SEQ ID NO: 1 | Protein | Amino acid sequence of wild-type ACC |
| SEQ ID NO: 2 | Protein | Amino acid sequence of I1879V |
| SEQ ID NO: 3 | Protein | Amino acid sequence of C2186R |
| SEQ ID NO: 4 | Protein | Amino acid sequence of I1879V and C2186R double-mutation |
| SEQ ID NO: 5 | DNA | DNA sequence of I1879V |
| SEQ ID NO: 6 | DNA | DNA sequence of C2186R |
| SEQ ID NO: 7 | DNA | DNA sequence of I1879V and C2186R double-mutation |

The present disclosure has the following advantages:
1. The present disclosure screens out a group of mutant ACC proteins.
2. A plant with the mutant ACC protein of the present disclosure shows obvious herbicide resistance compared with the wild-type plant.

DETAILED DESCRIPTION OF THE EMBODIMENTS

The present disclosure will be further explained below in conjunction with examples. The following examples are only preferred examples of the present disclosure, and are not intended to limit the present disclosure in other forms. Any technical personnel familiar with the profession may use the technical content disclosed above to derive equivalent examples through equivalent changes. Any simple modification or equivalent change made to the following examples according to the technical essence of the present disclosure without departing from the content of the solutions of the present disclosure shall fall within the protection scope of the present disclosure.

Example 1 Construction of a Gene Editing Vector and Screening of a Mutation Site 1. An ABE-nCas9 base editor targeting the *Oryza sativa* endogenous ACC gene was constructed.

The ABE base editor could realize A/T->G/C base conversion within a specified sequence window. In the present disclosure, the ABE-nCas9 base editor was used as a vector, and a sgRNA (sgRNA shown in Table 1) was designed in the *Oryza sativa* endogenous ACC gene and cloned into the ABE-nCas9 vector to form a base editor targeting the *Oryza sativa* endogenous ACC gene. An amino acid sequence encoded by the *Oryza sativa* endogenous ACC gene was shown in SEQ ID No: 1.

TABLE 1

| sgRNA sequences (guide sequences) targeting Oryza sativa ACC | |
|---|---|
| sgRNA No. | guide-PAM sequence (5'-3') |
| A-ACC1879 | GAGAATATACATGGAAGTGC |
| A-ACC2186 | ATAGCACTCAATGCGGTCTG |

2. *Oryza sativa* Genetic Transformation and Transgenic Plant Identification

Multiple *Oryza sativa* varieties such as Wanzhijing 006, Nanjing 9108, and Jiahe 218 were used as experimental materials. The base editor constructed above was transformed into the *Oryza sativa* plants by *A. tumefaciens* to obtain gene-edited plants. Emerging seedlings were screened with a sethoxydim-containing medium at a concentration of SET-2: 2 mg/L. Or, edited seedlings were planted in a cultivation room. The edited seedlings and the control plants were sprayed with sethoxydim at a concentration of 0.5 g/L (corresponding to a field application dosage of 10 g. a.i/mu), and a survival rate of the seedlings was counted 10 d later.

Figure 1:
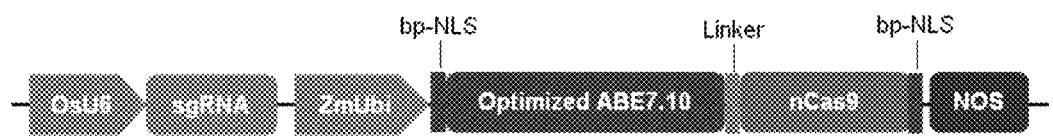
FIG. 1 is a schematic diagram of an ABE-nCas9 base editor, where OsU6 and ZmUbi are promoters; sgRNA is a gRNA; bp-NLS is a nuclear localization signal; and NOS is a terminator.
Figure 2:
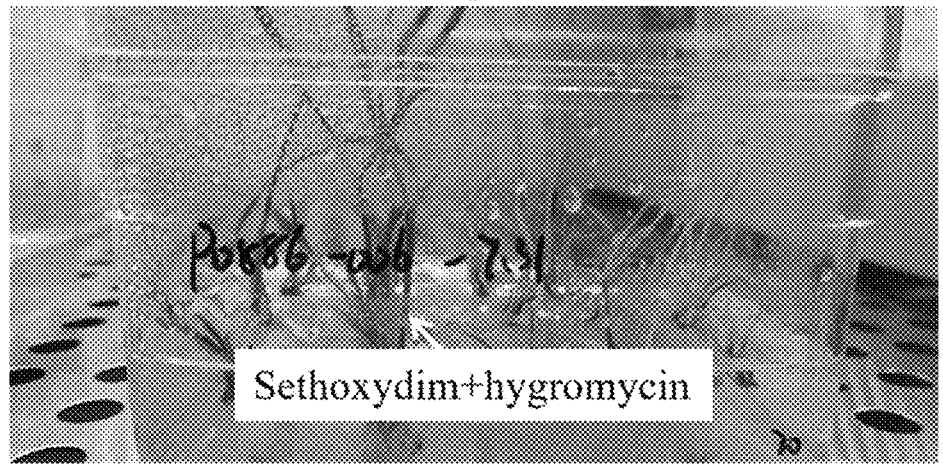
FIG. 2 shows the herbicide resistance of a plant with mutation of amino acid 1,879 of ACC relative to the wild-type.
Figure 3:
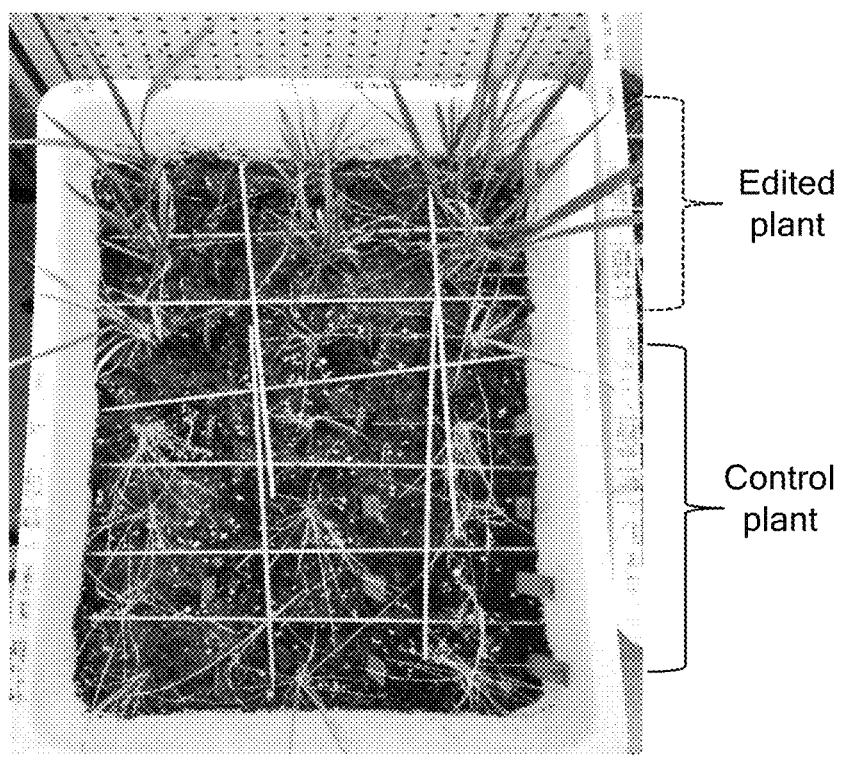
FIG. 3 shows the herbicide resistance of a plant with mutation of amino acid 2,186 of ACC relative to the wild-type.

Through screening cultivation, herbicide-resistant plants were screened out on a sethoxydim-containing medium. As shown in FIG. 2, plants indicated by the arrow were able to tolerate the herbicide and showed resistance to the herbicide compared with other plants. The above herbicide-resistant plants were identified by PCR and sequencing, and it was found that the herbicide-resistant plants had an expected base substitution within a target range and a specific editing type was I1879V. In addition, herbicide-resistant plants were also screened out in the cultivation room. As shown in FIG. 3, edited plants were able to tolerate the herbicide and showed resistance to the herbicide compared with the control plants. The above herbicide-resistant plants were identified by PCR and sequencing, and it was found that the herbicide-resistant plants had an expected base substitution within a target range and a specific editing type was C2186R.

Figure 4:
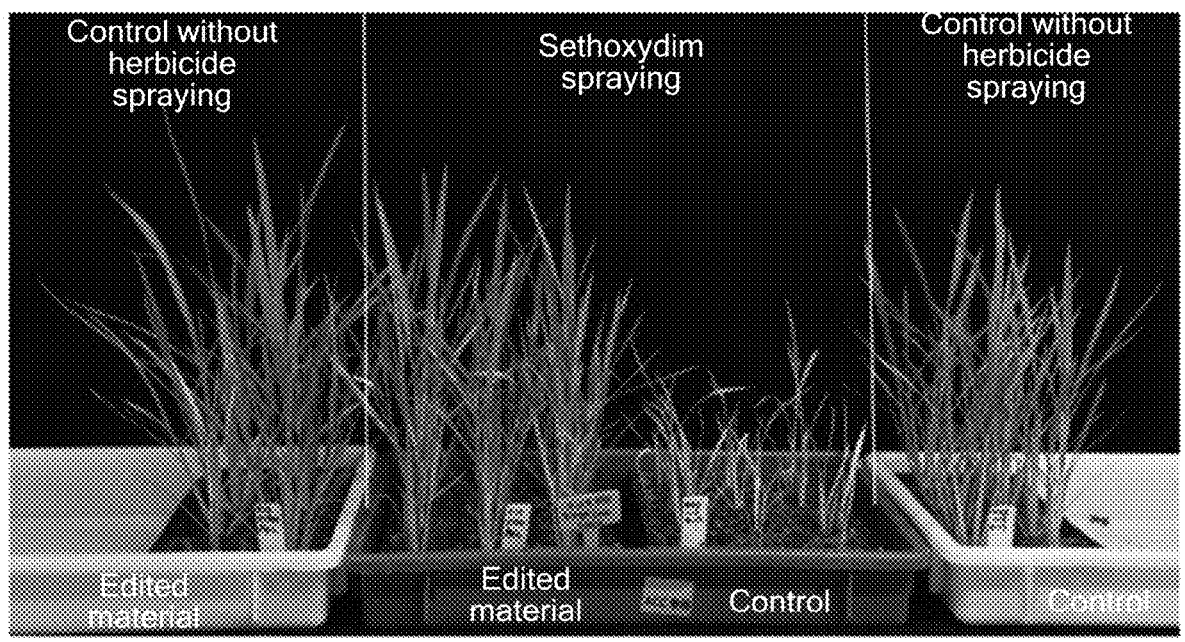
FIG. 4 shows the tolerance of an I1879V edited plant to sethoxydim.

For I1879V edited *Oryza sativa* plants, the dosage of sethoxydim was further increased to a corresponding field application dosage of 15 g. a.i/mu. 14 d later, the control was obviously yellow and dead, and the edited material grew normally, as shown in FIG. 4. The dosage of sethoxydim was further increased to 30 g. a.i/mu. After the plants were further cultivated for 20 d, all wild-type plants died, but the edited plants still showed significant herbicide resistance, with phytotoxicity only of about 30%.

Example 2 Resistance to Other Types of Herbicides

The I1879V and C2186R edited *Oryza sativa* plants obtained in Example 1 were planted, and the resistance to other types of herbicides was tested, such as phenthodim, quizalofop-p, fenoxaprop-p-ethyl, clethodim, haloxyfop-p-methyl, fenoxaprop, and butyclofen.

Figure 5:
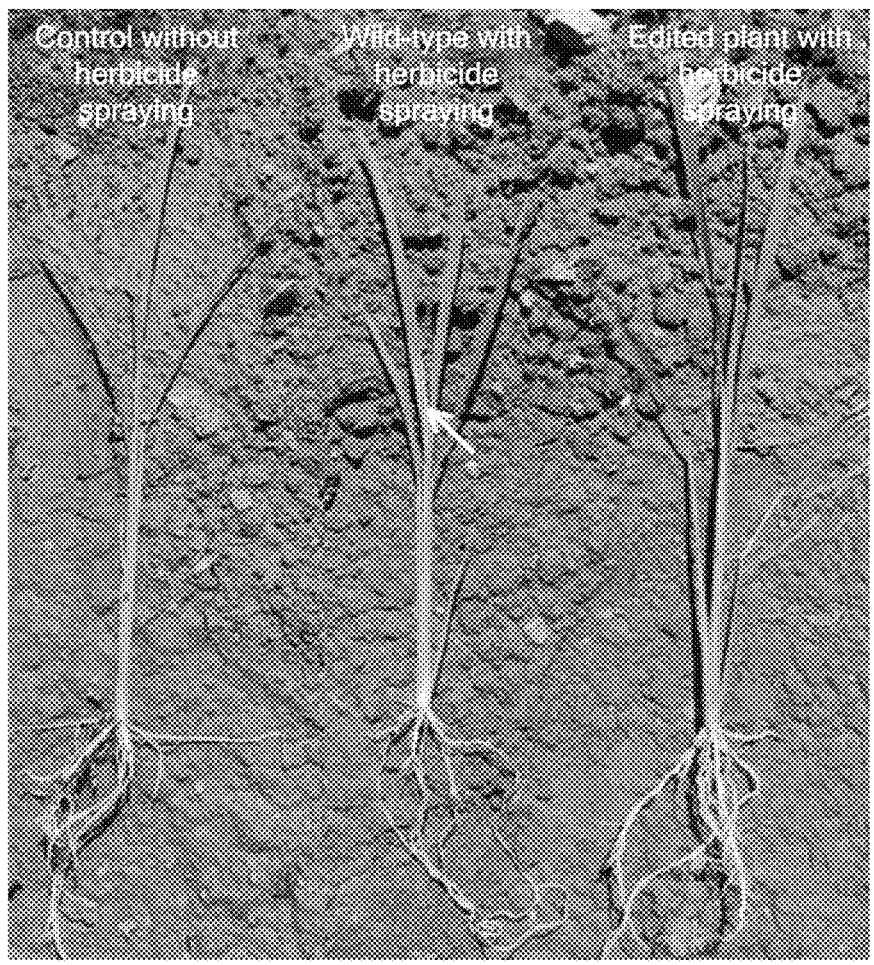
FIG. 5 shows the tolerance of an I1879V edited plant to phenthodim after phenthodim is sprayed for 20 d.
Figure 6A:
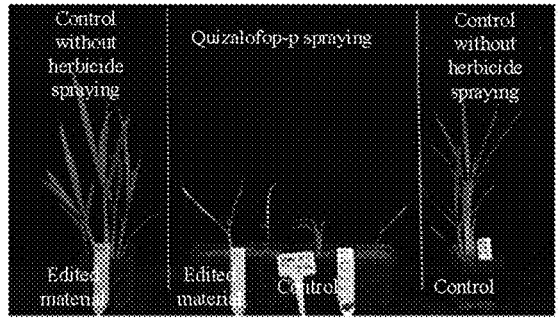
FIG. 6 shows the tolerance of I1879V and C2186R edited plants to quizalofop-p and fenoxaprop-p-ethyl.
Figure 6B:
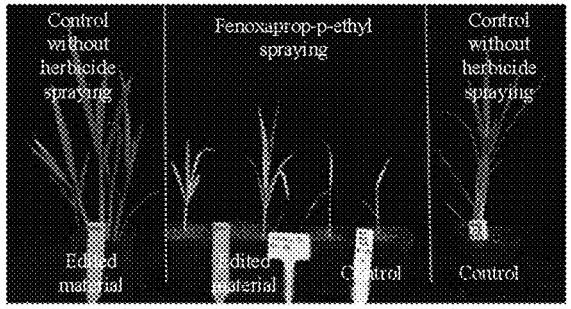
Figure 6C:
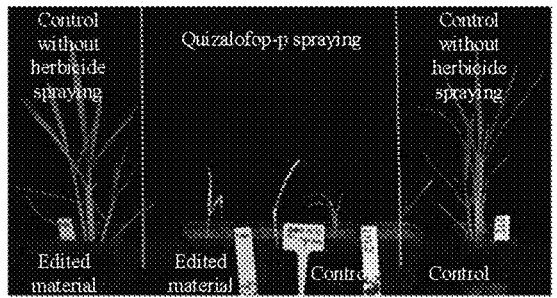
Figure 6D:
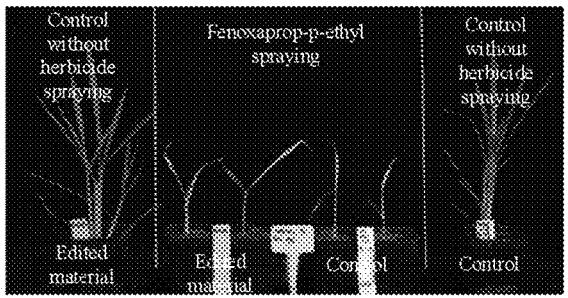

2.1 Phenthodim:

Dibble *Oryza sativa* plants at the seedling stage in the field were selected and sprayed with phenthodim at 20 g.a.i./mu (4 times a recommended dosage), and then results were observed. After the phenthodim was sprayed for 7 d, the wild-type plants showed obvious chlorosis and spots, but the I1879V edited plants showed no visible phytotoxicity. After the phenthodim was applied for 20 d, as shown in FIG. 5, the wild-type plants showed serious phytotoxicity (the arrow in FIG. 5 indicated obvious phytotoxicity), and its growth was also severely affected; and the I1879V edited plants showed little difference in biomass from the control group. That is, even 20 d later, the I1879V edited plants still showed excellent resistance to phenthodim, had no obvious phytotoxicity, and were not affected in growth. However, compared with the wild-type control, the C2186R edited plant showed some resistance. Compared with the I1879V edited plant, the C2186R edited plant showed obvious phytotoxicity at 20 g.a.i./mu of phenthodim, and there were chlorosis and spots at bases of leaves of the edited material, which was not safe enough for practical use.

2.2 Quizalofop-p and fenoxaprop-p-ethyl

Quizalofop-p and fenoxaprop-p-ethyl were each applied at 5 g.a.i./mu to I1879V edited plants and C2186R edited plants, and results were observed 14 d later. As shown in FIG. 6, 14 d later, there was no significant difference between the edited plants and the wild-type control, indicating that the above-mentioned edited plants failed to produce tolerance to quizalofop-p or fenoxaprop-p-ethyl.

Figure 7:
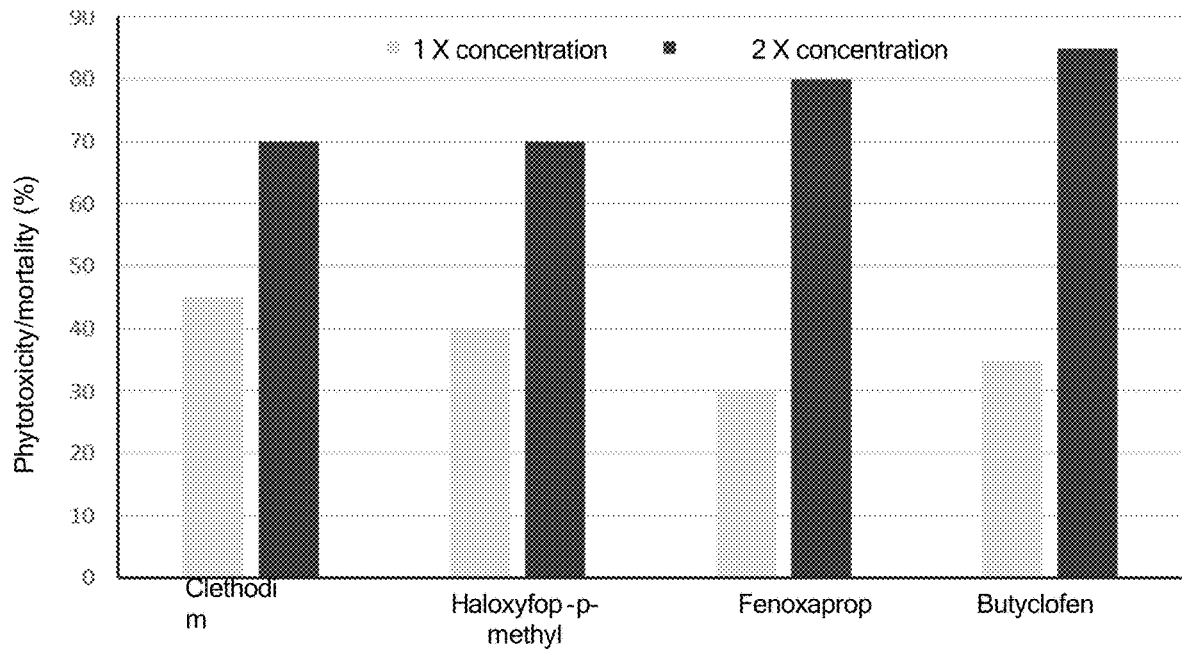
FIG. 7 shows the tolerance of an I1879V edited plant to different herbicides.

2.3 Clethodim, haloxyfop-p-methyl, fenoxaprop, and butyclofen:

The tolerance of the I1879V edited plants to clethodim, haloxyfop-p-methyl, fenoxaprop, and butyclofen was tested, where the clethodim, haloxyfop-p-methyl, and fenoxaprop were each applied at concentrations of 5 g.a.i./mu (1×) and 10 g.a.i./mu (2×); and the butyclofen was applied at concentrations of 10 g.a.i./mu (1×) and 20 g.a.i./mu (2×). After the herbicide was applied for 20 d, the growth of the edited plants was observed and the herbicide resistance of the edited plants was counted. As shown in FIG. 7, the I1879V edited plants showed some phytotoxicity at the above-mentioned 1× herbicide concentration, with a mortality rate of 30% to 50%; and at the above-mentioned 2× herbicide concentration, the edited plants were basically in a non-resistant state, with a mortality rate of 70% to 90%.

All documents mentioned in the present disclosure are cited as references in the present application, as if each document was individually cited as a reference. In addition, it should be understood that various changes or modifications may be made to the present disclosure by those skilled in the art after reading the above teaching content of the present disclosure, and these equivalent forms also fall within the scope defined by the appended claims of the present disclosure.

What is claimed is:

1. A method for imparting phenthodim resistance to a plant, comprising a step of allowing endogenous acetyl-CoA carboxylase (ACC) of the plant to mutate to introduce a mutant ACC into a plant cell, a plant seed, a plant tissue, a plant part, or the plant, wherein compared to an amino acid sequence of a parent ACC, the mutant ACC has a mutation at an amino acid corresponding to amino acid 1,879 of an amino acid sequence shown in SEQ ID NO: 1, wherein the amino acid 1,879 is mutated into valine (V); and
  the plant is rice;
  wherein a method for controlling weeds comprises:
  a) providing a phenthodim-resistant plant prepared by the method for imparting the phenthodim resistance to the plant; and
  b) applying an effective amount of phenthodim to the phenthodim-resistant plant and the weeds nearby to control the weeds near the phenthodim-resistant plant.

2. The method according to claim 1, wherein the parent ACC is derived from a monocotyledonous plant or a dicotyledonous plant.

3. The method according to claim 2, wherein the parent ACC is derived from Oryza sativa.

4. The method according to claim 1, wherein the method comprises a step of allowing the mutant ACC to express in the plant cell, the plant seed, the plant tissue, the plant part, or the plant.

5. The method according to claim 1, wherein the method comprises:
  introducing the mutant ACC with a gene editing tool.

6. The method according to claim 5, wherein the gene editing tool is one or more selected from the group consisting of clustered regularly interspaced short palindromic repeat (CRISPR), transcription activator-like effector nuclease (TALEN), and zinc-finger nuclease (ZFN).

7. The method according to claim 2, wherein the method comprises a step of allowing the mutant ACC to express in the plant cell, the plant seed, the plant tissue, the plant part, or the plant.

8. The method according to claim 3, wherein the method comprises a step of allowing the mutant ACC to express in the plant cell, the plant seed, the plant tissue, the plant part, or the plant.

* * * * *

SEQUENCE LISTING

<160> NUMBER OF SEQ ID NOS: 9

<210> SEQ ID NO 1
<211> LENGTH: 2414

<212> TYPE: PRT
<213> ORGANISM: Oryza sativa

<400> SEQUENCE: 1

```
Met Pro Met Arg Pro Trp Glu Phe Ile Ile Leu Gly Arg Thr Ala Pro
1               5                   10                  15

Ile Ser Pro Pro Leu Gly Ile Ser Ala Phe Ser Arg Pro Leu Arg
            20                  25                  30

Leu Arg Leu Arg Leu Arg Leu Ala Ala Val Val Asp Ala Ala Arg Ile
        35                  40                  45

Gln Thr Pro Pro Arg Val Ala Phe Ser Ala Phe Phe Phe Phe Phe
    50                  55                  60

Phe Phe Ser Glu Gly Leu Ser Arg Glu Gly Thr Ala Ala Arg Leu Pro
65                  70                  75                  80

Ala Leu Ile Tyr Arg Val Pro Phe Ile Pro Cys Leu Leu Gln Leu Gln
                85                  90                  95

Ile Arg Ala Pro His Ala Asp Pro Arg Pro Ala Gly Phe Ser Cys Ala
            100                 105                 110

His His Phe Leu Ala Leu Ala Gln Gly Leu Ser Ser Ser Leu Leu Ser
        115                 120                 125

Gly Thr Ile Ser His Ile Trp Gly Phe Ile Phe Ser Leu Tyr Gly Thr
    130                 135                 140

Thr His Leu Arg Asn Arg Ala Ile Leu Leu Phe Gly Leu Ala Gly Ile
145                 150                 155                 160

Ile Asp Leu Pro Asn Asp Ala Ala Ser Glu Val Asp Ile Ser His Gly
                165                 170                 175

Ser Glu Asp Pro Arg Gly Pro Thr Val Pro Gly Ser Tyr Gln Met Asn
            180                 185                 190

Gly Ile Ile Asn Glu Thr His Asn Gly Arg His Ala Ser Val Ser Lys
        195                 200                 205

Val Val Glu Phe Cys Thr Ala Leu Gly Gly Lys Thr Pro Ile His Ser
210                 215                 220

Val Leu Val Ala Asn Asn Gly Met Ala Ala Lys Phe Met Arg Ser
225                 230                 235                 240

Val Arg Thr Trp Ala Asn Asp Thr Phe Gly Ser Glu Lys Ala Ile Gln
                245                 250                 255

Leu Ile Ala Met Ala Thr Pro Glu Asp Leu Arg Ile Asn Ala Glu His
            260                 265                 270

Ile Arg Ile Ala Asp Gln Phe Val Glu Val Pro Gly Gly Thr Asn Asn
        275                 280                 285

Asn Asn Tyr Ala Asn Val Gln Leu Ile Val Glu Ile Ala Glu Arg Thr
    290                 295                 300

Gly Val Ser Ala Val Trp Pro Gly Trp Gly His Ala Ser Glu Asn Pro
305                 310                 315                 320

Glu Leu Pro Asp Ala Leu Thr Ala Lys Gly Ile Val Phe Leu Gly Pro
                325                 330                 335

Pro Ala Ser Ser Met His Ala Leu Gly Asp Lys Val Gly Ser Ala Leu
            340                 345                 350

Ile Ala Gln Ala Ala Gly Val Pro Thr Leu Ala Trp Ser Gly Ser His
        355                 360                 365

Val Glu Val Pro Leu Glu Cys Cys Leu Asp Ser Ile Pro Asp Glu Met
    370                 375                 380

Tyr Arg Lys Ala Cys Val Thr Thr Glu Glu Ala Val Ala Ser Cys
385                 390                 395                 400
```

-continued

Gln Val Val Gly Tyr Pro Ala Met Ile Lys Ala Ser Trp Gly Gly
                405                 410                 415

Gly Lys Gly Ile Arg Lys Val His Asn Asp Asp Glu Val Arg Thr Leu
            420                 425                 430

Phe Lys Gln Val Gln Gly Glu Val Pro Gly Ser Pro Ile Phe Ile Met
        435                 440                 445

Arg Leu Ala Ala Gln Ser Arg His Leu Glu Val Gln Leu Leu Cys Asp
    450                 455                 460

Gln Tyr Gly Asn Val Ala Ala Leu His Ser Arg Asp Cys Ser Val Gln
465                 470                 475                 480

Arg Arg His Gln Lys Ile Ile Glu Glu Gly Pro Val Thr Val Ala Pro
                485                 490                 495

Arg Glu Thr Val Lys Glu Leu Glu Gln Ala Ala Arg Arg Leu Ala Lys
            500                 505                 510

Ala Val Gly Tyr Val Gly Ala Ala Thr Val Glu Tyr Leu Tyr Ser Met
        515                 520                 525

Glu Thr Gly Glu Tyr Tyr Phe Leu Glu Leu Asn Pro Arg Leu Gln Val
    530                 535                 540

Glu His Pro Val Thr Glu Trp Ile Ala Glu Val Asn Leu Pro Ala Ala
545                 550                 555                 560

Gln Val Ala Val Gly Met Gly Ile Pro Leu Trp Gln Ile Pro Glu Ile
                565                 570                 575

Arg Arg Phe Tyr Gly Met Asn His Gly Gly Gly Tyr Asp Leu Trp Arg
            580                 585                 590

Lys Thr Ala Ala Leu Ala Thr Pro Phe Asn Phe Asp Glu Val Asp Ser
        595                 600                 605

Lys Trp Pro Lys Gly His Cys Val Ala Val Arg Ile Thr Ser Glu Asp
    610                 615                 620

Pro Asp Asp Gly Phe Lys Pro Thr Gly Gly Lys Val Lys Glu Ile Ser
625                 630                 635                 640

Phe Lys Ser Lys Pro Asn Val Trp Ala Tyr Phe Ser Val Lys Ser Gly
                645                 650                 655

Gly Gly Ile His Glu Phe Ala Asp Ser Gln Phe Gly His Val Phe Ala
            660                 665                 670

Tyr Gly Thr Thr Arg Ser Ala Ala Ile Thr Thr Met Ala Leu Ala Leu
        675                 680                 685

Lys Glu Val Gln Ile Arg Gly Glu Ile His Ser Asn Val Asp Tyr Thr
    690                 695                 700

Val Asp Leu Leu Asn Ala Ser Asp Phe Arg Glu Asn Lys Ile His Thr
705                 710                 715                 720

Gly Trp Leu Asp Thr Arg Ile Ala Met Arg Val Gln Ala Glu Arg Pro
                725                 730                 735

Pro Trp Tyr Ile Ser Val Val Gly Gly Ala Leu Tyr Lys Thr Val Thr
            740                 745                 750

Ala Asn Thr Ala Thr Val Ser Asp Tyr Val Gly Tyr Leu Thr Lys Gly
        755                 760                 765

Gln Ile Pro Pro Lys His Ile Ser Leu Val Tyr Thr Thr Val Ala Leu
    770                 775                 780

Asn Ile Asp Gly Lys Lys Tyr Thr Ile Asp Thr Val Arg Ser Gly His
785                 790                 795                 800

Gly Ser Tyr Arg Leu Arg Met Asn Gly Ser Thr Val Asp Ala Asn Val
                805                 810                 815

-continued

Gln Ile Leu Cys Asp Gly Gly Leu Leu Met Gln Leu Asp Gly Asn Ser
                820                 825                 830

His Val Ile Tyr Ala Glu Glu Ala Ser Gly Thr Arg Leu Leu Ile
            835                 840                 845

Asp Gly Lys Thr Cys Met Leu Gln Asn Asp His Asp Pro Ser Lys Leu
        850                 855                 860

Leu Ala Glu Thr Pro Cys Lys Leu Leu Arg Phe Leu Val Ala Asp Gly
865                 870                 875                 880

Ala His Val Asp Ala Asp Val Pro Tyr Ala Glu Val Glu Val Met Lys
                885                 890                 895

Met Cys Met Pro Leu Leu Ser Pro Ala Ser Gly Val Ile His Val Val
                900                 905                 910

Met Ser Glu Gly Gln Ala Met Gln Ala Gly Asp Leu Ile Ala Arg Leu
            915                 920                 925

Asp Leu Asp Asp Pro Ser Ala Val Lys Arg Ala Glu Pro Phe Glu Asp
        930                 935                 940

Thr Phe Pro Gln Met Gly Leu Pro Ile Ala Ala Ser Gly Gln Val His
945                 950                 955                 960

Lys Leu Cys Ala Ala Ser Leu Asn Ala Cys Arg Met Ile Leu Ala Gly
                965                 970                 975

Tyr Glu His Asp Ile Asp Lys Val Val Pro Glu Leu Val Tyr Cys Leu
            980                 985                 990

Asp Thr Pro Glu Leu Pro Phe Leu Gln Trp Glu Glu Leu Met Ser Val
        995                 1000                1005

Leu Ala Thr Arg Leu Pro Arg Asn Leu Lys Ser Glu Leu Glu Gly
        1010                1015                1020

Lys Tyr Glu Glu Tyr Lys Val Lys Phe Asp Ser Gly Ile Ile Asn
        1025                1030                1035

Asp Phe Pro Ala Asn Met Leu Arg Val Ile Ile Glu Glu Asn Leu
        1040                1045                1050

Ala Cys Gly Ser Glu Lys Glu Lys Ala Thr Asn Glu Arg Leu Val
        1055                1060                1065

Glu Pro Leu Met Ser Leu Leu Lys Ser Tyr Glu Gly Gly Arg Glu
        1070                1075                1080

Ser His Ala His Phe Val Val Lys Ser Leu Phe Glu Glu Tyr Leu
        1085                1090                1095

Tyr Val Glu Glu Leu Phe Ser Asp Gly Ile Gln Ser Asp Val Ile
        1100                1105                1110

Glu Arg Leu Arg Leu Gln His Ser Lys Asp Leu Gln Lys Val Val
        1115                1120                1125

Asp Ile Val Leu Ser His Gln Ser Val Arg Asn Lys Thr Lys Leu
        1130                1135                1140

Ile Leu Lys Leu Met Glu Ser Leu Val Tyr Pro Asn Pro Ala Ala
        1145                1150                1155

Tyr Arg Asp Gln Leu Ile Arg Phe Ser Ser Leu Asn His Lys Ala
        1160                1165                1170

Tyr Tyr Lys Leu Ala Leu Lys Ala Ser Glu Leu Leu Glu Gln Thr
        1175                1180                1185

Lys Leu Ser Glu Leu Arg Ala Arg Ile Ala Arg Ser Leu Ser Glu
        1190                1195                1200

Leu Glu Met Phe Thr Glu Glu Ser Lys Gly Leu Ser Met His Lys
        1205                1210                1215

Arg Glu Ile Ala Ile Lys Glu Ser Met Glu Asp Leu Val Thr Ala

```
                1220                1225                1230

Pro Leu Pro Val Glu Asp Ala Leu Ile Ser Leu Phe Asp Cys Ser
        1235                1240                1245

Asp Thr Thr Val Gln Gln Arg Val Ile Glu Thr Tyr Ile Ala Arg
        1250                1255                1260

Leu Tyr Gln Pro His Leu Val Lys Asp Ser Ile Lys Met Lys Trp
        1265                1270                1275

Ile Glu Ser Gly Val Ile Ala Leu Trp Glu Phe Pro Glu Gly His
        1280                1285                1290

Phe Asp Ala Arg Asn Gly Gly Ala Val Leu Gly Asp Lys Arg Trp
        1295                1300                1305

Gly Ala Met Val Ile Val Lys Ser Leu Glu Ser Leu Ser Met Ala
        1310                1315                1320

Ile Arg Phe Ala Leu Lys Glu Thr Ser His Tyr Thr Ser Ser Glu
        1325                1330                1335

Gly Asn Met Met His Ile Ala Leu Leu Gly Ala Asp Asn Lys Met
        1340                1345                1350

His Ile Ile Gln Glu Ser Gly Asp Asp Ala Asp Arg Ile Ala Lys
        1355                1360                1365

Leu Pro Leu Ile Leu Lys Asp Asn Val Thr Asp Leu His Ala Ser
        1370                1375                1380

Gly Val Lys Thr Ile Ser Phe Ile Val Gln Arg Asp Glu Ala Arg
        1385                1390                1395

Met Thr Met Arg Arg Thr Phe Leu Trp Ser Asp Glu Lys Leu Ser
        1400                1405                1410

Tyr Glu Glu Glu Pro Ile Leu Arg His Val Glu Pro Pro Leu Ser
        1415                1420                1425

Ala Leu Leu Glu Leu Asp Lys Leu Lys Val Lys Gly Tyr Asn Glu
        1430                1435                1440

Met Lys Tyr Thr Pro Ser Arg Asp Arg Gln Trp His Ile Tyr Thr
        1445                1450                1455

Leu Arg Asn Thr Glu Asn Pro Lys Met Leu His Arg Val Phe Phe
        1460                1465                1470

Arg Thr Leu Val Arg Gln Pro Ser Val Ser Asn Lys Phe Ser Ser
        1475                1480                1485

Gly Gln Ile Gly Asp Met Glu Val Gly Ser Ala Glu Glu Pro Leu
        1490                1495                1500

Ser Phe Thr Ser Thr Ser Ile Leu Arg Ser Leu Met Thr Ala Ile
        1505                1510                1515

Glu Glu Leu Glu Leu His Ala Ile Arg Thr Gly His Ser His Met
        1520                1525                1530

Tyr Leu His Val Leu Lys Glu Gln Lys Leu Leu Asp Leu Val Pro
        1535                1540                1545

Val Ser Gly Asn Thr Val Leu Asp Val Gly Gln Asp Glu Ala Thr
        1550                1555                1560

Ala Tyr Ser Leu Leu Lys Glu Met Ala Met Lys Ile His Glu Leu
        1565                1570                1575

Val Gly Ala Arg Met His His Leu Ser Val Cys Gln Trp Glu Val
        1580                1585                1590

Lys Leu Lys Leu Asp Cys Asp Gly Pro Ala Ser Gly Thr Trp Arg
        1595                1600                1605

Ile Val Thr Thr Asn Val Thr Ser His Thr Cys Thr Val Asp Ile
        1610                1615                1620
```

```
Tyr Arg Glu Met Glu Asp Lys Glu Ser Arg Lys Leu Val Tyr His
1625                1630                1635

Pro Ala Thr Pro Ala Ala Gly Pro Leu His Gly Val Ala Leu Asn
1640                1645                1650

Asn Pro Tyr Gln Pro Leu Ser Val Ile Asp Leu Lys Arg Cys Ser
1655                1660                1665

Ala Arg Asn Asn Arg Thr Thr Tyr Cys Tyr Asp Phe Pro Leu Ala
1670                1675                1680

Phe Glu Thr Ala Val Arg Lys Ser Trp Ser Ser Thr Ser Gly
1685                1690                1695

Ala Ser Lys Gly Val Glu Asn Ala Gln Cys Tyr Val Lys Ala Thr
1700                1705                1710

Glu Leu Val Phe Ala Asp Lys His Gly Ser Trp Gly Thr Pro Leu
1715                1720                1725

Val Gln Met Asp Arg Pro Ala Gly Leu Asn Asp Ile Gly Met Val
1730                1735                1740

Ala Trp Thr Leu Lys Met Ser Thr Pro Glu Phe Pro Ser Gly Arg
1745                1750                1755

Glu Ile Ile Val Val Ala Asn Asp Ile Thr Phe Arg Ala Gly Ser
1760                1765                1770

Phe Gly Pro Arg Glu Asp Ala Phe Phe Glu Ala Val Thr Asn Leu
1775                1780                1785

Ala Cys Glu Lys Lys Leu Pro Leu Ile Tyr Leu Ala Ala Asn Ser
1790                1795                1800

Gly Ala Arg Ile Gly Ile Ala Asp Glu Val Lys Ser Cys Phe Arg
1805                1810                1815

Val Gly Trp Ser Asp Asp Gly Ser Pro Glu Arg Gly Phe Gln Tyr
1820                1825                1830

Ile Tyr Leu Ser Glu Glu Asp Tyr Ala Arg Ile Gly Thr Ser Val
1835                1840                1845

Ile Ala His Lys Met Gln Leu Asp Ser Gly Glu Ile Arg Trp Val
1850                1855                1860

Ile Asp Ser Val Val Gly Lys Glu Asp Gly Leu Gly Val Glu Asn
1865                1870                1875

Ile His Gly Ser Ala Ala Ile Ala Ser Ala Tyr Ser Arg Ala Tyr
1880                1885                1890

Lys Glu Thr Phe Thr Leu Thr Phe Val Thr Gly Arg Thr Val Gly
1895                1900                1905

Ile Gly Ala Tyr Leu Ala Arg Leu Gly Ile Arg Cys Ile Gln Arg
1910                1915                1920

Leu Asp Gln Pro Ile Ile Leu Thr Gly Tyr Ser Ala Leu Asn Lys
1925                1930                1935

Leu Leu Gly Arg Glu Val Tyr Ser Ser His Met Gln Leu Gly Gly
1940                1945                1950

Pro Lys Ile Met Ala Thr Asn Gly Val Val His Leu Thr Val Ser
1955                1960                1965

Asp Asp Leu Glu Gly Val Ser Asn Ile Leu Arg Trp Leu Ser Tyr
1970                1975                1980

Val Pro Ala Tyr Ile Gly Gly Pro Leu Pro Val Thr Thr Pro Leu
1985                1990                1995

Asp Pro Pro Asp Arg Pro Val Ala Tyr Ile Pro Glu Asn Ser Cys
2000                2005                2010
```

```
Asp Pro  Arg Ala Ala Ile Arg  Gly Val Asp Ser  Gln Gly Lys
    2015             2020              2025

Trp Leu  Gly Gly Met Phe Asp  Lys Asp Ser Phe  Val Glu Thr Phe
    2030             2035              2040

Glu Gly  Trp Ala Lys Thr Val  Val Thr Gly Arg  Ala Lys Leu Gly
    2045             2050              2055

Gly Ile  Pro Val Gly Val Ile  Ala Val Glu Thr  Gln Thr Met Met
    2060             2065              2070

Gln Thr  Ile Pro Ala Asp Pro  Gly Gln Leu Asp  Ser Arg Glu Gln
    2075             2080              2085

Ser Val  Pro Arg Ala Gly Gln  Val Trp Phe Pro  Asp Ser Ala Thr
    2090             2095              2100

Lys Thr  Ala Gln Ala Leu Leu  Asp Phe Asn Arg  Glu Gly Leu Pro
    2105             2110              2115

Leu Phe  Ile Leu Ala Asn Trp  Arg Gly Phe Ser  Gly Gly Gln Arg
    2120             2125              2130

Asp Leu  Phe Glu Gly Ile Leu  Gln Ala Gly Ser  Thr Ile Val Glu
    2135             2140              2145

Asn Leu  Arg Thr Tyr Asn Gln  Pro Ala Phe Val  Tyr Ile Pro Met
    2150             2155              2160

Ala Ala  Glu Leu Arg Gly Gly  Ala Trp Val Val  Val Asp Ser Lys
    2165             2170              2175

Ile Asn  Pro Asp Arg Ile Glu  Cys Tyr Ala Glu  Arg Thr Ala Lys
    2180             2185              2190

Gly Asn  Val Leu Glu Pro Gln  Gly Leu Ile Glu  Ile Lys Phe Arg
    2195             2200              2205

Ser Glu  Glu Leu Gln Asp Cys  Met Ser Arg Leu  Asp Pro Thr Leu
    2210             2215              2220

Ile Asp  Leu Lys Ala Lys Leu  Glu Val Ala Asn  Lys Asn Gly Ser
    2225             2230              2235

Ala Asp  Thr Lys Ser Leu Gln  Glu Asn Ile Glu  Ala Arg Thr Lys
    2240             2245              2250

Gln Leu  Met Pro Leu Tyr Thr  Gln Ile Ala Ile  Arg Phe Ala Glu
    2255             2260              2265

Leu His  Asp Thr Ser Leu Arg  Met Ala Ala Lys  Gly Val Ile Lys
    2270             2275              2280

Lys Val  Val Asp Trp Glu Glu  Ser Arg Ser Phe  Phe Tyr Lys Arg
    2285             2290              2295

Leu Arg  Arg Arg Ile Ser Glu  Asp Val Leu Ala  Lys Glu Ile Arg
    2300             2305              2310

Ala Val  Ala Gly Glu Gln Phe  Ser His Gln Pro  Ala Ile Glu Leu
    2315             2320              2325

Ile Lys  Lys Trp Tyr Ser Ala  Ser His Ala Ala  Glu Trp Asp Asp
    2330             2335              2340

Asp Asp  Ala Phe Val Ala Trp  Met Asp Asn Pro  Glu Asn Tyr Lys
    2345             2350              2355

Asp Tyr  Ile Gln Tyr Leu Lys  Ala Gln Arg Val  Ser Gln Ser Leu
    2360             2365              2370

Ser Ser  Leu Ser Asp Ser Ser  Ser Asp Leu Gln  Ala Leu Pro Gln
    2375             2380              2385

Gly Leu  Ser Met Leu Leu Asp  Lys Met Asp Pro  Ser Arg Arg Ala
    2390             2395              2400

Gln Leu  Val Glu Glu Ile Arg  Lys Val Leu Gly
```

-continued

```
        2405              2410

<210> SEQ ID NO 2
<211> LENGTH: 2414
<212> TYPE: PRT
<213> ORGANISM: Artificial Sequence
<220> FEATURE:
<223> OTHER INFORMATION: mutant ACC

<400> SEQUENCE: 2

Met Pro Met Arg Pro Trp Glu Phe Ile Ile Leu Gly Arg Thr Ala Pro
1               5                   10                  15

Ile Ser Pro Pro Pro Leu Gly Ile Ser Ala Phe Ser Arg Pro Leu Arg
            20                  25                  30

Leu Arg Leu Arg Leu Arg Leu Ala Ala Val Val Asp Ala Ala Arg Ile
        35                  40                  45

Gln Thr Pro Pro Arg Val Ala Phe Ser Ala Phe Phe Phe Phe Phe Phe
    50                  55                  60

Phe Phe Ser Glu Gly Leu Ser Arg Glu Gly Thr Ala Ala Arg Leu Pro
65                  70                  75                  80

Ala Leu Ile Tyr Arg Val Pro Phe Ile Pro Cys Leu Leu Gln Leu Gln
                85                  90                  95

Ile Arg Ala Pro His Ala Asp Pro Arg Pro Ala Gly Phe Ser Cys Ala
            100                 105                 110

His His Phe Leu Ala Leu Ala Gln Gly Leu Ser Ser Ser Leu Leu Ser
        115                 120                 125

Gly Thr Ile Ser His Ile Trp Gly Phe Ile Phe Ser Leu Tyr Gly Thr
130                 135                 140

Thr His Leu Arg Asn Arg Ala Ile Leu Leu Phe Gly Leu Ala Gly Ile
145                 150                 155                 160

Ile Asp Leu Pro Asn Asp Ala Ala Ser Glu Val Asp Ile Ser His Gly
                165                 170                 175

Ser Glu Asp Pro Arg Gly Pro Thr Val Pro Gly Ser Tyr Gln Met Asn
            180                 185                 190

Gly Ile Ile Asn Glu Thr His Asn Gly Arg His Ala Ser Val Ser Lys
        195                 200                 205

Val Val Glu Phe Cys Thr Ala Leu Gly Gly Lys Thr Pro Ile His Ser
    210                 215                 220

Val Leu Val Ala Asn Asn Gly Met Ala Ala Ala Lys Phe Met Arg Ser
225                 230                 235                 240

Val Arg Thr Trp Ala Asn Asp Thr Phe Gly Ser Glu Lys Ala Ile Gln
                245                 250                 255

Leu Ile Ala Met Ala Thr Pro Glu Asp Leu Arg Ile Asn Ala Glu His
            260                 265                 270

Ile Arg Ile Ala Asp Gln Phe Val Glu Val Pro Gly Gly Thr Asn Asn
        275                 280                 285

Asn Asn Tyr Ala Asn Val Gln Leu Ile Val Glu Ile Ala Glu Arg Thr
    290                 295                 300

Gly Val Ser Ala Val Trp Pro Gly Trp Gly His Ala Ser Glu Asn Pro
305                 310                 315                 320

Glu Leu Pro Asp Ala Leu Thr Ala Lys Gly Ile Val Phe Leu Gly Pro
                325                 330                 335

Pro Ala Ser Ser Met His Ala Leu Gly Asp Lys Val Gly Ser Ala Leu
            340                 345                 350

Ile Ala Gln Ala Ala Gly Val Pro Thr Leu Ala Trp Ser Gly Ser His
```

-continued

```
                355                 360                 365
Val Glu Val Pro Leu Glu Cys Cys Leu Asp Ser Ile Pro Asp Glu Met
370                 375                 380

Tyr Arg Lys Ala Cys Val Thr Thr Glu Glu Ala Val Ala Ser Cys
385                 390                 395                 400

Gln Val Val Gly Tyr Pro Ala Met Ile Lys Ala Ser Trp Gly Gly Gly
                405                 410                 415

Gly Lys Gly Ile Arg Lys Val His Asn Asp Asp Glu Val Arg Thr Leu
                420                 425                 430

Phe Lys Gln Val Gln Gly Glu Val Pro Gly Ser Pro Ile Phe Ile Met
                435                 440                 445

Arg Leu Ala Ala Gln Ser Arg His Leu Glu Val Gln Leu Leu Cys Asp
450                 455                 460

Gln Tyr Gly Asn Val Ala Ala Leu His Ser Arg Asp Cys Ser Val Gln
465                 470                 475                 480

Arg Arg His Gln Lys Ile Ile Glu Gly Pro Val Thr Val Ala Pro
                485                 490                 495

Arg Glu Thr Val Lys Glu Leu Glu Gln Ala Ala Arg Arg Leu Ala Lys
                500                 505                 510

Ala Val Gly Tyr Val Gly Ala Ala Thr Val Glu Tyr Leu Tyr Ser Met
                515                 520                 525

Glu Thr Gly Glu Tyr Tyr Phe Leu Glu Leu Asn Pro Arg Leu Gln Val
530                 535                 540

Glu His Pro Val Thr Glu Trp Ile Ala Glu Val Asn Leu Pro Ala Ala
545                 550                 555                 560

Gln Val Ala Val Gly Met Gly Ile Pro Leu Trp Gln Ile Pro Glu Ile
                565                 570                 575

Arg Arg Phe Tyr Gly Met Asn His Gly Gly Gly Tyr Asp Leu Trp Arg
                580                 585                 590

Lys Thr Ala Ala Leu Ala Thr Pro Phe Asn Phe Asp Glu Val Asp Ser
                595                 600                 605

Lys Trp Pro Lys Gly His Cys Val Ala Val Arg Ile Thr Ser Glu Asp
610                 615                 620

Pro Asp Asp Gly Phe Lys Pro Thr Gly Gly Lys Val Lys Glu Ile Ser
625                 630                 635                 640

Phe Lys Ser Lys Pro Asn Val Trp Ala Tyr Phe Ser Val Lys Ser Gly
                645                 650                 655

Gly Gly Ile His Glu Phe Ala Asp Ser Gln Phe Gly His Val Phe Ala
                660                 665                 670

Tyr Gly Thr Thr Arg Ser Ala Ala Ile Thr Thr Met Ala Leu Ala Leu
                675                 680                 685

Lys Glu Val Gln Ile Arg Gly Glu Ile His Ser Asn Val Asp Tyr Thr
                690                 695                 700

Val Asp Leu Leu Asn Ala Ser Asp Phe Arg Glu Asn Lys Ile His Thr
705                 710                 715                 720

Gly Trp Leu Asp Thr Arg Ile Ala Met Arg Val Gln Ala Glu Arg Pro
                725                 730                 735

Pro Trp Tyr Ile Ser Val Val Gly Gly Ala Leu Tyr Lys Thr Val Thr
                740                 745                 750

Ala Asn Thr Ala Thr Val Ser Asp Tyr Val Gly Tyr Leu Thr Lys Gly
                755                 760                 765

Gln Ile Pro Pro Lys His Ile Ser Leu Val Tyr Thr Thr Val Ala Leu
                770                 775                 780
```

-continued

Asn Ile Asp Gly Lys Lys Tyr Thr Ile Asp Thr Val Arg Ser Gly His
785                 790                 795                 800

Gly Ser Tyr Arg Leu Arg Met Asn Gly Ser Thr Val Asp Ala Asn Val
            805                 810                 815

Gln Ile Leu Cys Asp Gly Gly Leu Leu Met Gln Leu Asp Gly Asn Ser
        820                 825                 830

His Val Ile Tyr Ala Glu Glu Ala Ser Gly Thr Arg Leu Leu Ile
    835                 840                 845

Asp Gly Lys Thr Cys Met Leu Gln Asn Asp His Asp Pro Ser Lys Leu
850                 855                 860

Leu Ala Glu Thr Pro Cys Lys Leu Leu Arg Phe Leu Val Ala Asp Gly
865                 870                 875                 880

Ala His Val Asp Ala Asp Val Pro Tyr Ala Glu Val Glu Val Met Lys
                885                 890                 895

Met Cys Met Pro Leu Leu Ser Pro Ala Ser Gly Val Ile His Val Val
            900                 905                 910

Met Ser Glu Gly Gln Ala Met Gln Ala Gly Asp Leu Ile Ala Arg Leu
        915                 920                 925

Asp Leu Asp Asp Pro Ser Ala Val Lys Arg Ala Glu Pro Phe Glu Asp
930                 935                 940

Thr Phe Pro Gln Met Gly Leu Pro Ile Ala Ala Ser Gly Gln Val His
945                 950                 955                 960

Lys Leu Cys Ala Ala Ser Leu Asn Ala Cys Arg Met Ile Leu Ala Gly
                965                 970                 975

Tyr Glu His Asp Ile Asp Lys Val Val Pro Glu Leu Val Tyr Cys Leu
            980                 985                 990

Asp Thr Pro Glu Leu Pro Phe Leu Gln Trp Glu Glu Leu Met Ser Val
        995                 1000                1005

Leu Ala Thr Arg Leu Pro Arg Asn Leu Lys Ser Glu Leu Glu Gly
    1010                1015                1020

Lys Tyr Glu Glu Tyr Lys Val Lys Phe Asp Ser Gly Ile Ile Asn
    1025                1030                1035

Asp Phe Pro Ala Asn Met Leu Arg Val Ile Ile Glu Glu Asn Leu
    1040                1045                1050

Ala Cys Gly Ser Glu Lys Lys Ala Thr Asn Glu Arg Leu Val
    1055                1060                1065

Glu Pro Leu Met Ser Leu Leu Lys Ser Tyr Glu Gly Gly Arg Glu
    1070                1075                1080

Ser His Ala His Phe Val Val Lys Ser Leu Phe Glu Glu Tyr Leu
    1085                1090                1095

Tyr Val Glu Glu Leu Phe Ser Asp Gly Ile Gln Ser Asp Val Ile
    1100                1105                1110

Glu Arg Leu Arg Leu Gln His Ser Lys Asp Leu Gln Lys Val Val
    1115                1120                1125

Asp Ile Val Leu Ser His Gln Ser Val Arg Asn Lys Thr Lys Leu
    1130                1135                1140

Ile Leu Lys Leu Met Glu Ser Leu Val Tyr Pro Asn Pro Ala Ala
    1145                1150                1155

Tyr Arg Asp Gln Leu Ile Arg Phe Ser Ser Leu Asn His Lys Ala
    1160                1165                1170

Tyr Tyr Lys Leu Ala Leu Lys Ala Ser Glu Leu Leu Glu Gln Thr
    1175                1180                1185

```
Lys Leu Ser Glu Leu Arg Ala Arg Ile Ala Arg Ser Leu Ser Glu
    1190                1195                1200

Leu Glu Met Phe Thr Glu Glu Ser Lys Gly Leu Ser Met His Lys
    1205                1210                1215

Arg Glu Ile Ala Ile Lys Glu Ser Met Glu Asp Leu Val Thr Ala
    1220                1225                1230

Pro Leu Pro Val Glu Asp Ala Leu Ile Ser Leu Phe Asp Cys Ser
    1235                1240                1245

Asp Thr Thr Val Gln Gln Arg Val Ile Glu Thr Tyr Ile Ala Arg
    1250                1255                1260

Leu Tyr Gln Pro His Leu Val Lys Asp Ser Ile Lys Met Lys Trp
    1265                1270                1275

Ile Glu Ser Gly Val Ile Ala Leu Trp Glu Phe Pro Glu Gly His
    1280                1285                1290

Phe Asp Ala Arg Asn Gly Gly Ala Val Leu Gly Asp Lys Arg Trp
    1295                1300                1305

Gly Ala Met Val Ile Val Lys Ser Leu Glu Ser Leu Ser Met Ala
    1310                1315                1320

Ile Arg Phe Ala Leu Lys Glu Thr Ser His Tyr Thr Ser Ser Glu
    1325                1330                1335

Gly Asn Met Met His Ile Ala Leu Leu Gly Ala Asp Asn Lys Met
    1340                1345                1350

His Ile Ile Gln Glu Ser Gly Asp Asp Ala Asp Arg Ile Ala Lys
    1355                1360                1365

Leu Pro Leu Ile Leu Lys Asp Asn Val Thr Asp Leu His Ala Ser
    1370                1375                1380

Gly Val Lys Thr Ile Ser Phe Ile Val Gln Arg Asp Glu Ala Arg
    1385                1390                1395

Met Thr Met Arg Arg Thr Phe Leu Trp Ser Asp Glu Lys Leu Ser
    1400                1405                1410

Tyr Glu Glu Glu Pro Ile Leu Arg His Val Glu Pro Pro Leu Ser
    1415                1420                1425

Ala Leu Leu Glu Leu Asp Lys Leu Lys Val Lys Gly Tyr Asn Glu
    1430                1435                1440

Met Lys Tyr Thr Pro Ser Arg Asp Arg Gln Trp His Ile Tyr Thr
    1445                1450                1455

Leu Arg Asn Thr Glu Asn Pro Lys Met Leu His Arg Val Phe Phe
    1460                1465                1470

Arg Thr Leu Val Arg Gln Pro Ser Val Ser Asn Lys Phe Ser Ser
    1475                1480                1485

Gly Gln Ile Gly Asp Met Glu Val Gly Ser Ala Glu Glu Pro Leu
    1490                1495                1500

Ser Phe Thr Ser Thr Ser Ile Leu Arg Ser Leu Met Thr Ala Ile
    1505                1510                1515

Glu Glu Leu Glu Leu His Ala Ile Arg Thr Gly His Ser His Met
    1520                1525                1530

Tyr Leu His Val Leu Lys Glu Gln Lys Leu Leu Asp Leu Val Pro
    1535                1540                1545

Val Ser Gly Asn Thr Val Leu Asp Val Gly Gln Asp Glu Ala Thr
    1550                1555                1560

Ala Tyr Ser Leu Leu Lys Glu Met Ala Met Lys Ile His Glu Leu
    1565                1570                1575

Val Gly Ala Arg Met His His Leu Ser Val Cys Gln Trp Glu Val
```

-continued

|  |  |  | 1580 |  |  |  | 1585 |  |  |  | 1590 |  |  |  |
| --- | --- | --- | --- | --- | --- | --- | --- | --- | --- | --- | --- | --- | --- | --- |
| Lys | Leu | Lys | Leu | Asp | Cys | Asp | Gly | Pro | Ala | Ser | Gly | Thr | Trp | Arg |
|  |  | 1595 |  |  |  | 1600 |  |  |  | 1605 |  |  |  |  |
| Ile | Val | Thr | Thr | Asn | Val | Thr | Ser | His | Thr | Cys | Thr | Val | Asp | Ile |
|  |  | 1610 |  |  |  | 1615 |  |  |  | 1620 |  |  |  |  |
| Tyr | Arg | Glu | Met | Glu | Asp | Lys | Glu | Ser | Arg | Lys | Leu | Val | Tyr | His |
|  |  | 1625 |  |  |  | 1630 |  |  |  | 1635 |  |  |  |  |
| Pro | Ala | Thr | Pro | Ala | Ala | Gly | Pro | Leu | His | Gly | Val | Ala | Leu | Asn |
|  |  | 1640 |  |  |  | 1645 |  |  |  | 1650 |  |  |  |  |
| Asn | Pro | Tyr | Gln | Pro | Leu | Ser | Val | Ile | Asp | Leu | Lys | Arg | Cys | Ser |
|  |  | 1655 |  |  |  | 1660 |  |  |  | 1665 |  |  |  |  |
| Ala | Arg | Asn | Asn | Arg | Thr | Thr | Tyr | Cys | Tyr | Asp | Phe | Pro | Leu | Ala |
|  |  | 1670 |  |  |  | 1675 |  |  |  | 1680 |  |  |  |  |
| Phe | Glu | Thr | Ala | Val | Arg | Lys | Ser | Trp | Ser | Ser | Ser | Thr | Ser | Gly |
|  |  | 1685 |  |  |  | 1690 |  |  |  | 1695 |  |  |  |  |
| Ala | Ser | Lys | Gly | Val | Glu | Asn | Ala | Gln | Cys | Tyr | Val | Lys | Ala | Thr |
|  |  | 1700 |  |  |  | 1705 |  |  |  | 1710 |  |  |  |  |
| Glu | Leu | Val | Phe | Ala | Asp | Lys | His | Gly | Ser | Trp | Gly | Thr | Pro | Leu |
|  |  | 1715 |  |  |  | 1720 |  |  |  | 1725 |  |  |  |  |
| Val | Gln | Met | Asp | Arg | Pro | Ala | Gly | Leu | Asn | Asp | Ile | Gly | Met | Val |
|  |  | 1730 |  |  |  | 1735 |  |  |  | 1740 |  |  |  |  |
| Ala | Trp | Thr | Leu | Lys | Met | Ser | Thr | Pro | Glu | Phe | Pro | Ser | Gly | Arg |
|  |  | 1745 |  |  |  | 1750 |  |  |  | 1755 |  |  |  |  |
| Glu | Ile | Ile | Val | Val | Ala | Asn | Asp | Ile | Thr | Phe | Arg | Ala | Gly | Ser |
|  |  | 1760 |  |  |  | 1765 |  |  |  | 1770 |  |  |  |  |
| Phe | Gly | Pro | Arg | Glu | Asp | Ala | Phe | Phe | Glu | Ala | Val | Thr | Asn | Leu |
|  |  | 1775 |  |  |  | 1780 |  |  |  | 1785 |  |  |  |  |
| Ala | Cys | Glu | Lys | Lys | Leu | Pro | Leu | Ile | Tyr | Leu | Ala | Ala | Asn | Ser |
|  |  | 1790 |  |  |  | 1795 |  |  |  | 1800 |  |  |  |  |
| Gly | Ala | Arg | Ile | Gly | Ile | Ala | Asp | Glu | Val | Lys | Ser | Cys | Phe | Arg |
|  |  | 1805 |  |  |  | 1810 |  |  |  | 1815 |  |  |  |  |
| Val | Gly | Trp | Ser | Asp | Asp | Gly | Ser | Pro | Glu | Arg | Gly | Phe | Gln | Tyr |
|  |  | 1820 |  |  |  | 1825 |  |  |  | 1830 |  |  |  |  |
| Ile | Tyr | Leu | Ser | Glu | Glu | Asp | Tyr | Ala | Arg | Ile | Gly | Thr | Ser | Val |
|  |  | 1835 |  |  |  | 1840 |  |  |  | 1845 |  |  |  |  |
| Ile | Ala | His | Lys | Met | Gln | Leu | Asp | Ser | Gly | Glu | Ile | Arg | Trp | Val |
|  |  | 1850 |  |  |  | 1855 |  |  |  | 1860 |  |  |  |  |
| Ile | Asp | Ser | Val | Val | Gly | Lys | Glu | Asp | Gly | Leu | Gly | Val | Glu | Asn |
|  |  | 1865 |  |  |  | 1870 |  |  |  | 1875 |  |  |  |  |
| Val | His | Gly | Ser | Ala | Ala | Ile | Ala | Ser | Ala | Tyr | Ser | Arg | Ala | Tyr |
|  |  | 1880 |  |  |  | 1885 |  |  |  | 1890 |  |  |  |  |
| Lys | Glu | Thr | Phe | Thr | Leu | Thr | Phe | Val | Thr | Gly | Arg | Thr | Val | Gly |
|  |  | 1895 |  |  |  | 1900 |  |  |  | 1905 |  |  |  |  |
| Ile | Gly | Ala | Tyr | Leu | Ala | Arg | Leu | Gly | Ile | Arg | Cys | Ile | Gln | Arg |
|  |  | 1910 |  |  |  | 1915 |  |  |  | 1920 |  |  |  |  |
| Leu | Asp | Gln | Pro | Ile | Ile | Leu | Thr | Gly | Tyr | Ser | Ala | Leu | Asn | Lys |
|  |  | 1925 |  |  |  | 1930 |  |  |  | 1935 |  |  |  |  |
| Leu | Leu | Gly | Arg | Glu | Val | Tyr | Ser | Ser | His | Met | Gln | Leu | Gly | Gly |
|  |  | 1940 |  |  |  | 1945 |  |  |  | 1950 |  |  |  |  |
| Pro | Lys | Ile | Met | Ala | Thr | Asn | Gly | Val | Val | His | Leu | Thr | Val | Ser |
|  |  | 1955 |  |  |  | 1960 |  |  |  | 1965 |  |  |  |  |
| Asp | Asp | Leu | Glu | Gly | Val | Ser | Asn | Ile | Leu | Arg | Trp | Leu | Ser | Tyr |
|  |  | 1970 |  |  |  | 1975 |  |  |  | 1980 |  |  |  |  |

```
Val Pro Ala Tyr Ile Gly Gly Pro Leu Pro Val Thr Thr Pro Leu
1985                1990                1995

Asp Pro Pro Asp Arg Pro Val Ala Tyr Ile Pro Glu Asn Ser Cys
    2000                2005                2010

Asp Pro Arg Ala Ala Ile Arg Gly Val Asp Asp Ser Gln Gly Lys
    2015                2020                2025

Trp Leu Gly Gly Met Phe Asp Lys Asp Ser Phe Val Glu Thr Phe
    2030                2035                2040

Glu Gly Trp Ala Lys Thr Val Val Thr Gly Arg Ala Lys Leu Gly
    2045                2050                2055

Gly Ile Pro Val Gly Val Ile Ala Val Glu Thr Gln Thr Met Met
    2060                2065                2070

Gln Thr Ile Pro Ala Asp Pro Gly Gln Leu Asp Ser Arg Glu Gln
    2075                2080                2085

Ser Val Pro Arg Ala Gly Gln Val Trp Phe Pro Asp Ser Ala Thr
    2090                2095                2100

Lys Thr Ala Gln Ala Leu Leu Asp Phe Asn Arg Glu Gly Leu Pro
    2105                2110                2115

Leu Phe Ile Leu Ala Asn Trp Arg Gly Phe Ser Gly Gly Gln Arg
    2120                2125                2130

Asp Leu Phe Glu Gly Ile Leu Gln Ala Gly Ser Thr Ile Val Glu
    2135                2140                2145

Asn Leu Arg Thr Tyr Asn Gln Pro Ala Phe Val Tyr Ile Pro Met
    2150                2155                2160

Ala Ala Glu Leu Arg Gly Gly Ala Trp Val Val Val Asp Ser Lys
    2165                2170                2175

Ile Asn Pro Asp Arg Ile Glu Cys Tyr Ala Glu Arg Thr Ala Lys
    2180                2185                2190

Gly Asn Val Leu Glu Pro Gln Gly Leu Ile Glu Ile Lys Phe Arg
    2195                2200                2205

Ser Glu Glu Leu Gln Asp Cys Met Ser Arg Leu Asp Pro Thr Leu
    2210                2215                2220

Ile Asp Leu Lys Ala Lys Leu Glu Val Ala Asn Lys Asn Gly Ser
    2225                2230                2235

Ala Asp Thr Lys Ser Leu Gln Glu Asn Ile Glu Ala Arg Thr Lys
    2240                2245                2250

Gln Leu Met Pro Leu Tyr Thr Gln Ile Ala Ile Arg Phe Ala Glu
    2255                2260                2265

Leu His Asp Thr Ser Leu Arg Met Ala Ala Lys Gly Val Ile Lys
    2270                2275                2280

Lys Val Val Asp Trp Glu Glu Ser Arg Ser Phe Phe Tyr Lys Arg
    2285                2290                2295

Leu Arg Arg Arg Ile Ser Glu Asp Val Leu Ala Lys Glu Ile Arg
    2300                2305                2310

Ala Val Ala Gly Glu Gln Phe Ser His Gln Pro Ala Ile Glu Leu
    2315                2320                2325

Ile Lys Lys Trp Tyr Ser Ala Ser His Ala Ala Glu Trp Asp Asp
    2330                2335                2340

Asp Asp Ala Phe Val Ala Trp Met Asp Asn Pro Glu Asn Tyr Lys
    2345                2350                2355

Asp Tyr Ile Gln Tyr Leu Lys Ala Gln Arg Val Ser Gln Ser Leu
    2360                2365                2370
```

-continued

Ser Ser Leu Ser Asp Ser Ser Asp Leu Gln Ala Leu Pro Gln
    2375            2380            2385

Gly Leu Ser Met Leu Leu Asp Lys Met Asp Pro Ser Arg Arg Ala
    2390            2395            2400

Gln Leu Val Glu Glu Ile Arg Lys Val Leu Gly
    2405            2410

<210> SEQ ID NO 3
<211> LENGTH: 2414
<212> TYPE: PRT
<213> ORGANISM: Artificial Sequence
<220> FEATURE:
<223> OTHER INFORMATION: mutant ACC

<400> SEQUENCE: 3

Met Pro Met Arg Pro Trp Glu Phe Ile Ile Leu Gly Arg Thr Ala Pro
1               5                   10                  15

Ile Ser Pro Pro Leu Gly Ile Ser Ala Phe Ser Arg Pro Leu Arg
            20                  25                  30

Leu Arg Leu Arg Leu Arg Leu Ala Ala Val Val Asp Ala Ala Arg Ile
            35                  40                  45

Gln Thr Pro Pro Arg Val Ala Phe Ser Ala Phe Phe Phe Phe
    50                  55                      60

Phe Phe Ser Glu Gly Leu Ser Arg Glu Gly Thr Ala Ala Arg Leu Pro
65                  70                  75                  80

Ala Leu Ile Tyr Arg Val Pro Phe Ile Pro Cys Leu Leu Gln Leu Gln
                85                  90                  95

Ile Arg Ala Pro His Ala Asp Pro Arg Pro Ala Gly Phe Ser Cys Ala
            100                 105                 110

His His Phe Leu Ala Leu Ala Gln Gly Leu Ser Ser Ser Leu Leu Ser
        115                 120                 125

Gly Thr Ile Ser His Ile Trp Gly Phe Ile Phe Ser Leu Tyr Gly Thr
    130                 135                 140

Thr His Leu Arg Asn Arg Ala Ile Leu Leu Phe Gly Leu Ala Gly Ile
145                 150                 155                 160

Ile Asp Leu Pro Asn Asp Ala Ala Ser Glu Val Asp Ile Ser His Gly
                165                 170                 175

Ser Glu Asp Pro Arg Gly Pro Thr Val Pro Gly Ser Tyr Gln Met Asn
            180                 185                 190

Gly Ile Ile Asn Glu Thr His Asn Gly Arg His Ala Ser Val Ser Lys
        195                 200                 205

Val Val Glu Phe Cys Thr Ala Leu Gly Gly Lys Thr Pro Ile His Ser
    210                 215                 220

Val Leu Val Ala Asn Asn Gly Met Ala Ala Lys Phe Met Arg Ser
225                 230                 235                 240

Val Arg Thr Trp Ala Asn Asp Thr Phe Gly Ser Glu Lys Ala Ile Gln
                245                 250                 255

Leu Ile Ala Met Ala Thr Pro Glu Asp Leu Arg Ile Asn Ala Glu His
            260                 265                 270

Ile Arg Ile Ala Asp Gln Phe Val Glu Val Pro Gly Gly Thr Asn Asn
        275                 280                 285

Asn Asn Tyr Ala Asn Val Gln Leu Ile Val Glu Ile Ala Glu Arg Thr
    290                 295                 300

Gly Val Ser Ala Val Trp Pro Gly Trp Gly His Ala Ser Glu Asn Pro
305                 310                 315                 320

```
Glu Leu Pro Asp Ala Leu Thr Ala Lys Gly Ile Val Phe Leu Gly Pro
            325                 330                 335

Pro Ala Ser Ser Met His Ala Leu Gly Asp Lys Val Gly Ser Ala Leu
        340                 345                 350

Ile Ala Gln Ala Ala Gly Val Pro Thr Leu Ala Trp Ser Gly Ser His
            355                 360                 365

Val Glu Val Pro Leu Glu Cys Cys Leu Asp Ser Ile Pro Asp Glu Met
370                 375                 380

Tyr Arg Lys Ala Cys Val Thr Thr Glu Glu Ala Val Ala Ser Cys
385                 390                 395                 400

Gln Val Val Gly Tyr Pro Ala Met Ile Lys Ala Ser Trp Gly Gly Gly
            405                 410                 415

Gly Lys Gly Ile Arg Lys Val His Asn Asp Asp Glu Val Arg Thr Leu
        420                 425                 430

Phe Lys Gln Val Gln Gly Glu Val Pro Gly Ser Pro Ile Phe Ile Met
            435                 440                 445

Arg Leu Ala Ala Gln Ser Arg His Leu Glu Val Gln Leu Leu Cys Asp
        450                 455                 460

Gln Tyr Gly Asn Val Ala Ala Leu His Ser Arg Asp Cys Ser Val Gln
465                 470                 475                 480

Arg Arg His Gln Lys Ile Ile Glu Glu Gly Pro Val Thr Val Ala Pro
            485                 490                 495

Arg Glu Thr Val Lys Glu Leu Glu Gln Ala Ala Arg Arg Leu Ala Lys
        500                 505                 510

Ala Val Gly Tyr Val Gly Ala Ala Thr Val Glu Tyr Leu Tyr Ser Met
            515                 520                 525

Glu Thr Gly Glu Tyr Tyr Phe Leu Glu Leu Asn Pro Arg Leu Gln Val
530                 535                 540

Glu His Pro Val Thr Glu Trp Ile Ala Glu Val Asn Leu Pro Ala Ala
545                 550                 555                 560

Gln Val Ala Val Gly Met Gly Ile Pro Leu Trp Gln Ile Pro Glu Ile
            565                 570                 575

Arg Arg Phe Tyr Gly Met Asn His Gly Gly Gly Tyr Asp Leu Trp Arg
        580                 585                 590

Lys Thr Ala Ala Leu Ala Thr Pro Phe Asn Phe Asp Glu Val Asp Ser
            595                 600                 605

Lys Trp Pro Lys Gly His Cys Val Ala Val Arg Ile Thr Ser Glu Asp
        610                 615                 620

Pro Asp Asp Gly Phe Lys Pro Thr Gly Gly Lys Val Lys Glu Ile Ser
625                 630                 635                 640

Phe Lys Ser Lys Pro Asn Val Trp Ala Tyr Phe Ser Val Lys Ser Gly
            645                 650                 655

Gly Gly Ile His Glu Phe Ala Asp Ser Gln Phe Gly His Val Phe Ala
        660                 665                 670

Tyr Gly Thr Thr Arg Ser Ala Ala Ile Thr Thr Met Ala Leu Ala Leu
            675                 680                 685

Lys Glu Val Gln Ile Arg Gly Glu Ile His Ser Asn Val Asp Tyr Thr
        690                 695                 700

Val Asp Leu Leu Asn Ala Ser Asp Phe Arg Glu Asn Lys Ile His Thr
705                 710                 715                 720

Gly Trp Leu Asp Thr Arg Ile Ala Met Arg Val Gln Ala Glu Arg Pro
            725                 730                 735

Pro Trp Tyr Ile Ser Val Val Gly Gly Ala Leu Tyr Lys Thr Val Thr
```

-continued

```
                740             745             750
Ala Asn Thr Ala Thr Val Ser Asp Tyr Val Gly Tyr Leu Thr Lys Gly
            755             760             765
Gln Ile Pro Pro Lys His Ile Ser Leu Val Tyr Thr Thr Val Ala Leu
        770             775             780
Asn Ile Asp Gly Lys Lys Tyr Thr Ile Asp Thr Val Arg Ser Gly His
785             790             795             800
Gly Ser Tyr Arg Leu Arg Met Asn Gly Ser Thr Val Asp Ala Asn Val
            805             810             815
Gln Ile Leu Cys Asp Gly Gly Leu Leu Met Gln Leu Asp Gly Asn Ser
            820             825             830
His Val Ile Tyr Ala Glu Glu Ala Ser Gly Thr Arg Leu Leu Ile
            835             840             845
Asp Gly Lys Thr Cys Met Leu Gln Asn Asp His Asp Pro Ser Lys Leu
            850             855             860
Leu Ala Glu Thr Pro Cys Lys Leu Leu Arg Phe Leu Val Ala Asp Gly
865             870             875             880
Ala His Val Asp Ala Asp Val Pro Tyr Ala Glu Val Glu Val Met Lys
            885             890             895
Met Cys Met Pro Leu Leu Ser Pro Ala Ser Gly Val Ile His Val Val
            900             905             910
Met Ser Glu Gly Gln Ala Met Gln Ala Gly Asp Leu Ile Ala Arg Leu
            915             920             925
Asp Leu Asp Asp Pro Ser Ala Val Lys Arg Ala Glu Pro Phe Glu Asp
            930             935             940
Thr Phe Pro Gln Met Gly Leu Pro Ile Ala Ala Ser Gly Gln Val His
945             950             955             960
Lys Leu Cys Ala Ala Ser Leu Asn Ala Cys Arg Met Ile Leu Ala Gly
            965             970             975
Tyr Glu His Asp Ile Asp Lys Val Val Pro Glu Leu Val Tyr Cys Leu
            980             985             990
Asp Thr Pro Glu Leu Pro Phe Leu  Gln Trp Glu Glu Leu  Met Ser Val
            995             1000            1005
Leu Ala  Thr Arg Leu Pro Arg  Asn Leu Lys Ser Glu  Leu Glu Gly
        1010            1015            1020
Lys Tyr Glu Glu Tyr Lys Val  Lys Phe Asp Ser Gly  Ile Ile Asn
        1025            1030            1035
Asp Phe  Pro Ala Asn Met Leu  Arg Val Ile Ile Glu  Glu Asn Leu
        1040            1045            1050
Ala Cys  Gly Ser Glu Lys Glu  Lys Ala Thr Asn Glu  Arg Leu Val
        1055            1060            1065
Glu Pro  Leu Met Ser Leu Leu  Lys Ser Tyr Glu Gly  Gly Arg Glu
        1070            1075            1080
Ser His  Ala His Phe Val Val  Lys Ser Leu Phe Glu  Glu Tyr Leu
        1085            1090            1095
Tyr Val  Glu Glu Leu Phe Ser  Asp Gly Ile Gln Ser  Asp Val Ile
        1100            1105            1110
Glu Arg  Leu Arg Leu Gln His  Ser Lys Asp Leu Gln  Lys Val Val
        1115            1120            1125
Asp Ile  Val Leu Ser His Gln  Ser Val Arg Asn Lys  Thr Lys Leu
        1130            1135            1140
Ile Leu  Lys Leu Met Glu Ser  Leu Val Tyr Pro Asn  Pro Ala Ala
        1145            1150            1155
```

```
Tyr Arg Asp Gln Leu Ile Arg Phe Ser Ser Leu Asn His Lys Ala
1160                1165                1170

Tyr Tyr Lys Leu Ala Leu Lys Ala Ser Glu Leu Leu Glu Gln Thr
1175                1180                1185

Lys Leu Ser Glu Leu Arg Ala Arg Ile Ala Arg Ser Leu Ser Glu
1190                1195                1200

Leu Glu Met Phe Thr Glu Glu Ser Lys Gly Leu Ser Met His Lys
1205                1210                1215

Arg Glu Ile Ala Ile Lys Glu Ser Met Glu Asp Leu Val Thr Ala
1220                1225                1230

Pro Leu Pro Val Glu Asp Ala Leu Ile Ser Leu Phe Asp Cys Ser
1235                1240                1245

Asp Thr Thr Val Gln Gln Arg Val Ile Glu Thr Tyr Ile Ala Arg
1250                1255                1260

Leu Tyr Gln Pro His Leu Val Lys Asp Ser Ile Lys Met Lys Trp
1265                1270                1275

Ile Glu Ser Gly Val Ile Ala Leu Trp Glu Phe Pro Glu Gly His
1280                1285                1290

Phe Asp Ala Arg Asn Gly Gly Ala Val Leu Gly Asp Lys Arg Trp
1295                1300                1305

Gly Ala Met Val Ile Val Lys Ser Leu Glu Ser Leu Ser Met Ala
1310                1315                1320

Ile Arg Phe Ala Leu Lys Glu Thr Ser His Tyr Thr Ser Ser Glu
1325                1330                1335

Gly Asn Met Met His Ile Ala Leu Leu Gly Ala Asp Asn Lys Met
1340                1345                1350

His Ile Ile Gln Glu Ser Gly Asp Asp Ala Asp Arg Ile Ala Lys
1355                1360                1365

Leu Pro Leu Ile Leu Lys Asp Asn Val Thr Asp Leu His Ala Ser
1370                1375                1380

Gly Val Lys Thr Ile Ser Phe Ile Val Gln Arg Asp Glu Ala Arg
1385                1390                1395

Met Thr Met Arg Arg Thr Phe Leu Trp Ser Asp Glu Lys Leu Ser
1400                1405                1410

Tyr Glu Glu Glu Pro Ile Leu Arg His Val Glu Pro Pro Leu Ser
1415                1420                1425

Ala Leu Leu Glu Leu Asp Lys Leu Lys Val Lys Gly Tyr Asn Glu
1430                1435                1440

Met Lys Tyr Thr Pro Ser Arg Asp Arg Gln Trp His Ile Tyr Thr
1445                1450                1455

Leu Arg Asn Thr Glu Asn Pro Lys Met Leu His Arg Val Phe Phe
1460                1465                1470

Arg Thr Leu Val Arg Gln Pro Ser Val Ser Asn Lys Phe Ser Ser
1475                1480                1485

Gly Gln Ile Gly Asp Met Glu Val Gly Ser Ala Glu Glu Pro Leu
1490                1495                1500

Ser Phe Thr Ser Thr Ser Ile Leu Arg Ser Leu Met Thr Ala Ile
1505                1510                1515

Glu Glu Leu Glu Leu His Ala Ile Arg Thr Gly His Ser His Met
1520                1525                1530

Tyr Leu His Val Leu Lys Glu Gln Lys Leu Leu Asp Leu Val Pro
1535                1540                1545
```

-continued

Val Ser Gly Asn Thr Val Leu Asp Val Gly Gln Asp Glu Ala Thr
1550                     1555                1560

Ala Tyr Ser Leu Leu Lys Glu Met Ala Met Lys Ile His Glu Leu
1565                     1570                1575

Val Gly Ala Arg Met His His Leu Ser Val Cys Gln Trp Glu Val
1580                     1585                1590

Lys Leu Lys Leu Asp Cys Asp Gly Pro Ala Ser Gly Thr Trp Arg
1595                     1600                1605

Ile Val Thr Thr Asn Val Thr Ser His Thr Cys Thr Val Asp Ile
1610                     1615                1620

Tyr Arg Glu Met Glu Asp Lys Glu Ser Arg Lys Leu Val Tyr His
1625                     1630                1635

Pro Ala Thr Pro Ala Ala Gly Pro Leu His Gly Val Ala Leu Asn
1640                     1645                1650

Asn Pro Tyr Gln Pro Leu Ser Val Ile Asp Leu Lys Arg Cys Ser
1655                     1660                1665

Ala Arg Asn Asn Arg Thr Thr Tyr Cys Tyr Asp Phe Pro Leu Ala
1670                     1675                1680

Phe Glu Thr Ala Val Arg Lys Ser Trp Ser Ser Thr Ser Gly
1685                     1690                1695

Ala Ser Lys Gly Val Glu Asn Ala Gln Cys Tyr Val Lys Ala Thr
1700                     1705                1710

Glu Leu Val Phe Ala Asp Lys His Gly Ser Trp Gly Thr Pro Leu
1715                     1720                1725

Val Gln Met Asp Arg Pro Ala Gly Leu Asn Asp Ile Gly Met Val
1730                     1735                1740

Ala Trp Thr Leu Lys Met Ser Thr Pro Glu Phe Pro Ser Gly Arg
1745                     1750                1755

Glu Ile Ile Val Val Ala Asn Asp Ile Thr Phe Arg Ala Gly Ser
1760                     1765                1770

Phe Gly Pro Arg Glu Asp Ala Phe Phe Glu Ala Val Thr Asn Leu
1775                     1780                1785

Ala Cys Glu Lys Lys Leu Pro Leu Ile Tyr Leu Ala Ala Asn Ser
1790                     1795                1800

Gly Ala Arg Ile Gly Ile Ala Asp Glu Val Lys Ser Cys Phe Arg
1805                     1810                1815

Val Gly Trp Ser Asp Asp Gly Ser Pro Glu Arg Gly Phe Gln Tyr
1820                     1825                1830

Ile Tyr Leu Ser Glu Glu Asp Tyr Ala Arg Ile Gly Thr Ser Val
1835                     1840                1845

Ile Ala His Lys Met Gln Leu Asp Ser Gly Glu Ile Arg Trp Val
1850                     1855                1860

Ile Asp Ser Val Val Gly Lys Glu Asp Gly Leu Gly Val Glu Asn
1865                     1870                1875

Ile His Gly Ser Ala Ala Ile Ala Ser Ala Tyr Ser Arg Ala Tyr
1880                     1885                1890

Lys Glu Thr Phe Thr Leu Thr Phe Val Thr Gly Arg Thr Val Gly
1895                     1900                1905

Ile Gly Ala Tyr Leu Ala Arg Leu Gly Ile Arg Cys Ile Gln Arg
1910                     1915                1920

Leu Asp Gln Pro Ile Ile Leu Thr Gly Tyr Ser Ala Leu Asn Lys
1925                     1930                1935

Leu Leu Gly Arg Glu Val Tyr Ser Ser His Met Gln Leu Gly Gly

-continued

```
                    1940                1945                1950
Pro Lys Ile Met Ala Thr Asn Gly Val Val His Leu Thr Val Ser
    1955                1960                1965

Asp Asp Leu Glu Gly Val Ser Asn Ile Leu Arg Trp Leu Ser Tyr
    1970                1975                1980

Val Pro Ala Tyr Ile Gly Gly Pro Leu Pro Val Thr Thr Pro Leu
    1985                1990                1995

Asp Pro Pro Asp Arg Pro Val Ala Tyr Ile Pro Glu Asn Ser Cys
    2000                2005                2010

Asp Pro Arg Ala Ala Ile Arg Gly Val Asp Asp Ser Gln Gly Lys
    2015                2020                2025

Trp Leu Gly Gly Met Phe Asp Lys Asp Ser Phe Val Glu Thr Phe
    2030                2035                2040

Glu Gly Trp Ala Lys Thr Val Val Thr Gly Arg Ala Lys Leu Gly
    2045                2050                2055

Gly Ile Pro Val Gly Val Ile Ala Val Glu Thr Gln Thr Met Met
    2060                2065                2070

Gln Thr Ile Pro Ala Asp Pro Gly Gln Leu Asp Ser Arg Glu Gln
    2075                2080                2085

Ser Val Pro Arg Ala Gly Gln Val Trp Phe Pro Asp Ser Ala Thr
    2090                2095                2100

Lys Thr Ala Gln Ala Leu Leu Asp Phe Asn Arg Glu Gly Leu Pro
    2105                2110                2115

Leu Phe Ile Leu Ala Asn Trp Arg Gly Phe Ser Gly Gly Gln Arg
    2120                2125                2130

Asp Leu Phe Glu Gly Ile Leu Gln Ala Gly Ser Thr Ile Val Glu
    2135                2140                2145

Asn Leu Arg Thr Tyr Asn Gln Pro Ala Phe Val Tyr Ile Pro Met
    2150                2155                2160

Ala Ala Glu Leu Arg Gly Gly Ala Trp Val Val Asp Ser Lys
    2165                2170                2175

Ile Asn Pro Asp Arg Ile Glu Arg Tyr Ala Glu Arg Thr Ala Lys
    2180                2185                2190

Gly Asn Val Leu Glu Pro Gln Gly Leu Ile Glu Ile Lys Phe Arg
    2195                2200                2205

Ser Glu Glu Leu Gln Asp Cys Met Ser Arg Leu Asp Pro Thr Leu
    2210                2215                2220

Ile Asp Leu Lys Ala Lys Leu Glu Val Ala Asn Lys Asn Gly Ser
    2225                2230                2235

Ala Asp Thr Lys Ser Leu Gln Glu Asn Ile Glu Ala Arg Thr Lys
    2240                2245                2250

Gln Leu Met Pro Leu Tyr Thr Gln Ile Ala Ile Arg Phe Ala Glu
    2255                2260                2265

Leu His Asp Thr Ser Leu Arg Met Ala Ala Lys Gly Val Ile Lys
    2270                2275                2280

Lys Val Val Asp Trp Glu Glu Ser Arg Ser Phe Phe Tyr Lys Arg
    2285                2290                2295

Leu Arg Arg Arg Ile Ser Glu Asp Val Leu Ala Lys Glu Ile Arg
    2300                2305                2310

Ala Val Ala Gly Glu Gln Phe Ser His Gln Pro Ala Ile Glu Leu
    2315                2320                2325

Ile Lys Lys Trp Tyr Ser Ala Ser His Ala Ala Glu Trp Asp Asp
    2330                2335                2340
```

-continued

Asp Asp Ala Phe Val Ala Trp Met Asp Asn Pro Glu Asn Tyr Lys
2345                2350                2355

Asp Tyr Ile Gln Tyr Leu Lys Ala Gln Arg Val Ser Gln Ser Leu
2360                2365                2370

Ser Ser Leu Ser Asp Ser Ser Asp Leu Gln Ala Leu Pro Gln
2375                2380                2385

Gly Leu Ser Met Leu Leu Asp Lys Met Asp Pro Ser Arg Arg Ala
2390                2395                2400

Gln Leu Val Glu Glu Ile Arg Lys Val Leu Gly
2405                2410

<210> SEQ ID NO 4
<211> LENGTH: 2414
<212> TYPE: PRT
<213> ORGANISM: Artificial Sequence
<220> FEATURE:
<223> OTHER INFORMATION: mutant ACC

<400> SEQUENCE: 4

Met Pro Met Arg Pro Trp Glu Phe Ile Ile Leu Gly Arg Thr Ala Pro
1               5                   10                  15

Ile Ser Pro Pro Leu Gly Ile Ser Ala Phe Ser Arg Pro Leu Arg
                20                  25                  30

Leu Arg Leu Arg Leu Arg Leu Ala Ala Val Val Asp Ala Ala Arg Ile
            35                  40                  45

Gln Thr Pro Pro Arg Val Ala Phe Ser Ala Phe Phe Phe Phe Phe
50                  55                  60

Phe Phe Ser Glu Gly Leu Ser Arg Glu Gly Thr Ala Ala Arg Leu Pro
65                  70                  75                  80

Ala Leu Ile Tyr Arg Val Pro Phe Ile Pro Cys Leu Leu Gln Leu Gln
                85                  90                  95

Ile Arg Ala Pro His Ala Asp Pro Arg Pro Ala Gly Phe Ser Cys Ala
            100                 105                 110

His His Phe Leu Ala Leu Ala Gln Gly Leu Ser Ser Ser Leu Leu Ser
        115                 120                 125

Gly Thr Ile Ser His Ile Trp Gly Phe Ile Phe Ser Leu Tyr Gly Thr
130                 135                 140

Thr His Leu Arg Asn Arg Ala Ile Leu Leu Phe Gly Leu Ala Gly Ile
145                 150                 155                 160

Ile Asp Leu Pro Asn Asp Ala Ala Ser Glu Val Asp Ile Ser His Gly
                165                 170                 175

Ser Glu Asp Pro Arg Gly Pro Thr Val Pro Gly Ser Tyr Gln Met Asn
            180                 185                 190

Gly Ile Ile Asn Glu Thr His Asn Gly Arg His Ala Ser Val Ser Lys
        195                 200                 205

Val Val Glu Phe Cys Thr Ala Leu Gly Gly Lys Thr Pro Ile His Ser
    210                 215                 220

Val Leu Val Ala Asn Asn Gly Met Ala Ala Ala Lys Phe Met Arg Ser
225                 230                 235                 240

Val Arg Thr Trp Ala Asn Asp Thr Phe Gly Ser Glu Lys Ala Ile Gln
                245                 250                 255

Leu Ile Ala Met Ala Thr Pro Glu Asp Leu Arg Ile Asn Ala Glu His
            260                 265                 270

Ile Arg Ile Ala Asp Gln Phe Val Glu Val Pro Gly Gly Thr Asn Asn
        275                 280                 285

```
Asn Asn Tyr Ala Asn Val Gln Leu Ile Val Glu Ile Ala Glu Arg Thr
            290                 295                 300

Gly Val Ser Ala Val Trp Pro Gly Trp Gly His Ala Ser Glu Asn Pro
305                 310                 315                 320

Glu Leu Pro Asp Ala Leu Thr Ala Lys Gly Ile Val Phe Leu Gly Pro
                325                 330                 335

Pro Ala Ser Ser Met His Ala Leu Gly Asp Lys Val Gly Ser Ala Leu
                340                 345                 350

Ile Ala Gln Ala Ala Gly Val Pro Thr Leu Ala Trp Ser Gly Ser His
            355                 360                 365

Val Glu Val Pro Leu Glu Cys Cys Leu Asp Ser Ile Pro Asp Glu Met
370                 375                 380

Tyr Arg Lys Ala Cys Val Thr Thr Glu Glu Ala Val Ala Ser Cys
385                 390                 395                 400

Gln Val Val Gly Tyr Pro Ala Met Ile Lys Ala Ser Trp Gly Gly Gly
                405                 410                 415

Gly Lys Gly Ile Arg Lys Val His Asn Asp Asp Glu Val Arg Thr Leu
            420                 425                 430

Phe Lys Gln Val Gln Gly Glu Val Pro Gly Ser Pro Ile Phe Ile Met
            435                 440                 445

Arg Leu Ala Ala Gln Ser Arg His Leu Glu Val Gln Leu Leu Cys Asp
450                 455                 460

Gln Tyr Gly Asn Val Ala Ala Leu His Ser Arg Asp Cys Ser Val Gln
465                 470                 475                 480

Arg Arg His Gln Lys Ile Ile Glu Glu Gly Pro Val Thr Val Ala Pro
                485                 490                 495

Arg Glu Thr Val Lys Glu Leu Glu Gln Ala Ala Arg Arg Leu Ala Lys
                500                 505                 510

Ala Val Gly Tyr Val Gly Ala Ala Thr Val Glu Tyr Leu Tyr Ser Met
            515                 520                 525

Glu Thr Gly Glu Tyr Tyr Phe Leu Glu Leu Asn Pro Arg Leu Gln Val
530                 535                 540

Glu His Pro Val Thr Glu Trp Ile Ala Glu Val Asn Leu Pro Ala Ala
545                 550                 555                 560

Gln Val Ala Val Gly Met Gly Ile Pro Leu Trp Gln Ile Pro Glu Ile
                565                 570                 575

Arg Arg Phe Tyr Gly Met Asn His Gly Gly Gly Tyr Asp Leu Trp Arg
                580                 585                 590

Lys Thr Ala Ala Leu Ala Thr Pro Phe Asn Phe Asp Glu Val Asp Ser
            595                 600                 605

Lys Trp Pro Lys Gly His Cys Val Ala Val Arg Ile Thr Ser Glu Asp
            610                 615                 620

Pro Asp Asp Gly Phe Lys Pro Thr Gly Gly Lys Val Lys Glu Ile Ser
625                 630                 635                 640

Phe Lys Ser Lys Pro Asn Val Trp Ala Tyr Phe Ser Val Lys Ser Gly
                645                 650                 655

Gly Gly Ile His Glu Phe Ala Asp Ser Gln Phe Gly His Val Phe Ala
                660                 665                 670

Tyr Gly Thr Thr Arg Ser Ala Ala Ile Thr Thr Met Ala Leu Ala Leu
            675                 680                 685

Lys Glu Val Gln Ile Arg Gly Glu Ile His Ser Asn Val Asp Tyr Thr
690                 695                 700
```

```
Val Asp Leu Leu Asn Ala Ser Asp Phe Arg Glu Asn Lys Ile His Thr
705                 710                 715                 720

Gly Trp Leu Asp Thr Arg Ile Ala Met Arg Val Gln Ala Glu Arg Pro
            725                 730                 735

Pro Trp Tyr Ile Ser Val Val Gly Gly Ala Leu Tyr Lys Thr Val Thr
                740                 745                 750

Ala Asn Thr Ala Thr Val Ser Asp Tyr Val Gly Tyr Leu Thr Lys Gly
            755                 760                 765

Gln Ile Pro Pro Lys His Ile Ser Leu Val Tyr Thr Thr Val Ala Leu
770                 775                 780

Asn Ile Asp Gly Lys Lys Tyr Thr Ile Asp Thr Val Arg Ser Gly His
785                 790                 795                 800

Gly Ser Tyr Arg Leu Arg Met Asn Gly Ser Thr Val Asp Ala Asn Val
            805                 810                 815

Gln Ile Leu Cys Asp Gly Gly Leu Leu Met Gln Leu Asp Gly Asn Ser
                820                 825                 830

His Val Ile Tyr Ala Glu Glu Ala Ser Gly Thr Arg Leu Leu Ile
            835                 840                 845

Asp Gly Lys Thr Cys Met Leu Gln Asn Asp His Asp Pro Ser Lys Leu
850                 855                 860

Leu Ala Glu Thr Pro Cys Lys Leu Leu Arg Phe Leu Val Ala Asp Gly
865                 870                 875                 880

Ala His Val Asp Ala Asp Val Pro Tyr Ala Glu Val Glu Val Met Lys
            885                 890                 895

Met Cys Met Pro Leu Leu Ser Pro Ala Ser Gly Val Ile His Val Val
                900                 905                 910

Met Ser Glu Gly Gln Ala Met Gln Ala Gly Asp Leu Ile Ala Arg Leu
            915                 920                 925

Asp Leu Asp Asp Pro Ser Ala Val Lys Arg Ala Glu Pro Phe Glu Asp
930                 935                 940

Thr Phe Pro Gln Met Gly Leu Pro Ile Ala Ala Ser Gly Gln Val His
945                 950                 955                 960

Lys Leu Cys Ala Ala Ser Leu Asn Ala Cys Arg Met Ile Leu Ala Gly
            965                 970                 975

Tyr Glu His Asp Ile Asp Lys Val Val Pro Glu Leu Val Tyr Cys Leu
                980                 985                 990

Asp Thr Pro Glu Leu Pro Phe Leu Gln Trp Glu Glu Leu Met Ser Val
            995                 1000                1005

Leu Ala Thr Arg Leu Pro Arg Asn Leu Lys Ser Glu Leu Glu Gly
    1010                1015                1020

Lys Tyr Glu Glu Tyr Lys Val Lys Phe Asp Ser Gly Ile Ile Asn
    1025                1030                1035

Asp Phe Pro Ala Asn Met Leu Arg Val Ile Glu Glu Asn Leu
    1040                1045                1050

Ala Cys Gly Ser Glu Lys Glu Lys Ala Thr Asn Glu Arg Leu Val
    1055                1060                1065

Glu Pro Leu Met Ser Leu Leu Lys Ser Tyr Glu Gly Gly Arg Glu
    1070                1075                1080

Ser His Ala His Phe Val Val Lys Ser Leu Phe Glu Glu Tyr Leu
    1085                1090                1095

Tyr Val Glu Glu Leu Phe Ser Asp Gly Ile Gln Ser Asp Val Ile
    1100                1105                1110

Glu Arg Leu Arg Leu Gln His Ser Lys Asp Leu Gln Lys Val Val
```

-continued

```
                1115                1120                1125

Asp Ile Val Leu Ser His Gln Ser Val Arg Asn Lys Thr Lys Leu
                1130                1135                1140

Ile Leu Lys Leu Met Glu Ser Leu Val Tyr Pro Asn Pro Ala Ala
                1145                1150                1155

Tyr Arg Asp Gln Leu Ile Arg Phe Ser Ser Leu Asn His Lys Ala
                1160                1165                1170

Tyr Tyr Lys Leu Ala Leu Lys Ala Ser Glu Leu Leu Glu Gln Thr
                1175                1180                1185

Lys Leu Ser Glu Leu Arg Ala Arg Ile Ala Arg Ser Leu Ser Glu
                1190                1195                1200

Leu Glu Met Phe Thr Glu Glu Ser Lys Gly Leu Ser Met His Lys
                1205                1210                1215

Arg Glu Ile Ala Ile Lys Glu Ser Met Glu Asp Leu Val Thr Ala
                1220                1225                1230

Pro Leu Pro Val Glu Asp Ala Leu Ile Ser Leu Phe Asp Cys Ser
                1235                1240                1245

Asp Thr Thr Val Gln Gln Arg Val Ile Glu Thr Tyr Ile Ala Arg
                1250                1255                1260

Leu Tyr Gln Pro His Leu Val Lys Asp Ser Ile Lys Met Lys Trp
                1265                1270                1275

Ile Glu Ser Gly Val Ile Ala Leu Trp Glu Phe Pro Glu Gly His
                1280                1285                1290

Phe Asp Ala Arg Asn Gly Gly Ala Val Leu Gly Asp Lys Arg Trp
                1295                1300                1305

Gly Ala Met Val Ile Val Lys Ser Leu Glu Ser Leu Ser Met Ala
                1310                1315                1320

Ile Arg Phe Ala Leu Lys Glu Thr Ser His Tyr Thr Ser Ser Glu
                1325                1330                1335

Gly Asn Met Met His Ile Ala Leu Leu Gly Ala Asp Asn Lys Met
                1340                1345                1350

His Ile Ile Gln Glu Ser Gly Asp Asp Ala Asp Arg Ile Ala Lys
                1355                1360                1365

Leu Pro Leu Ile Leu Lys Asp Asn Val Thr Asp Leu His Ala Ser
                1370                1375                1380

Gly Val Lys Thr Ile Ser Phe Ile Val Gln Arg Asp Glu Ala Arg
                1385                1390                1395

Met Thr Met Arg Arg Thr Phe Leu Trp Ser Asp Glu Lys Leu Ser
                1400                1405                1410

Tyr Glu Glu Glu Pro Ile Leu Arg His Val Glu Pro Pro Leu Ser
                1415                1420                1425

Ala Leu Leu Glu Leu Asp Lys Leu Lys Val Lys Gly Tyr Asn Glu
                1430                1435                1440

Met Lys Tyr Thr Pro Ser Arg Asp Arg Gln Trp His Ile Tyr Thr
                1445                1450                1455

Leu Arg Asn Thr Glu Asn Pro Lys Met Leu His Arg Val Phe Phe
                1460                1465                1470

Arg Thr Leu Val Arg Gln Pro Ser Val Ser Asn Lys Phe Ser Ser
                1475                1480                1485

Gly Gln Ile Gly Asp Met Glu Val Gly Ser Ala Glu Glu Pro Leu
                1490                1495                1500

Ser Phe Thr Ser Thr Ser Ile Leu Arg Ser Leu Met Thr Ala Ile
                1505                1510                1515
```

-continued

```
Glu Glu Leu Glu Leu His Ala Ile Arg Thr Gly His Ser His Met
1520                1525                1530

Tyr Leu His Val Leu Lys Glu Gln Lys Leu Leu Asp Leu Val Pro
1535                1540                1545

Val Ser Gly Asn Thr Val Leu Asp Val Gly Gln Asp Glu Ala Thr
1550                1555                1560

Ala Tyr Ser Leu Leu Lys Glu Met Ala Met Lys Ile His Glu Leu
1565                1570                1575

Val Gly Ala Arg Met His His Leu Ser Val Cys Gln Trp Glu Val
1580                1585                1590

Lys Leu Lys Leu Asp Cys Asp Gly Pro Ala Ser Gly Thr Trp Arg
1595                1600                1605

Ile Val Thr Thr Asn Val Thr Ser His Thr Cys Thr Val Asp Ile
1610                1615                1620

Tyr Arg Glu Met Glu Asp Lys Glu Ser Arg Lys Leu Val Tyr His
1625                1630                1635

Pro Ala Thr Pro Ala Ala Gly Pro Leu His Gly Val Ala Leu Asn
1640                1645                1650

Asn Pro Tyr Gln Pro Leu Ser Val Ile Asp Leu Lys Arg Cys Ser
1655                1660                1665

Ala Arg Asn Asn Arg Thr Thr Tyr Cys Tyr Asp Phe Pro Leu Ala
1670                1675                1680

Phe Glu Thr Ala Val Arg Lys Ser Trp Ser Ser Ser Thr Ser Gly
1685                1690                1695

Ala Ser Lys Gly Val Glu Asn Ala Gln Cys Tyr Val Lys Ala Thr
1700                1705                1710

Glu Leu Val Phe Ala Asp Lys His Gly Ser Trp Gly Thr Pro Leu
1715                1720                1725

Val Gln Met Asp Arg Pro Ala Gly Leu Asn Asp Ile Gly Met Val
1730                1735                1740

Ala Trp Thr Leu Lys Met Ser Thr Pro Glu Phe Pro Ser Gly Arg
1745                1750                1755

Glu Ile Ile Val Val Ala Asn Asp Ile Thr Phe Arg Ala Gly Ser
1760                1765                1770

Phe Gly Pro Arg Glu Asp Ala Phe Phe Glu Ala Val Thr Asn Leu
1775                1780                1785

Ala Cys Glu Lys Lys Leu Pro Leu Ile Tyr Leu Ala Ala Asn Ser
1790                1795                1800

Gly Ala Arg Ile Gly Ile Ala Asp Glu Val Lys Ser Cys Phe Arg
1805                1810                1815

Val Gly Trp Ser Asp Asp Gly Ser Pro Glu Arg Gly Phe Gln Tyr
1820                1825                1830

Ile Tyr Leu Ser Glu Glu Asp Tyr Ala Arg Ile Gly Thr Ser Val
1835                1840                1845

Ile Ala His Lys Met Gln Leu Asp Ser Gly Glu Ile Arg Trp Val
1850                1855                1860

Ile Asp Ser Val Val Gly Lys Glu Asp Gly Leu Gly Val Glu Asn
1865                1870                1875

Val His Gly Ser Ala Ala Ile Ala Ser Ala Tyr Ser Arg Ala Tyr
1880                1885                1890

Lys Glu Thr Phe Thr Leu Thr Phe Val Thr Gly Arg Thr Val Gly
1895                1900                1905
```

-continued

```
Ile Gly Ala Tyr Leu Ala Arg Leu Gly Ile Arg Cys Ile Gln Arg
1910                1915                1920

Leu Asp Gln Pro Ile Ile Leu Thr Gly Tyr Ser Ala Leu Asn Lys
1925                1930                1935

Leu Leu Gly Arg Glu Val Tyr Ser Ser His Met Gln Leu Gly Gly
1940                1945                1950

Pro Lys Ile Met Ala Thr Asn Gly Val Val His Leu Thr Val Ser
1955                1960                1965

Asp Asp Leu Glu Gly Val Ser Asn Ile Leu Arg Trp Leu Ser Tyr
1970                1975                1980

Val Pro Ala Tyr Ile Gly Gly Pro Leu Pro Val Thr Thr Pro Leu
1985                1990                1995

Asp Pro Pro Asp Arg Pro Val Ala Tyr Ile Pro Glu Asn Ser Cys
2000                2005                2010

Asp Pro Arg Ala Ala Ile Arg Gly Val Asp Asp Ser Gln Gly Lys
2015                2020                2025

Trp Leu Gly Gly Met Phe Asp Lys Asp Ser Phe Val Glu Thr Phe
2030                2035                2040

Glu Gly Trp Ala Lys Thr Val Val Thr Gly Arg Ala Lys Leu Gly
2045                2050                2055

Gly Ile Pro Val Gly Val Ile Ala Val Glu Thr Gln Thr Met Met
2060                2065                2070

Gln Thr Ile Pro Ala Asp Pro Gly Gln Leu Asp Ser Arg Glu Gln
2075                2080                2085

Ser Val Pro Arg Ala Gly Gln Val Trp Phe Pro Asp Ser Ala Thr
2090                2095                2100

Lys Thr Ala Gln Ala Leu Leu Asp Phe Asn Arg Glu Gly Leu Pro
2105                2110                2115

Leu Phe Ile Leu Ala Asn Trp Arg Gly Phe Ser Gly Gly Gln Arg
2120                2125                2130

Asp Leu Phe Glu Gly Ile Leu Gln Ala Gly Ser Thr Ile Val Glu
2135                2140                2145

Asn Leu Arg Thr Tyr Asn Gln Pro Ala Phe Val Tyr Ile Pro Met
2150                2155                2160

Ala Ala Glu Leu Arg Gly Gly Ala Trp Val Val Val Asp Ser Lys
2165                2170                2175

Ile Asn Pro Asp Arg Ile Glu Arg Tyr Ala Glu Arg Thr Ala Lys
2180                2185                2190

Gly Asn Val Leu Glu Pro Gln Gly Leu Ile Glu Ile Lys Phe Arg
2195                2200                2205

Ser Glu Glu Leu Gln Asp Cys Met Ser Arg Leu Asp Pro Thr Leu
2210                2215                2220

Ile Asp Leu Lys Ala Lys Leu Glu Val Ala Asn Lys Asn Gly Ser
2225                2230                2235

Ala Asp Thr Lys Ser Leu Gln Glu Asn Ile Glu Ala Arg Thr Lys
2240                2245                2250

Gln Leu Met Pro Leu Tyr Thr Gln Ile Ala Ile Arg Phe Ala Glu
2255                2260                2265

Leu His Asp Thr Ser Leu Arg Met Ala Ala Lys Gly Val Ile Lys
2270                2275                2280

Lys Val Val Asp Trp Glu Glu Ser Arg Ser Phe Phe Tyr Lys Arg
2285                2290                2295

Leu Arg Arg Arg Ile Ser Glu Asp Val Leu Ala Lys Glu Ile Arg
```

|     |     |     |     |     |     |     |     |     |     |
|-----|-----|-----|-----|-----|-----|-----|-----|-----|-----|
| 2300 | | | | 2305 | | | | 2310 | |

Ala Val Ala Gly Glu Gln Phe Ser His Gln Pro Ala Ile Glu Leu
      2315                    2320                    2325

Ile Lys Lys Trp Tyr Ser Ala Ser His Ala Ala Glu Trp Asp Asp
      2330                    2335                    2340

Asp Asp Ala Phe Val Ala Trp Met Asp Asn Pro Glu Asn Tyr Lys
      2345                    2350                    2355

Asp Tyr Ile Gln Tyr Leu Lys Ala Gln Arg Val Ser Gln Ser Leu
      2360                    2365                    2370

Ser Ser Leu Ser Asp Ser Ser Asp Leu Gln Ala Leu Pro Gln
      2375                    2380                    2385

Gly Leu Ser Met Leu Leu Asp Lys Met Asp Pro Ser Arg Arg Ala
      2390                    2395                    2400

Gln Leu Val Glu Glu Ile Arg Lys Val Leu Gly
      2405                    2410

<210> SEQ ID NO 5
<211> LENGTH: 13931
<212> TYPE: DNA
<213> ORGANISM: Artificial Sequence
<220> FEATURE:
<223> OTHER INFORMATION: mutant ACC

<400> SEQUENCE: 5

```
atgccgatgc ggccgtggga atttattatt ttaggccgca cagcccccat ctctccccca        60
cccctcggga tatccgcctt ctcccgcccg ctccgcctcc gctccgcct ccgcctcgcc        120
gccgttgtcg acgccgcaag gatccaaacg ccgccccgcg tcgccttctc cgccttcttc       180
ttcttcttct tcttcttctc cgagggtctc tctcggaag gtacagctgc ccgcctccct        240
gctcttattt atcgcgtgcc gttcattccg tgccttctcc agctccagat ccgcgcgccg       300
cacgccgatc cgcgcccggc cggtgagtcc gccgcgggtt ccgccattg ctgccgtttc        360
tgcgctgcta gggggaggtt tagatgtggg tggtgggagc cgcgtgctgt tgtctgggat       420
gggagagaga gggtttaagg gtgggtgccg gatgcggatg ctcccgcccg gttttggtc        480
ctgcttgtgg actggcgagg ggctaggggt tgagttgtag ggattcggga tggaaatgga       540
ctggggagct cggatgggga ggtaatgcca cgccggtgaa atgcagctcg ctgttgttgg       600
ttctggttaa tgcctgggtg ttgctggcta tgttactatg ttgcatgcct acgcagata        660
ctgccatgtg ccatttttgcg tgattgtgat attggtttga ggttttagct gcgctcatca      720
tttcctcgcg ttggctcagg gtttaagctc ctctttgtta agtgggacgg tatgcatatg       780
cattgtgttc ttttaggttt aaattctggt tacggtgcca cacaacaagt cgtagatgct       840
cattcttgtt ctttcatgg ggcttatgga attgatggca catggcacac ctttctcctt        900
tttccgtcat gcatgttagt gccatattgt ctacgcaaaa aagaatattc tgcatatttg       960
tttactcact atttttttcc aagagaattg ggttttgcca tgcttcaaaa ggaacatttc      1020
aagctgaaaa agttctcccg atatggaatt agctttagag ttcaggggaa aaaatatgtt      1080
gttgctttgt gcttgtcaag taaccacagt tgcacaggtt ttgactgacc tcatgctact      1140
tgacattatt caccatgata aagttttacc tttgtttttt tcctttcac taggaacaga       1200
acgaattgtt tgcataacca atttgtagat ttgacatggg gaaatagcat aactgaatat      1260
atctcaacct attactaggc aaaataagaa atgaacctaa gcttaacag gtttgcatca       1320
aattatcctg tgcaaaatga acaaaggtgg cacacaatgt acaagcttgc atttcatttt      1380
```

```
tggatcctca aacgtcttaa agactttgc ataaagtatt tgatgagtaa cgagctggaa    1440
ctaatcattc ttatatattt tcatctgtca gatttcacac atctggggat ttatcttctc    1500
tttgtatggc actacacatt tgagaaaccg tgcaattcta ctgtttggtc agcaggacaa    1560
caatgacatc cacacatgtg gcgacattgg gagttggtgc ccaggcacct cctcgtcacc    1620
agaaaaagtc agctggcact gcatttgtat catctgggtc atcaagaccc tcataccgaa    1680
agaatggtca gcgtactcgg tcacttaggg aagaaagcaa tggaggagtg tctgattcca    1740
aaaagcttaa ccactctatt cgccaaggtg accactagct actttacata tgctataatt    1800
tgtgccaaac ataaacatgc aatggctgct attatttaaa cgttaatgtt gaaatagctg    1860
ctataggata cagcaaaaat atataattga ctgggcaaga tgcaacaatt gttttttcact   1920 aaagttagtt atcttttgct gtaaaagaca actgtttttt acataaaatg gtattaataa    1980
ccttgtaata ttcaatgcaa catgttctca agtaaaaaaa aacattgcct ggttgtataa    2040
gcaaatgtgt cgttgtagac atcttattaa acctttttgt gatatctatt accgtaggga    2100
acaggggagc tgtttaaatc tgttatcata gagtaatatg agaaaagtgg attgtgcgac    2160
tttggcatgt atacctgctc aatttcaaat atatgtctat gtgcaggtct tgctggcatc    2220
attgacctcc caaatgacgc agcttcagaa gttgatattt cacagtaagg actttatatt    2280
ttataataat tattatataa ttttctgaca tgttttgaga acctcaaaac atgtgattgc    2340
accttccttt tttatgtctg gttcagaaac tgataagttt tgacagtgtt taggatggat    2400
ctttgatgcg cacagtgctt tctaatgttt tcattttga agtaatgtt ttaggaagaa     2460 atatctgatt aaatttatac tttatcttta caaaagtcaa atgcgttctg tatcaattgc    2520
ggtttgtaat atggcaagaa catgctttca gaatttgttc atacaatgct ttctttctat    2580
tattatgtag aacaaatacc taatactttg ttcacctttt atagtggaca cctctcacag    2640 cttttttcagt aagtgatgca attttgtaca tttgtaagat gtgttccaga aacctttttct  2700 cctgcaattc taatgtaccc actcaaactg gtatcaccaa agatctccat ctgattgaaa    2760
aaaagctgcg tgaagtatgc ttatttatgc taaccataca tgatttatac tgttttatag    2820
tacaatgctt atttatgcta accatacata attttattct gttttctagt acattatttg    2880
tgcccctgac cataaatgat cctttcttttt acagtggttc cgaagatccc aggggggccta  2940 cggtcccagg ttcctaccaa atgaatggga ttatcaatga acacataat gggaggcatg     3000 cttcagtctc caaggttgtt gagttttgta cggcacttgg tggcaaaaca ccaattcaca    3060
gtgtattagt ggccaacaat ggaatggcag cagctaagtt catgcggagt gtccgaacat    3120
gggctaatga tacttttgga tcagagaagg caattcagct gatagctatg caactccgg     3180 aggatctgag gataaatgca gagcacatca gaattgccga tcaatttgta gaggtacctg    3240
gtggaacaaa caacaacaac tatgcaaatg tccaactcat agtggaggtt agttcagctc    3300
atccctcaac acaacatttt cgtttctatt taagttaggg aaaaatctct acgaccctcc    3360
aatttctgaa catccaattt tcaccatcaa ctgcaatcac agatagcaga gagaacaggt    3420
gtttctgctg tttggcctgg ttggggtcat gcatctgaga atcctgaact tccagatgcg    3480
ctgactgcaa aaggaattgt ttttcttggg ccaccagcat catcaatgca tgcattagga    3540
gacaaggttg gctcagctct cattgctcaa gcagctggag ttccaacact gcttggagt     3600 ggatcacatg tgagccttgt cttctctttt ttagcttatc atcttatctt ttcggtgatg    3660
cattatccca atgacactaa accataggtg gaagttcctc tggagtgttg cttggactca    3720
atacctgatg agatgtatag aaaagcttgt gttactacca cagaggaagc agttgcaagt    3780
```

```
tgtcaggtgg ttggttatcc tgccatgatt aaggcatctt ggggtggtgg tggtaaagga    3840
ataaggaagg tttgttcttc ttgtagttat caagagattg tttggattgc aagtgtttag    3900
tgcccatagt taactctggt cttttctaaca tgagtaactc aactttcttg caggttcata    3960
atgatgatga ggttaggaca ttatttaagc aagttcaagg cgaagtacct ggttccccaa    4020
tatttatcat gaggctagct gctcaggtgg ggcctttat ggaagttaca ccttttccct     4080
taatgttgag ttattccgga gttattatgg ttatgttctg tatgtttgat ctgtaaatta    4140
ttgaaattca cctccattgg ttctccagat tagcagacct acaattctac atatggttta    4200
tactttataa atactaggat ttagggatct tcatatagtt tatacatggt atttagattt    4260
catttgtaac cctattgaag acatcctgat tgttgtctta tgtagagtcg acatcttgaa    4320
gttcagttgc tttgtgatca atatggcaac gtagcagcac ttcacagtcg agattgcagt    4380
gtacaacggc gacaccaaaa ggtctgctgt ctcagttaaa tcacccctct gaatgatcta    4440
cttcttgcct gctgcgttgg tcagaggaat aatggttgta ttctactgaa cagataatcg    4500
aggaaggacc agttactgtt gctcctcgtg agactgtgaa agagcttgag caggcagcac    4560
ggaggcttgc taaagctgtg ggttatgttg gtgctgctac tgttgaatac ctttacagca    4620
tggaaactgg tgaatattat tttctggaac ttaatccacg gctacaggtc ggctcctttg    4680
acattcttca ggaattaatt tctgttgacc acatgattta cattgtcaaa tggtctcaca    4740
ggttgagcat cctgtcactg agtggatagc tgaagtaaat ttgcctgcgg ctcaagttgc    4800
tgttggaatg gtatacccc tttggcagat tccaggtaat gcttcttcat ttagttcctg     4860
ctctttgtta attgaatgag ctcttataca gaccatgaga cacattctac tgttaattca    4920
tagtatcccc tgacttgtta gtgttagaga tacagagatg tatcacaaat tcattgtatc    4980
tcctcaagga ctgtaaaaat cctataatta aatttctgaa aatttgttct tttaagcaga    5040
aaaaaaatct ctaaattatc tccctgtata cagagatcag gcgcttctac ggaatgaacc    5100
atggaggagg ctatgacctt tggaggaaaa cagcagctct agcgactcca tttaactttg    5160
atgaagtaga ttctaaatgg ccaaaaggcc actgcgtagc tgttagaata actagcgagg    5220
atccagatga tgggtttaag cctactggtg gaaaagtaaa ggtgcggttt cctgatgtta    5280
ggtgtatgaa ttgaacacat tgctatattg cagctagtga aatgactgga tcatggttct    5340
cttattttca ggagataagt ttcaagagta aaccaaatgt ttgggcctat ttctcagtaa    5400
aggtagtcct caatattgtt gcactgccac attatttgag ttgtcctaac aattgtgctg    5460
caattgttag ttttcaacta tttgttgttc tgtttggttg actggtaccc tctcttttgca   5520 gtctggtgga ggcatccatg aattcgctga ttctcagttc ggtatgtaaa gttaaaagag    5580
taatattgtc tttgctattt atgtttgtcc tcacttttaa aagatattgc cttccattac    5640
aggacatgtt tttgcgtatg gaactactag atcggcagca ataactacca tggctcttgc    5700
actaaaagag gttcaaattc gtggagaaat tcattcaaac gtagactaca cagttgacct    5760
attaaatgta aggactaaat atctgcttat tgaaccttgc ttttggttc cctaatgcca     5820 ttttagtctg gctactgaag aacttatcca tcatgccatt tctgttatct taaattcagg    5880
cctcagattt tagagaaaat aagattcata ctggttggct ggataccagg atagccatgc    5940
gtgttcaagc tgagaggcct ccatggtata tttcagtcgt tggaggggct ttatatgtaa    6000
gacaaactat gccactcatt agcatttatg tgaagcaaat gcggaaaaca tgatcaatat    6060
gtcgtcttat ttaaatttat ttattttgt gctgcagaaa acagtaactg ccaacacggc     6120
```

```
cactgtttct gattatgttg gttatcttac caagggccag attccaccaa aggtactatt     6180
ctgttttttc aggatatgaa tgctgtttga atgtgaaaac cattgaccat aaatccttgt     6240
ttgcagcata tatccettgt ctatacgact gttgctttga atatagatgg gaaaaaatat     6300
acagtaagtg tgacattctt aatggggaaa cttaatttgt tgtaaataat caatatcata     6360
ttgactcgtg tatgctgcat catagatcga tactgtgagg agtggacatg gtagctacag     6420
attgcgaatg aatggatcaa cggttgacgc aaatgtacaa atattatgtg atggtgggct     6480
tttaatgcag gtaatatctt cttcctagtt aaagaagata tatcttgttc aaagaattct     6540
gattattgat cttttaatgt tttcagctgg atggaaacag ccatgtaatt tatgctgaag     6600
aagaggccag tggtacacga cttcttattg atggaaagac atgcatgtta caggtaatga     6660
tagccttgtt cttttagtt ctagtcacgg tgtttgcttg ctatttgttg tatctattta     6720
atgcattcac taattactat attagtttgc atcatcaagt taaaatggaa cttctttctt     6780
gcagaatgac catgacccat caaagttatt agctgagaca ccatgcaaac ttcttcgttt     6840
cttggttgct gatggtgctc atgttgatgc tgatgtacca tatgcggaag ttgaggttat     6900
gaagatgtgc atgccctct tatcacccgc ttctggtgtc atacatgttg taatgtctga     6960
gggccaagca atgcaggtac attcctacat tccattcatt gtgctgtgct gacatgaaca     7020
tttcaagtaa atacctgtaa cttgtttatt attctaggct ggtgatctta tagctaggct     7080
ggatcttgat gacccttctg ctgttaagag agctgagccg ttcgaagata cttttccaca     7140
aatgggtctc cctattgctg cttctggcca agttcacaaa ttatgtgctg caagtctgaa     7200
tgcttgtcga atgatccttg cggggtatga gcatgatatt gacaaggtaa acatcatgtc     7260
ctcttgtttt ttcttttgtt tatcatgcat tcttatgttc atcatgtcct ctggcaaatc     7320
tagattccgc tgtcgtttca cacagatttt tctcattctc ataatggtgc caaacataaa     7380
tatgctgcta tattcatcaa tgttttcact cgatttctaa ttttgctttt gagttttaaa     7440
ctttagtaca atccatatct aatctccttt ggcaacagtg aatccattat atatattttt     7500
attaaactgc tttctttttc aggttgtgcc agagttggta tactgcctag acactccgga     7560
gcttcctttc ctgcagtggg aggagcttat gtctgtttta gcaactagac ttccaagaaa     7620
tcttaaaagt gaggtatatt atggttgaca agatagctag tctcatgctc taaggacttg     7680
tacatttcgc cacataggtt aattttccat atcaagttct aatgtacgat ataaaagtag     7740
tactggccta aaacagtatt ggtggttgac tatctttgtt gtgtaagatc aagtatttct     7800
ttttcatgct tagtttgtca atacttcaca tttatcactg acttgtcgag ctaaatgaga     7860
ttttatttga tttctgtgct ccattatttt tgtatatata tatatatatt taactatgac     7920
tatatgttat gcctcaaacg tttcaaactc tttcagttgg agggcaaata tgaggaatac     7980
aaagtaaaat ttgactctgg gataatcaat gatttccctg ccaatatgct acgagtgata     8040
attgaggtca gttattcaat ttgttgtgat aatcactgcc ttaactgttc gttcttttaa     8100
caagcggttt tataggaaaa tcttgcatgt ggttctgaga aggagaaggc tacaaatgag     8160
aggcttgttg agcctcttat gagcctactg aagtcatatg agggtgggag agaaagtcat     8220
gctcactttg ttgtcaagtc ccttttttgag gagtatctct atgttgaaga attgttcagt     8280
gatggaattc aggttaactt acctattcgc attaaacaaa tcatcagttg ttttatgata     8340
aagtcaaaat gtttatattt cccattcttc tgtggatcaa atatatcacg gacatgatat     8400
agtttcctta ggctatataa tggttcttca tcaaataata ttgcaggaaa cagtatagca     8460
aactatttgt atatactcga gatggaaatt gttagaaaca tcattgacta aatctgtcct     8520
```

```
ttgttacgct gtttttgtag tctgatgtga ttgagcgtct gcgccttcaa catagtaaag   8580
acctacagaa ggtcgtagac attgtgttgt cccaccaggt aaatttcttc atggtctgat   8640
gacttcactg cgaatggtta ctgaactgtc ttcttgttct gacaatgtga cttttctttg   8700
tagagtgtta gaaataaaac taagctgata ctaaaactca tggagagtct ggtctatcca   8760
aatcctgctg cctacaggga tcaattgatt cgcttttctt cccttaatca caaagcgtat   8820
tacaaggtga ccaggataaa cataaataaa cgtgaatttt tcaatgacct tttcttctga   8880
catctgaatc tgatgaattt cttgcatatt aatacagttg gcacttaaag ctagtgaact   8940
tcttgaacaa acaaaactta gtgagctccg tgcaagaata gcaaggagcc tttcagagct   9000
ggagatgttt actgaggaaa gcaagggtct ctccatgcat aagcgagaaa ttgccattaa   9060
ggagagcatg gaagatttag tcactgctcc actgccagtt gaagatgcgc tcatttcttt   9120
atttgattgt agtgatacaa ctgttcaaca gagagtgatt gagacttata tagctcgatt   9180
ataccaggta tgagaagaaa gacctttttga aattatttat attaacatat cctagtaaaa   9240
cagcatgctc atcatttctt aaaaaaagtt tacagcacct gatgtttggt tactgaccgc   9300
atcattaaaa taaagttact tgttgtggag agatgtattt tggaacttgt ggcacatgca   9360
gtaacatgct actgctcgat atgtttgcta acttgacaac aatattttc agcctcatct   9420 tgtaaaggac agtatcaaaa tgaaatggat agaatcgggt gttattgctt tatgggaatt   9480
tcctgaaggg cattttgatg caagaaatgg aggagcggtt cttggtgaca aagatgggg   9540 tgccatggtc attgtcaagt ctcttgaatc actttcaatg ccattagat ttgcactaaa   9600 ggagacatca cactacacta gctctgaggg caatatgatg catattgctt tgttgggtgc   9660
tgataataag atgcatataa ttcaagaaag gtatgttcat atgctatgtt ggtgctgaaa   9720
tagttatata tgtagttagc tggtggagtt ctggtaatta acctatccca ttgttcagtg   9780
gtgatgatgc tgacagaata gccaaacttc ccttgatact aaaggataat gtaaccgatc   9840
tgcatgcctc tggtgtgaaa acaataagtt tcattgttca aagagatgaa gcacggatga   9900
caatgcgtcg taccttcctt tggtctgatg aaaagctttc ttatgaggaa gagccaattc   9960
tccggcatgt ggaacctcct ctttctgcac ttcttgagtt ggtacgtgat atcatcaaaa  10020
tgataatgtt ttggtatggc attgattatc ttctatgctc tttgtattta ttcagcctat  10080
tgtggataca ggacaagttg aaagtgaaag gatacaatga aatgaagtat accccatcac  10140
gggatcgtca atggcatatc tacacactta gaaatactga aaaccccaaa atgttgcacc  10200 gggtatttt ccgaacccttt gtcaggcaac ccagtgtatc caacaagttt tcttcgggcc  10260
agattggtga catggaagtt gggagtgctg aagaacctct gtcatttaca tcaaccagca  10320
tattaagatc tttgatgact gctatagagg aattggagct tcacgcaatt agaactggcc  10380
attcacacat gtatttgcat gtattgaaag aacaaaagct tcttgatctt gttccagttt  10440
cagggtaagt gcgcatattt cttttttggga acatatgctt gcttatgagg ttggtcttct  10500
caatgatctt cttatcttac tcaggaatac agttttggat gttggtcaag atgaagctac  10560
tgcatattca cttttaaaag aaatggctat gaagatacat gaacttgttg gtgcaagaat  10620
gcaccatctt tctgtatgcc aatgggaagt gaaacttaag ttggactgcg atggtcctgc  10680
cagtggtacc tggaggattg taacaaccaa tgttactagt cacacttgca ctgtggatgt  10740
aagtttaatc ctctagcatt ttgttttctt tggaaaagca tgtgatttta agccggctgg  10800
tcctcatacc cagacctagt gatctttata tagtgtagac atttttctaa ctgcttttaa  10860
```

```
ttgttttaga tctaccgtga gatggaagat aaagaatcac ggaagttagt ataccatccc   10920
gccactccgg cggctggtcc tctgcatggt gtggcactga ataatccata tcagcctttg   10980
agtgtcattg atctcaaacg ctgttctgct aggaataata gaactacata ctgctatgat   11040
tttccactgg tgagttgact gctcccttat attcaatgca ttaccatagc aaattcatat   11100
tcgttcatgt tgtcaaaata agccgatgaa aattcaaaac tgtaggcatt tgaaactgca   11160
gtgaggaagt catggtcctc tagtacctct ggtgcttcta aaggtgttga aaatgcccaa   11220
tgttatgtta aagctacaga gttggtattt gcggacaaac atgggtcatg gggcactcct   11280
ttagttcaaa tggaccggcc tgctgggctc aatgacattg gtatggtagc ttggaccttg   11340
aagatgtcca ctcctgaatt tcctagtggt agggagatta ttgttgttgc aaatgatatt   11400
acgttcagag ctggatcatt tggcccaagg gaagatgcat tttttgaagc tgttaccaac   11460
ctagcctgtg agaagaaact tcctcttatt tatttggcag caaattctgg tgctcgaatt   11520
ggcatagcag atgaagtgaa atcttgcttc cgtgttgggt ggtctgatga tggcagccct   11580
gaacgtgggt ttcagtacat ttatctaagc gaagaagact atgctcgtat tggcacttct   11640
gtcatagcac ataagatgca gctagacagt ggtgaaatta ggtgggttat tgattctgtt   11700
gtgggcaagg aagatggact tggtgtggag aatgtacatg gaagtgctgc tattgccagt   11760
gcttattcta gggcatataa ggagacattt acacttacat ttgtgactgg aagaactgtt   11820
ggaataggag cttatcttgc tcgacttggc atccggtgca tacagcgtct tgaccagcct   11880
attattctta caggctattc tgcactgaac aagcttcttg ggcgggaagt gtacagctcc   11940
cacatgcagt tgggtggtcc caaaatcatg gcaactaatg tgttgtcca tcttactgtt   12000 tcagatgacc ttgaaggcgt ttctaatata ttgaggtggc tcagttatgt tcctgcctac   12060
attggtggac cacttccagt aacaacaccg ttggacccac cggacagacc tgttgcatac   12120
attcctgaga actcgtgtga tcctcgagcg gctatccgtg gtgttgatga cagccaaggg   12180
aaatggttag gtggtatgtt tgataaagac agctttgtgg aaacatttga aggttgggct   12240
aagacagtgg ttactggcag agcaaagctt ggtggaattc cagtgggtgt gatagctgtg   12300
gagactcaga ccatgatgca aactatccct gctgaccctg gtcagcttga ttcccgtgag   12360
caatctgttc ctcgtgctgg acaagtgtgg tttccagatt ctgcaaccaa gactgcgcag   12420
gcattgctgg acttcaaccg tgaaggatta cctctgttca tcctcgctaa ctggagaggc   12480
ttctctggtg gacaaagaga tctttttgaa ggaattcttc aggctggctc gactattgtt   12540
gagaacctta ggcatacaa tcagcctgcc tttgtctaca ttcccatggc tgcagagcta   12600
cgaggagggg cttgggttgt ggttgatagc aagataaacc cagaccgcat tgagtgctat   12660
gctgagagga ctgcaaaagg caatgttctg gaaccgcaag ggttaattga gatcaagttc   12720
aggtcagagg aactccagga ttgcatgagt cggcttgacc caacattaat tgatctgaaa   12780
gcaaaactcg aagtagcaaa taaaaatgga agtgctgaca caaaatcgct tcaagaaaat   12840
atagaagctc gaacaaaaca gttgatgcct ctatatactc agattgcgat acggtttgct   12900
gaattgcatg atacatccct cagaatggct gcgaaaggtg tgattaagaa agttgtggac   12960
tgggaagaat cacgatcttt cttctataag agattacgga ggaggatctc tgaggatgtt   13020
cttgcaaaag aaattagagc tgtagcaggt gagcagtttt cccaccaacc agcaatcgag   13080
ctgatcaaga aatggtattc agcttcacat gcagctgaat gggatgatga cgatgctttt   13140
gttgcttgga tggataaccc tgaaaactac aaggattata ttcaatatct taaggctcaa   13200
agagtatccc aatccctctc aagtctttca gattccagct cagatttgca agccctgcca   13260
```

-continued

```
cagggtcttt ccatgttact agataaggta attagcttac tgatgcttat ataaattctt    13320
tttcattaca tatggctgga gaactatcta atcaaataat gattataatt ccaatcgttc    13380
tttttatgcc attatgatct tctgaaattt ccttctttgg acacttattc agatggatcc    13440
ctctagaaga gctcaacttg ttgaagaaat caggaaggtc cttggttgaa tcatatgatg    13500
ccaaaactat tattggaggc acaaatagct tgtggaccct gtcggattgt tggtgagtgt    13560
atattggatt tgttagttct gccagatgaa agtgcaagtc tgatgattca tgataccgtc    13620
agttggcaag aacaccggtt aacctgagtg cttgtttaca aatggtcctt tatgacaatc    13680
gttgtttcgc gctagttccg tgatctacta tcatctgtta gacgctgtaa ttagtgagtc    13740
tccgcggatc cacagtatac ggttgagctg ttgattcaat tttggacacg aataatatga    13800
ttttgtaggc ataaatgcgt ctgtatgtga aataaattgt ctgttgagtt aacacacaag    13860
atgacaatat gtttgtgctc tactgctatt gtccatgaat actgattgcg aatcaacca    13920 catgcattat a                                                        13931
```

<210> SEQ ID NO 6
<211> LENGTH: 13931
<212> TYPE: DNA
<213> ORGANISM: Artificial Sequence
<220> FEATURE:
<223> OTHER INFORMATION: mutant ACC

<400> SEQUENCE: 6

```
atgccgatgc ggccgtggga atttattatt ttaggccgca cagcccccat ctctccccca      60
cccctcggga tatccgcctt ctcccgcccg ctccgcctcc gcctccgcct ccgctcgcc     120 gccgttgtcg acgccgcaag gatccaaacg ccgccccgcg tcgccttctc cgccttcttc     180
ttcttcttct tcttcttctc cgagggtctc tctcgggaag gtacagctgc ccgcctccct     240
gctcttattt atcgcgtgcc gttcattccg tgccttctcc agctccagat ccgcgcgccg     300
cacgccgatc cgcgcccggc cggtgagtcc gccgcgggtt ccgccattg ctgccgtttc     360 tgcgctgcta gggggaggtt tagatgtggg tggtgggagc cgcgtgctgt tgtctgggat     420
gggagagaga gggtttaagg gtgggtgccg gatgcggatg ctcccgcccg ggttttggtc     480
ctgcttgtgg actggcgagg ggctagggt tgagttgtag ggattcggga tggaaatgga     540
ctggggagct cggatgggga ggtaatgcca cgccggtgaa atgcagctcg ctgttgttgg     600
ttctggttaa tgcctgggtg ttgctggcta tgttactatg ttgcatgcct acgcgagata     660
ctgccatgtg ccattttgcg tgattgtgat attggtttga ggttttagct gcgctcatca     720
tttcctcgcg ttggctcagg gtttaagctc ctctttgtta agtgggacgg tatgcatatg     780
cattgtgttc tttaggtttt aaattctggt tacggtgcca cacaacaagt cgtagatgct     840
cattcttgtt cttttcatgg ggcttatgga attgatggca catggcacac ctttctcctt     900
tttccgtcat gcatgttagt gccatattgt ctacgcaaaa aagaatattc tgcatatttg     960
tttactcact attttttttcc aagagaattg ggttttgcca tgcttcaaaa ggaacatttc    1020
aagctgaaaa agttctcccg atatggaatt agctttagag ttcaggggaa aaaatatgtt    1080
gttgctttgt gcttgtcaag taaccacagt tgcacaggtt ttgactgacc tcatgctact    1140
tgacattatt caccatgata agtttttacc ttttgttttt ttcctttcac taggaacaga    1200
acgaattgtt tgcataacca atttgtagat ttgcatgggg aaatagcat aactgaatat    1260 atctcaacct attactaggc aaaataagaa atgaacctaa gccttaacag gtttgcatca    1320
```

```
aattatcctg tgcaaaatga acaaaggtgg cacacaatgt acaagcttgc atttcatttt    1380
tggatcctca aacgtcttaa agacttttgc ataaagtatt tgatgagtaa cgagctggaa    1440
ctaatcattc ttatatattt tcatctgtca gatttcacac atctggggat ttatcttctc    1500
tttgtatggc actacacatt tgagaaaccg tgcaattcta ctgtttggtc agcaggacaa    1560
caatgacatc cacacatgtg gcgacattgg gagttggtgc ccaggcacct cctcgtcacc    1620
agaaaaagtc agctggcact gcatttgtat catctgggtc atcaagaccc tcataccgaa    1680
agaatggtca gcgtactcgg tcacttaggg aagaaagcaa tggaggagtg tctgattcca    1740
aaaagcttaa ccactctatt cgccaaggtg accactagct actttacata tgctataatt    1800
tgtgccaaac ataaacatgc aatggctgct attatttaaa cgttaatgtt gaaatagctg    1860
ctataggata cagcaaaaat atataattga ctgggcaaga tgcaacaatt gttttttcact   1920
aaagttagtt atcttttgct gtaaaagaca actgtttttt acataaaatg gtattaataa    1980
ccttgtaata ttcaatgcaa catgttctca agtaaaaaaa acattgcctt ggttgtataa    2040
gcaaatgtgt cgttgtagac atcttattaa accttttgt gatatctatt accgtaggga     2100
acagggagc tgtttaaatc tgttatcata gagtaatatg agaaagtgg attgtgcgac      2160
tttggcatgt atacctgctc aatttcaaat atatgtctat gtgcaggtct tgctggcatc    2220
attgacctcc caaatgacgc agcttcagaa gttgatattt cacagtaagg actttatatt    2280
ttataataat tattatataa ttttctgaca tgttttgaga acctcaaaac atgtgattgc    2340
accttccttt tttatgtctg gttcagaaac tgataagttt tgacagtgtt taggatggat    2400
ctttgatgcg cacagtgctt tctaatgttt tcattttga agtaatgtt ttaggaagaa      2460
atatctgatt aaatttatac tttatcttta caaaagtcaa atgcgttctg tatcaattgc    2520
ggtttgtaat atggcaagaa catgctttca gaatttgttc atacaatgct ttcttttctat   2580
tattatgtag aacaaatacc taatactttg ttcacctttt atagtggaca cctctcacag    2640
cttttttcagt aagtgatgca attttgtaca tttgtaagat gtgttccaga aacctttttct  2700
cctgcaattc taatgtaccc actcaaactg gtatcaccaa agatctccat ctgattgaaa    2760
aaaagctgcg tgaagtatgc ttattttatgc taaccataca tgatttatac tgttttatag   2820
tacaatgctt atttatgcta accatacata atttattct gttttctagt acattatttg     2880
tgcccctgac cataaatgat cctttctttt acagtggttc cgaagatccc aggggggccta   2940
cggtcccagg ttcctaccaa atgaatggga ttatcaatga aacacataat gggaggcatg    3000
cttcagtctc caaggttgtt gagttttgta cggcacttgg tggcaaaaca ccaattcaca    3060
gtgtattagt ggccaacaat ggaatggcag cagctaagtt catgcggagt gtccgaacat    3120
gggctaatga tacttttgga tcagagaagg caattcagct gatagctatg gcaactccgg    3180
aggatctgag gataaatgca gagcacatca gaattgccga tcaatttgta gaggtacctg    3240
gtggaacaaa caacaacaac tatgcaaatg tccaactcat agtggaggtt agttcagctc    3300
atccctcaac acaacatttt cgtttctatt taagttaggg aaaaatctct acgaccctcc    3360
aatttctgaa catccaattt tcaccatcaa ctgcaatcac agatagcaga gagaacaggt    3420
gtttctgctg tttggcctgg ttggggtcat gcatctgaga atcctgaact tccagatgcg    3480
ctgactgcaa aaggaattgt ttttcttggg ccaccagcat catcaatgca tgcattagga    3540
gacaaggttg gctcagctct cattgctcaa gcagctggag ttccaacact tgcttggagt    3600
ggatcacatg tgagccttgt cttctctttt ttagcttatc atcttatctt ttcggtgatg    3660
cattatccca atgacactaa accataggtg gaagttcctc tggagtgttg cttggactca    3720
```

```
atacctgatg agatgtatag aaaagcttgt gttactacca cagaggaagc agttgcaagt    3780
tgtcaggtgg ttggttatcc tgccatgatt aaggcatctt ggggtggtgg tggtaaagga    3840
ataaggaagg tttgttcttc ttgtagttat caagagattg tttggattgc aagtgtttag    3900
tgcccatagt taactctggt cttttctaaca tgagtaactc aactttcttg caggttcata    3960
atgatgatga ggttaggaca ttatttaagc aagttcaagg cgaagtacct ggttccccaa    4020
tatttatcat gaggctagct gctcaggtgg ggccttttat ggaagttaca ccttttccct    4080
taatgttgag ttattccgga gttattatgg ttatgttctg tatgtttgat ctgtaaatta    4140
ttgaaattca cctccattgg ttctccagat tagcagacct acaattctac atatggttta    4200
tactttataa atactaggat ttagggatct tcatatagtt tatacatggt atttagattt    4260
catttgtaac cctattgaag acatcctgat tgttgtctta tgtagagtcg acatcttgaa    4320
gttcagttgc tttgtgatca atatggcaac gtagcagcac ttcacagtcg agattgcagt    4380
gtacaacggc gacaccaaaa ggtctgctgt ctcagttaaa tcacccctct gaatgatcta    4440
cttcttgcct gctgcgttgg tcagaggaat aatggttgta ttctactgaa cagataatcg    4500
aggaaggacc agttactgtt gctcctcgtg agactgtgaa agagcttgag caggcagcac    4560
ggaggcttgc taaagctgtg ggttatgttg gtgctgctac tgttgaatac ctttacagca    4620
tggaaactgg tgaatattat tttctggaac ttaatccacg gctacaggtc ggctcctttg    4680
acattcttca ggaattaatt tctgttgacc acatgattta cattgtcaaa tggtctcaca    4740
ggttgagcat cctgtcactg agtggatagc tgaagtaaat ttgcctgcgg ctcaagttgc    4800
tgttggaatg ggtataccc tttggcagat tccaggtaat gcttcttcat ttagttcctg    4860
ctctttgtta attgaatgag ctcttataca gaccatgaga cacattctac tgttaattca    4920
tagtatcccc tgacttgtta gtgttagaga tacagagatg tatcacaaat tcattgtatc    4980
tcctcaagga ctgtaaaaat cctataatta aatttctgaa aatttgttct tttaagcaga    5040
aaaaaaatct ctaaattatc tccctgtata cagagatcag gcgcttctac ggaatgaacc    5100
atggaggagg ctatgacctt tggaggaaaa cagcagctct agcgactcca tttaactttg    5160
atgaagtaga ttctaaatgg ccaaaaggcc actgcgtagc tgttagaata actagcgagg    5220
atccagatga tgggtttaag cctactggtg gaaaagtaaa ggtgcggttt cctgatgtta    5280
ggtgtatgaa ttgaacacat tgctatattg cagctagtga aatgactgga tcatggttct    5340
cttattttca ggagataagt ttcaagagta aaccaaatgt ttgggcctat ttctcagtaa    5400
aggtagtcct caatattgtt gcactgccac attatttgag ttgtcctaac aattgtgctg    5460
caattgttag ttttcaacta tttgttgttc tgtttggttg actggtaccc tctctttgca    5520
gtctggtgga ggcatccatg aattcgctga ttctcagttc ggtatgtaaa gttaaaagag    5580
taatattgtc tttgctattt atgtttgtcc tcacttttaa aagatattgc cttccattac    5640
aggacatgtt tttgcgtatg gaactactag atcggcagca ataactacca tggctcttgc    5700
actaaaagag gttcaaattc gtggagaaat tcattcaaac gtagactaca cagttgacct    5760
attaaatgta aggactaaat atctgcttat tgaaccttgc tttttggttc cctaatgcca    5820
ttttagtctg gctactgaag aacttatcca tcatgccatt tctgttatct taaattcagg    5880
cctcagattt tagagaaaat aagattcata ctggttggct ggataccagg atagccatgc    5940
gtgttcaagc tgagaggcct ccatggtata tttcagtcgt tggaggggct ttatatgtaa    6000
gacaaactat gccactcatt agcatttatg tgaagcaaat gcggaaaaca tgatcaatat    6060
```

```
gtcgtcttat ttaaatttat ttattttgt gctgcagaaa acagtaactg ccaacacggc    6120
cactgtttct gattatgttg gttatcttac caagggccag attccaccaa aggtactatt    6180
ctgttttttc aggatatgaa tgctgtttga atgtgaaaac cattgaccat aaatccttgt    6240
ttgcagcata tatcccttgt ctatacgact gttgctttga atatagatgg gaaaaaatat    6300
acagtaagtg tgacattctt aatggggaaa cttaatttgt tgtaaataat caatatcata    6360
ttgactcgtg tatgctgcat catagatcga tactgtgagg agtggacatg gtagctacag    6420
attgcgaatg aatggatcaa cggttgacgc aaatgtacaa atattatgtg atggtgggct    6480
tttaatgcag gtaatatctt cttcctagtt aaagaagata tatcttgttc aaagaattct    6540
gattattgat cttttaatgt tttcagctgg atggaaacag ccatgtaatt tatgctgaag    6600
aagaggccag tggtacacga cttcttattg atggaaagac atgcatgtta caggtaatga    6660
tagccttgtt cttttagtt ctagtcacgg tgtttgcttg ctatttgttg tatctattta    6720
atgcattcac taattactat attagtttgc atcatcaagt taaaatggaa cttctttctt    6780
gcagaatgac catgacccat caaagttatt agctgagaca ccatgcaaac ttcttcgttt    6840
cttggttgct gatggtgctc atgttgatgc tgatgtacca tatgcggaag ttgaggttat    6900
gaagatgtgc atgcccctct tatcacccgc ttctggtgtc atacatgttg taatgtctga    6960
gggccaagca atgcaggtac attcctacat tccattcatt gtgctgtgct gacatgaaca    7020
tttcaagtaa atacctgtaa cttgtttatt attctaggct ggtgatctta tagctaggct    7080
ggatcttgat gacccttctg ctgttaagag agctgagccg ttcgaagata cttttccaca    7140
aatgggtctc cctattgctg cttctggcca agttcacaaa ttatgtgctg caagtctgaa    7200
tgcttgtcga atgatccttg cggggtatga gcatgatatt gacaaggtaa acatcatgtc    7260
ctcttgtttt ttcttttgtt tatcatgcat tcttatgttc atcatgtcct ctggcaaatc    7320
tagattccgc tgtcgtttca cacagatttt tctcattctc ataatggtgc caaacataaa    7380
tatgctgcta tattcatcaa tgttttcact cgatttctaa ttttgctttt gagttttaaa    7440
ctttagtaca atccatatct aatctccttt ggcaacagtg aatccattat atatatttt    7500 attaaactgc tttcttttc aggttgtgcc agagttggta tactgcctag acactccgga    7560
gcttcctttc ctgcagtggg aggagcttat gtctgtttta gcaactagac ttccaagaaa    7620
tcttaaaagt gaggtatatt atggttgaca agatagctag tctcatgctc taaggacttg    7680
tacatttcgc cacataggtt aattttccat atcaagttct aatgtacgat ataaaagtag    7740
tactggccta aaacagtatt ggtggttgac tatctttgtt gtgtaagatc aagtatttct    7800
ttttcatgct tagtttgtca atacttcaca tttatcactg acttgtcgag ctaaatgaga    7860
ttttatttga tttctgtgct ccattatttt tgtatatata tatatatatt taactatgac    7920
tatatgttat gcctcaaacg tttcaaactc tttcagttgg agggcaaata tgaggaatac    7980
aaagtaaaat ttgactctgg gataatcaat gatttccctg ccaatatgct acgagtgata    8040
attgaggtca gttattcaat ttgttgtgat aatcactgcc ttaactgttc gttcttttaa    8100
caagcggttt tataggaaaa tcttgcatgt ggttctgaga aggagaaggc tacaaatgag    8160
aggcttgttg agcctcttat gagcctactg aagtcatatg agggtgggag agaaagtcat    8220
gctcactttg ttgtcaagtc cctttttgag gagtatctct atgttgaaga attgttcagt    8280
gatggaattc aggttaactt acctattcgc attaaacaaa tcatcagttg ttttatgata    8340
aagtcaaaat gtttatattt cccattcttc tgtggatcaa atatatcacg gacatgatat    8400
agtttcctta ggctatataa tggttcttca tcaaataata ttgcaggaaa cagtatagca    8460
```

```
aactatttgt atatactcga gatggaaatt gttagaaaca tcattgacta aatctgtcct    8520
ttgttacgct gttttgtag tctgatgtga ttgagcgtct gcgccttcaa catagtaaag    8580
acctacagaa ggtcgtagac attgtgttgt cccaccaggt aaatttcttc atggtctgat    8640
gacttcactg cgaatggtta ctgaactgtc ttcttgttct gacaatgtga cttttctttg    8700
tagagtgtta gaaataaaac taagctgata ctaaaactca tggagagtct ggtctatcca    8760
aatcctgctg cctacaggga tcaattgatt cgcttttctt cccttaatca caaagcgtat    8820
tacaaggtga ccaggataaa cataaataaa cgtgaatttt tcaatgacct tttcttctga    8880
catctgaatc tgatgaattt cttgcatatt aatacagttg gcacttaaag ctagtgaact    8940
tcttgaacaa acaaaactta gtgagctccg tgcaagaata gcaaggagcc tttcagagct    9000
ggagatgttt actgaggaaa gcaagggtct ctccatgcat aagcgagaaa ttgccattaa    9060
ggagagcatg gaagatttag tcactgctcc actgccagtt gaagatgcgc tcatttcttt    9120
atttgattgt agtgatacaa ctgttcaaca gagagtgatt gagacttata tagctcgatt    9180
ataccaggta tgagaagaaa gacctttgta aattatttat attaacatat cctagtaaaa    9240
cagcatgctc atcatttctt aaaaaaagtt tacagcacct gatgtttggt tactgaccgc    9300
atcattaaaa taaagttact tgttgtggag agatgtattt tggaacttgt ggcacatgca    9360
gtaacatgct actgctcgat atgtttgcta acttgacaac aatatttttc agcctcatct    9420
tgtaaaggac agtatcaaaa tgaaatggat agaatcgggt gttattgctt tatgggaatt    9480
tcctgaaggg catttgatg caagaaatgg aggagcggtt cttggtgaca aaagatgggg    9540
tgccatggtc attgtcaagt ctcttgaatc actttcaatg gccattagat ttgcactaaa    9600
ggagacatca cactcacta gctctgaggg caatatgatg catattgctt tgttgggtgc    9660
tgataataag atgcatataa ttcaagaaag gtatgttcat atgctatgtt ggtgctgaaa    9720
tagttatata tgtagttagc tggtggagtt ctggtaatta acctatccca ttgttcagtg    9780
gtgatgatgc tgacagaata gccaaacttc ccttgatact aaaggataat gtaaccgatc    9840
tgcatgcctc tggtgtgaaa acaataagtt tcattgttca aagagatgaa gcacggatga    9900
caatgcgtcg taccttcctt tggtctgatg aaaagctttc ttatgaggaa gagccaattc    9960
tccggcatgt ggaacctcct cttctgcac ttcttgagtt ggtacgtgat atcatcaaaa    10020
tgataatgtt ttggtatggc attgattatc ttctatgctc tttgtattta ttcagcctat    10080
tgtggataca ggacaagttg aaagtgaaag gatacaatga aatgaagtat accccatcac    10140
gggatcgtca atggcatatc tacacactta gaaatactga aaaccccaaa atgttgcacc    10200
gggtattttt ccgaaccctt gtcaggcaac ccagtgtatc caacaagttt tcttcgggcc    10260
agattggtga catggaagtt gggagtgctg aagaacctct gtcatttaca tcaaccagca    10320
tattaagatc tttgatgact gctatagagg aattggagct tcacgcaatt agaactggcc    10380
attcacacat gtatttgcat gtattgaaag aacaaaagct tcttgatctt gttccagttt    10440
cagggtaagt gcgcatattt ctttttggga acatatgctt gcttatgagg ttggtcttct    10500
caatgatctt cttatcttac tcaggaatac agttttggat gttggtcaag atgaagctac    10560
tgcatattca cttttaaaag aaatggctat gaagatacat gaacttgttg gtgcaagaat    10620
gcaccatctt tctgtatgcc aatgggaagt gaaacttaag ttggactgcg atggtcctgc    10680
cagtggtacc tggaggattg taacaaccaa tgttactagt cacacttgca ctgtggatgt    10740
aagtttaatc ctctagcatt ttgttttctt tggaaaagca tgtgattta agccggctgg    10800
```

```
tcctcatacc cagacctagt gatctttata tagtgtagac attttttctaa ctgctttttaa    10860 ttgttttaga tctaccgtga gatggaagat aaagaatcac ggaagttagt ataccatccc     10920
gccactccgg cggctggtcc tctgcatggt gtggcactga ataatccata tcagcctttg     10980
agtgtcattg atctcaaacg ctgttctgct aggaataata gaactacata ctgctatgat     11040
tttccactgg tgagttgact gctcccttat attcaatgca ttaccatagc aaattcatat     11100
tcgttcatgt tgtcaaaata agccgatgaa aattcaaaac tgtaggcatt tgaaactgca     11160
gtgaggaagt catggtcctc tagtacctct ggtgcttcta aaggtgttga aaatgcccaa     11220
tgttatgtta aagctacaga gttggtattt gcggacaaac atgggtcatg ggcactcct      11280 ttagttcaaa tggaccggcc tgctgggctc aatgacattg gtatggtagc ttggaccttg     11340
aagatgtcca ctcctgaatt tcctagtggt agggagatta ttgttgttgc aaatgatatt     11400
acgttcagag ctggatcatt tggcccaagg gaagatgcat ttttgaagc tgttaccaac      11460 ctagcctgtg agaagaaact tcctcttatt tatttggcag caaattctgg tgctcgaatt     11520
ggcatagcag atgaagtgaa atcttgcttc cgtgttgggt ggtctgatga tggcagccct    11580
gaacgtgggt ttcagtacat ttatctaagc gaagaagact atgctcgtat tggcacttct    11640
gtcatagcac ataagatgca gctagacagt ggtgaaatta ggtgggttat tgattctgtt    11700
gtgggcaagg aagatggact tggtgtggag aatatacatg gaagtgctgc tattgccagt    11760
gcttattcta gggcatataa ggagacattt acacttacat ttgtgactgg aagaactgtt    11820
ggaataggag cttatcttgc tcgacttggc atccggtgca tacagcgtct tgaccagcct    11880
attattctta caggctattc tgcactgaac aagcttcttg ggcgggaagt gtacagctcc    11940
cacatgcagt tgggtggtcc caaaatcatg gcaactaatg gtgttgtcca tcttactgtt    12000
tcagatgacc ttgaaggcgt ttctaatata ttgaggtggc tcagttatgt tcctgcctac    12060
attggtggac cacttccagt aacaacaccg ttggacccac cggacagacc tgttgcatac    12120
attcctgaga actcgtgtga tcctcgagcg gctatccgtg tgttgatga cagccaaggg    12180 aaatggttag gtggtatgtt tgataaagac agctttgtgg aaacatttga aggttgggct    12240
aagacagtgg ttactggcag agcaaagctt ggtggaattc cagtgggtgt gatagctgtg    12300
gagactcaga ccatgatgca aactatccct gctgaccctg gtcagcttga ttcccgtgag    12360
caatctgttc ctcgtgctgg acaagtgtgg tttccagatt ctgcaaccaa gactgcgcag    12420
gcattgctgg acttcaaccg tgaaggatta cctctgttca tcctcgctaa ctggagaggc    12480
ttctctggtg gacaaagaga tctttttgaa ggaattcttc aggctggctc gactattgtt    12540
gagaacctta ggacatacaa tcagcctgcc tttgtctaca ttcccatggc tgcagagcta    12600
cgaggagggc cttgggttgt ggttgatagc aagataaacc cagaccgcat tgagcgctat    12660
gctgagagga ctgcaaaagg caatgttctg gaaccgcaag ggttaattga gatcaagttc    12720
aggtcagagg aactccagga ttgcatgagt cggcttgacc caacattaat tgatctgaaa    12780
gcaaaactcg aagtagcaaa taaaaatgga agtgctgaca caaaatcgct tcaagaaaat    12840
atagaagctc gaacaaaaca gttgatgcct ctatatactc agattgcgat acggtttgct    12900
gaattgcatg atacatccct cagaatggct gcgaaaggtg tgattaagaa agttgtggac    12960
tgggaagaat cacgatcttt cttctataag agattacgga ggaggatctc tgaggatgtt    13020
cttgcaaaag aaattagagc tgtagcaggt gagcagtttt cccaccaacc agcaatcgag    13080
ctgatcaaga aatggtattc agcttcacat gcagctgaat gggatgatga cgatgctttt    13140
gttgcttgga tggataaccc tgaaaactac aaggattata ttcaatatct taaggctcaa    13200
```

-continued

```
agagtatccc aatccctctc aagtctttca gattccagct cagatttgca agccctgcca    13260
cagggtcttt ccatgttact agataaggta attagcttac tgatgcttat ataaattctt    13320
tttcattaca tatggctgga gaactatcta atcaaataat gattataatt ccaatcgttc    13380
tttttatgcc attatgatct tctgaaattt ccttctttgg acacttattc agatggatcc    13440
ctctagaaga gctcaacttg ttgaagaaat caggaaggtc cttggttgaa tcatatgatg    13500
ccaaaactat tattggaggc acaaatagct tgtggaccct gtcggattgt tggtgagtgt    13560
atattggatt tgttagttct gccagatgaa agtgcaagtc tgatgattca tgataccgtc    13620
agttggcaag aacaccggtt aacctgagtg cttgtttaca aatggtcctt tatgacaatc    13680
gttgtttcgc gctagttccg tgatctacta tcatctgtta gacgctgtaa ttagtgagtc    13740
tccgcggatc cacagtatac ggttgagctg ttgattcaat tttggacacg aataatatga    13800
ttttgtaggc ataaatgcgt ctgtatgtga aataaattgt ctgttgagtt aacacacaag    13860
atgacaatat gtttgtgctc tactgctatt gtccatgaat actgattgcg gaatcaacca    13920
catgcattat a                                                         13931
```

<210> SEQ ID NO 7
<211> LENGTH: 13931
<212> TYPE: DNA
<213> ORGANISM: Artificial Sequence
<220> FEATURE:
<223> OTHER INFORMATION: mutant ACC

<400> SEQUENCE: 7

```
atgccgatgc ggccgtggga atttattatt ttaggccgca cagcccccat ctctccccca      60
cccctcggga tatccgcctt ctcccgcccg ctccgcctcc gctccgcct ccgcctcgcc     120 gccgttgtcg acgccgcaag gatccaaacg ccgccccgcg tcgccttctc cgccttcttc     180
ttcttcttct tcttcttctc cgagggtctc tctcggaag gtacagctgc ccgcctccct      240
gctcttattt atcgcgtgcc gttcattccg tgccttctcc agctccagat ccgcgcgccg     300
cacgccgatc cgcgcccggc cggtgagtcc gccgcgggtt ccgccattg ctgccgtttc      360 tgcgctgcta gggggaggtt tagatgtggg tggtgggagc cgcgtgctgt tgtctgggat     420
gggagagaga gggtttaagg gtgggtgccg gatgcggatg ctcccgcccg gttttggtc      480 ctgcttgtgg actggcgagg ggctaggggt tgagttgtag ggattcggga tggaaatgga     540
ctggggagct cggatgggga ggtaatgcca cgccggtgaa atgcagctcg ctgttgttgg     600
ttctggttaa tgcctgggtg ttgctggcta tgttactatg ttgcatgcct acgcgagata     660
ctgccatgtg ccatttttgcg tgattgtgat attggtttga ggttttagct gcgctcatca     720
tttcctcgcg ttggctcagg gtttaagctc ctctttgtta agtgggacgg tatgcatatg     780
cattgtgttc tttaggtttt aaattctggt tacggtgcca cacaacaagt cgtagatgct     840
cattcttgtt cttttcatgg ggcttatgga attgatggca catggcacac ctttctcctt     900
tttccgtcat gcatgttagt gccatattgt ctacgcaaaa aagaatattc tgcatatttg     960
tttactcact attttttttcc aagagaattg ggttttgcca tgcttcaaaa ggaacatttc    1020
aagctgaaaa agttctcccg atatggaatt agctttagag ttcaggggaa aaatatgtt    1080 gttgctttgt gcttgtcaag taaccacagt tgcacaggtt ttgactgacc tcatgctact    1140
tgacattatt caccatgata aagttttacc ttttgttttt ttcctttcac taggaacaga    1200
acgaattgtt tgcataacca atttgtagat ttgacatggg gaaatagcat aactgaatat    1260
```

```
atctcaacct attactaggc aaaataagaa atgaacctaa gccttaacag gtttgcatca    1320
aattatcctg tgcaaaatga acaaaggtgg cacacaatgt acaagcttgc atttcatttt    1380
tggatcctca aacgtcttaa agactttttgc ataaagtatt tgatgagtaa cgagctggaa   1440
ctaatcattc ttatatattt tcatctgtca gatttcacac atctggggat ttatcttctc    1500
tttgtatggc actacacatt tgagaaaccg tgcaattcta ctgtttggtc agcaggacaa    1560
caatgacatc cacacatgtg gcgacattgg gagttggtgc ccaggcacct cctcgtcacc    1620
agaaaaagtc agctggcact gcatttgtat catctgggtc atcaagaccc tcataccgaa    1680
agaatggtca gcgtactcgg tcacttaggg aagaaagcaa tggaggagtg tctgattcca    1740
aaaagcttaa ccactctatt cgccaaggtg accactagct actttacata tgctataatt    1800
tgtgccaaac ataaacatgc aatggctgct attatttaaa cgttaatgtt gaaatagctg    1860
ctataggata cagcaaaaat atataattga ctgggcaaga tgcaacaatt gttttttcact   1920 aaagttagtt atcttttgct gtaaaagaca actgttttttt acataaaatg gtattaataa   1980
ccttgtaata ttcaatgcaa catgttctca agtaaaaaaa acattgcct ggttgtataa     2040 gcaaatgtgt cgttgtagac atcttattaa accttttttgt gatatctatt accgtaggga   2100
acaggggagc tgtttaaatc tgttatcata gagtaatatg agaaaagtgg attgtgcgac    2160
tttggcatgt atacctgctc aatttcaaat atatgtctat gtgcaggtct tgctggcatc    2220
attgacctcc caaatgacgc agcttcagaa gttgatattt cacagtaagg actttatatt    2280
ttataataat tattatataa ttttctgaca tgttttgaga acctcaaaac atgtgattgc    2340
accttccttt tttatgtctg gttcagaaac tgataagttt tgacagtgtt taggatggat    2400
ctttgatgcg cacagtgctt tctaatgttt tcattttttga aagtaatgtt ttaggaagaa   2460
atatctgatt aaatttatac tttatcttta caaaagtcaa atgcgttctg tatcaattgc    2520
ggtttgtaat atggcaagaa catgctttca gaatttgttc atacaatgct ttctttctat    2580
tattatgtag aacaaatacc taatactttg ttcacctttt atagtggaca cctctcacag    2640 cttttttcagt aagtgatgca attttgtaca tttgtaagat gtgttccaga aacctttttct  2700 cctgcaattc taatgtaccc actcaaactg gtatcaccaa agatctccat ctgattgaaa    2760
aaaagctgcg tgaagtatgc ttatttatgc taaccataca tgatttatac tgttttatag    2820
tacaatgctt atttatgcta accatacata attttattct gttttctagt acattatttg    2880
tgcccctgac cataaatgat ccttttctttt acagtggttc cgaagatccc agggggccta   2940
cggtcccagg ttcctaccaa atgaatggga ttatcaatga aacacataat gggaggcatg    3000
cttcagtctc caaggttgtt gagttttgta cggcacttgg tggcaaaaca ccaattcaca    3060
gtgtattagt ggccaacaat ggaatggcag cagctaagtt catgcgggagt gtccgaacat   3120 gggctaatga tacttttgga tcagagaagg caattcagct gatagctatg gcaactccgg    3180
aggatctgag gataaatgca gagcacatca gaattgccga tcaattttgta gaggtacctg   3240 gtggaacaaa caacaacaac tatgcaaatg tccaactcat agtggaggtt agttcagctc    3300
atccctcaac acaacatttt cgtttctatt taagttaggg aaaaatctct acgaccctcc    3360
aatttctgaa catccaattt tcaccatcaa ctgcaatcac agatagcaga gagaacaggt    3420
gtttctgctg tttggcctgg ttggggtcat gcatctgaga atcctgaact tccagatgcg    3480
ctgactgcaa aaggaattgt ttttcttggg ccaccagcat catcaatgca tgcattagga    3540
gacaaggttg gctcagctct cattgctcaa gcagctggag ttccaacact tgcttggagt    3600
ggatcacatg tgagccttgt cttctctttt ttagcttatc atcttatctt tcggtgatg     3660
```

```
cattatccca atgacactaa accataggtg gaagttcctc tggagtgttg cttggactca   3720
atacctgatg agatgtatag aaaagcttgt gttactacca cagaggaagc agttgcaagt   3780
tgtcaggtgg ttggttatcc tgccatgatt aaggcatctt ggggtggtgg tggtaaagga   3840
ataaggaagg tttgttcttc ttgtagttat caagagattg tttggattgc aagtgtttag   3900
tgcccatagt taactctggt ctttctaaca tgagtaactc aactttcttg caggttcata   3960
atgatgatga ggttaggaca ttatttaagc aagttcaagg cgaagtacct ggttccccaa   4020
tatttatcat gaggctagct gctcaggtgg ggccttttat ggaagttaca ccttttccct   4080
taatgttgag ttattccgga gttattatgg ttatgttctg tatgtttgat ctgtaaatta   4140
ttgaaattca cctccattgg ttctccagat tagcagacct acaattctac atatggttta   4200
tactttataa atactaggat ttagggatct tcatatagtt tatacatggt atttagattt   4260
catttgtaac cctattgaag acatcctgat tgttgtctta tgtagagtcg acatcttgaa   4320
gttcagttgc tttgtgatca atatggcaac gtagcagcac ttcacagtcg agattgcagt   4380
gtacaacggc gacaccaaaa ggtctgctgt ctcagttaaa tcacccctct gaatgatcta   4440
cttcttgcct gctgcgttgg tcagaggaat aatggttgta ttctactgaa cagataatcg   4500
aggaaggacc agttactgtt gctcctcgtg agactgtgaa agagcttgag caggcagcac   4560
ggaggcttgc taaagctgtg ggttatgttg gtgctgctac tgttgaatac ctttacagca   4620
tggaaactgg tgaatattat tttctggaac ttaatccacg gctacaggtc ggctcctttg   4680
acattcttca ggaattaatt tctgttgacc acatgattta cattgtcaaa tggtctcaca   4740
ggttgagcat cctgtcactg agtggatagc tgaagtaaat ttgcctgcgg ctcaagttgc   4800
tgttggaatg ggtataccccc tttggcagat tccaggtaat gcttcttcat ttagttcctg   4860
ctctttgtta attgaatgag ctcttataca gaccatgaga cacattctac tgttaattca   4920
tagtatcccc tgacttgtta gtgttagaga tacagagatg tatcacaaat tcattgtatc   4980
tcctcaagga ctgtaaaaat cctataatta aatttctgaa atttgttct tttaagcaga    5040 aaaaaaatct ctaaattatc tccctgtata cagagatcag gcgcttctac ggaatgaacc   5100
atggaggagg ctatgacctt tggaggaaaa cagcagctct agcgactcca tttaactttg   5160
atgaagtaga ttctaaatgg ccaaaaggcc actgcgtagc tgttagaata actagcgagg   5220
atccagatga tgggtttaag cctactggtg gaaaagtaaa ggtgcggttt cctgatgtta   5280
ggtgtatgaa ttgaacacat tgctatattg cagctagtga aatgactgga tcatggttct   5340
cttattttca ggagataagt ttcaagagta aaccaaatgt ttgggcctat ttctcagtaa   5400
aggtagtcct caatattgtt gcactgccac attatttgag ttgtcctaac aattgtgctg   5460
caattgttag ttttcaacta tttgttgttc tgtttggttg actggtaccc tctctttgca   5520
gtctggtgga ggcatccatg aattcgctga ttctcagttc ggtatgtaaa gttaaaagag   5580
taatattgtc tttgctattt atgtttgtcc tcacttttaa aagatattgc cttccattac   5640
aggacatgtt tttgcgtatg gaactactag atcggcagca ataactacca tggctcttgc   5700
actaaaagag gttcaaattc gtggagaaat tcattcaaac gtagactaca cagttgacct   5760
attaaatgta aggactaaat atctgcttat tgaaccttgc ttttttggttc cctaatgcca   5820 ttttagtctg gctactgaag aacttatcca tcatgccatt tctgttatct taaattcagg   5880
cctcagattt tagagaaaat aagattcata ctggttggct ggataccagg atagccatgc   5940
gtgttcaagc tgagaggcct ccatggtata tttcagtcgt tggagggct ttatatgtaa    6000
```

```
gacaaactat gccactcatt agcatttatg tgaagcaaat gcggaaaaca tgatcaatat    6060
gtcgtcttat ttaaatttat ttattttttgt gctgcagaaa acagtaactg ccaacacggc   6120
cactgtttct gattatgttg gttatcttac caagggccag attccaccaa aggtactatt    6180
ctgttttttc aggatatgaa tgctgtttga atgtgaaaac cattgaccat aaatccttgt    6240
ttgcagcata tatcccttgt ctatacgact gttgctttga atatagatgg gaaaaaatat   6300
acagtaagtg tgacattctt aatggggaaa cttaatttgt tgtaaataat caatatcata    6360
ttgactcgtg tatgctgcat catagatcga tactgtgagg agtggacatg gtagctacag    6420
attgcgaatg aatggatcaa cggttgacgc aaatgtacaa atattatgtg atggtgggct    6480
tttaatgcag gtaatatctt cttcctagtt aaagaagata tatcttgttc aaagaattct    6540
gattattgat cttttaatgt tttcagctgg atggaaacag ccatgtaatt tatgctgaag    6600
aagaggccag tggtacacga cttcttattg atggaaagac atgcatgtta caggtaatga    6660
tagccttgtt ctttttagtt ctagtcacgg tgtttgcttg ctatttgttg tatctatttta  6720
atgcattcac taattactat attagttttgc atcatcaagt taaaatggaa cttctttctt   6780
gcagaatgac catgacccat caaagttatt agctgagaca ccatgcaaac ttcttcgttt    6840
cttggttgct gatggtgctc atgttgatgc tgatgtacca tatgcggaag ttgaggttat    6900
gaagatgtgc atgcccctct tatcacccgc ttctggtgtc atacatgttg taatgtctga    6960
gggccaagca atgcaggtac attcctacat tccattcatt gtgctgtgct gacatgaaca    7020
tttcaagtaa atacctgtaa cttgtttatt attctaggct ggtgatctta tagctaggct    7080
ggatcttgat gacccttctg ctgttaagag agctgagccg ttcgaagata cttttccaca    7140
aatgggtctc cctattgctg cttctggcca agttcacaaa ttatgtgctg caagtctgaa    7200
tgcttgtcga atgatccttg cggggtatga gcatgatatt gacaaggtaa acatcatgtc    7260
ctcttgtttt ttcttttgtt tatcatgcat tcttatgttc atcatgtcct ctggcaaatc    7320
tagattccgc tgtcgtttca cacagatttt tctcattctc ataatggtgc caaacataaa    7380
tatgctgcta tattcatcaa tgttttcact cgatttctaa ttttgctttt gagttttaaa    7440
ctttagtaca atccatatct aatctccttt ggcaacagtg aatccattat atatattttt    7500
attaaactgc tttctttttc aggttgtgcc agagttggta tactgcctag acactccgga    7560
gcttcctttc ctgcagtggg aggagcttat gtctgttttta gcaactagac ttccaagaaa   7620
tcttaaaagt gaggtatatt atggttgaca agatagctag tctcatgctc taaggacttg    7680
tacatttcgc cacataggtt aattttccat atcaagttct aatgtacgat ataaaagtag    7740
tactggccta aaacagtatt ggtggttgac tatctttgtt gtgtaagatc aagtatttct    7800
ttttcatgct tagtttgtca atacttcaca tttatcactg acttgtcgag ctaaatgaga    7860
ttttatttga tttctgtgct ccattatttt tgtatatata tatatatatt taactatgac    7920
tatatgttat gcctcaaacg tttcaaactc tttcagttgg agggcaaata tgaggaatac    7980
aaagtaaaat ttgactctgg gataatcaat gatttccctg ccaatatgct acagtgata    8040
attgaggtca gttattcaat ttgttgtgat aatcactgcc ttaactgttc gttcttttaa    8100
caagcggttt tataggaaaa tcttgcatgt ggttctgaga aggagaaggc tacaaatgag    8160
aggcttgttg agcctcttat gagcctactg aagtcatatg agggtgggag agaaagtcat    8220
gctcactttg ttgtcaagtc ccttttttgag gagtatctct atgttgaaga attgttcagt   8280
gatggaattc aggttaactt acctattcgc attaaacaaa tcatcagttg ttttatgata    8340
aagtcaaaat gtttatattt cccattcttc tgtggatcaa atatatcacg gacatgatat    8400
```

```
agtttcctta ggctatataa tggttcttca tcaaataata ttgcaggaaa cagtatagca    8460
aactatttgt atatactcga gatggaaatt gttagaaaca tcattgacta aatctgtcct    8520
ttgttacgct gtttttgtag tctgatgtga ttgagcgtct gcgccttcaa catagtaaag    8580
acctacagaa ggtcgtagac attgtgttgt cccaccaggt aaatttcttc atggtctgat    8640
gacttcactg cgaatggtta ctgaactgtc ttcttgttct gacaatgtga cttttctttg    8700
tagagtgtta gaaataaaac taagctgata ctaaaactca tggagagtct ggtctatcca    8760
aatcctgctg cctacaggga tcaattgatt cgcttttctt cccttaatca caaagcgtat    8820
tacaaggtga ccaggataaa cataaataaa cgtgaatttt tcaatgacct tttcttctga    8880
catctgaatc tgatgaattt cttgcatatt aatacagttg gcacttaaag ctagtgaact    8940
tcttgaacaa acaaaactta gtgagctccg tgcaagaata gcaaggagcc tttcagagct    9000
ggagatgttt actgaggaaa gcaagggtct ctccatgcat aagcgagaaa ttgccattaa    9060
ggagagcatg gaagatttag tcactgctcc actgccagtt gaagatgcgc tcatttcttt    9120
atttgattgt agtgatacaa ctgttcaaca gagagtgatt gagacttata tagctcgatt    9180
ataccaggta tgagaagaaa gacctttga aattatttat attaacatat cctagtaaaa      9240
cagcatgctc atcatttctt aaaaaaagtt tacagcacct gatgtttggt tactgaccgc    9300
atcattaaaa taaagttact tgttgtggag agatgtattt tggaacttgt ggcacatgca    9360
gtaacatgct actgctcgat atgtttgcta acttgacaac aatattttc agcctcatct     9420 tgtaaaggac agtatcaaaa tgaaatggat agaatcgggt gttattgctt tatgggaatt    9480
tcctgaaggg cattttgatg caagaaatgg aggagcggtt cttggtgaca aagatgggg     9540 tgccatggtc attgtcaagt ctcttgaatc actttcaatg gccattagat ttgcactaaa    9600
ggagacatca cactacacta gctctgaggg caatatgatg catattgctt tgttgggtgc    9660
tgataataag atgcatataa ttcaagaaag gtatgttcat atgctatgtt ggtgctgaaa    9720
tagttatata tgtagttagc tggtggagtt ctggtaatta acctatccca ttgttcagtg    9780
gtgatgatgc tgacagaata gccaaacttc ccttgatact aaaggataat gtaaccgatc    9840
tgcatgcctc tggtgtgaaa acaataagtt tcattgttca aagagatgaa gcacggatga    9900
caatgcgtcg taccttcctt tggtctgatg aaaagctttc ttatgaggaa gagccaattc    9960
tccggcatgt ggaacctcct ctttctgcac ttcttgagtt ggtacgtgat atcatcaaaa   10020
tgataatgtt ttggtatggc attgattatc ttctatgctc tttgtattta ttcagcctat   10080
tgtggataca ggacaagttg aaagtgaaag gatacaatga aatgaagtat accccatcac   10140
gggatcgtca atggcatatc tacacactta gaaatactga aaaccccaaa atgttgcacc   10200 gggtatttt ccgaaccctt gtcaggcaac ccagtgtatc caacaagttt tcttcgggcc    10260
agattggtga catggaagtt gggagtgctg aagaacctct gtcatttaca tcaaccagca   10320
tattaagatc tttgatgact gctatagagg aattggagct tcacgcaatt agaactggcc   10380
attcacacat gtatttgcat gtattgaaag aacaaaagct tcttgatctt gttccagttt   10440
cagggtaagt gcgcatattt ctttttggga acatatgctt gcttatgagg ttggtcttct   10500
caatgatctt cttatcttac tcaggaatac agttttggat gttggtcaag atgaagctac   10560
tgcatattca cttttaaaag aaatggctat gaagatacat gaacttgttg gtgcaagaat   10620
gcaccatctt tctgtatgcc aatgggaagt gaaacttaag ttggactgcg atggtcctgc   10680
cagtggtacc tggaggattg taacaaccaa tgttactagt cacacttgca ctgtggatgt   10740
```

```
aagtttaatc ctctagcatt ttgttttctt tggaaaagca tgtgatttta agccggctgg    10800
tcctcatacc cagacctagt gatctttata tagtgtagac attttctaa ctgcttttaa     10860 ttgtttaga tctaccgtga gatggaagat aaagaatcac ggaagttagt ataccatccc     10920
gccactccgg cggctggtcc tctgcatggt gtggcactga ataatccata tcagcctttg    10980
agtgtcattg atctcaaacg ctgttctgct aggaataata gaactacata ctgctatgat    11040
tttccactgg tgagttgact gctcccttat attcaatgca ttaccatagc aaattcatat    11100
tcgttcatgt tgtcaaaata agccgatgaa aattcaaaac tgtaggcatt tgaaactgca    11160
gtgaggaagt catggtcctc tagtacctct ggtgcttcta aaggtgttga aaatgcccaa    11220
tgttatgtta aagctacaga gttggtattt gcggacaaac atgggtcatg gggcactcct    11280
ttagttcaaa tggaccggcc tgctgggctc aatgacattg gtatggtagc ttggaccttg    11340
aagatgtcca ctcctgaatt tcctagtggt agggagatta ttgttgttgc aaatgatatt    11400
acgttcagag ctggatcatt tggcccaagg gaagatgcat tttttgaagc tgttaccaac    11460
ctagcctgtg agaagaaact tcctcttatt tatttggcag caaattctgg tgctcgaatt    11520
ggcatagcag atgaagtgaa atcttgcttc cgtgttgggt ggtctgatga tggcagccct    11580
gaacgtgggt ttcagtacat ttatctaagc gaagaagact atgctcgtat tggcacttct    11640
gtcatagcac ataagatgca gctagacagt ggtgaaatta ggtgggttat tgattctgtt    11700
gtgggcaagg aagatggact tggtgtggag aatgtacatg gaagtgctgc tattgccagt    11760
gcttattcta gggcatataa ggagacattt acacttacat ttgtgactgg aagaactgtt    11820
ggaataggag cttatcttgc tcgacttggc atccggtgca tacagcgtct tgaccagcct    11880
attattctta caggctattc tgcactgaac aagcttcttg ggcgggaagt gtacagctcc    11940
cacatgcagt tgggtggtcc caaaatcatg gcaactaatg tgttgtcca tcttactgtt     12000 tcagatgacc ttgaaggcgt ttctaatata ttgaggtggc tcagttatgt tcctgcctac    12060
attggtggac cacttccagt aacaacaccg ttggacccac cggacagacc tgttgcatac    12120
attcctgaga actcgtgtga tcctcgagcg gctatccgtg gtgttgatga cagccaaggg    12180 aaaatggttag gtggtatgtt tgataaagac agctttgtgg aaacatttga aggttgggct    12240
aagacagtgg ttactggcag agcaaagctt ggtggaattc cagtgggtgt gatagctgtg    12300
gagactcaga ccatgatgca aactatccct gctgaccctg gtcagcttga ttcccgtgag    12360
caatctgttc ctcgtgctgg acaagtgtgg tttccagatt ctgcaaccaa gactgcgcag    12420
gcattgctgg acttcaaccg tgaaggatta cctctgttca tcctcgctaa ctggagaggc    12480
ttctctggtg gacaaagaga tcttttttgaa ggaattcttc aggctggctc gactattgtt    12540
gagaacctta ggacatacaa tcagcctgcc tttgtctaca ttcccatggc tgcagagcta    12600
cgaggagggg cttgggttgt ggttgatagc aagataaacc cagaccgcat tgagcgctat    12660
gctgagagga ctgcaaaagg caatgttctg gaaccgcaag ggttaattga gatcaagttc    12720
aggtcagagg aactccagga ttgcatgagt cggcttgacc caacattaat tgatctgaaa    12780
gcaaaactcg aagtagcaaa taaaaatgga agtgctgaca caaaatcgct tcaagaaaat    12840
atagaagctc gaacaaaaca gttgatgcct ctatatactc agattgcgat acggtttgct    12900
gaattgcatg atacatccct cagaatggct gcgaaaggtg tgattaagaa agttgtggac    12960
tgggaagaat cacgatcttt cttctataag agattacgga ggaggatctc tgaggatgtt    13020
cttgcaaaag aaattagagc tgtagcaggt gagcagtttt cccaccaacc agcaatcgag    13080
ctgatcaaga aatggtattc agcttcacat gcagctgaat gggatgatga cgatgctttt    13140
```

```
gttgcttgga tggataaccc tgaaaactac aaggattata ttcaatatct taaggctcaa    13200
agagtatccc aatccctctc aagtctttca gattccagct cagatttgca agccctgcca    13260
cagggtcttt ccatgttact agataaggta attagcttac tgatgcttat ataaattctt    13320
tttcattaca tatggctgga gaactatcta atcaaataat gattataatt ccaatcgttc    13380
tttttatgcc attatgatct tctgaaattt ccttctttgg acacttattc agatggatcc    13440
ctctagaaga gctcaacttg ttgaagaaat caggaaggtc cttggttgaa tcatatgatg    13500
ccaaaactat tattggaggc acaaatagct tgtggaccct gtcggattgt tggtgagtgt    13560
atattggatt tgttagttct gccagatgaa agtgcaagtc tgatgattca tgataccgtc    13620
agttggcaag aacaccggtt aacctgagtg cttgtttaca aatggtcctt tatgacaatc    13680
gttgtttcgc gctagttccg tgatctacta tcatctgtta gacgctgtaa ttagtgagtc    13740
tccgcggatc cacagtatac ggttgagctg ttgattcaat tttggacacg aataatatga    13800
ttttgtaggc ataaatgcgt ctgtatgtga aataaattgt ctgttgagtt aacacacaag    13860
atgacaatat gtttgtgctc tactgctatt gtccatgaat actgattgcg gaatcaacca    13920
catgcattat a                                                        13931

<210> SEQ ID NO 8
<211> LENGTH: 20
<212> TYPE: DNA
<213> ORGANISM: Artificial Sequence
<220> FEATURE:
<223> OTHER INFORMATION: guide-PAM sequence of sgRNA No. A-ACC1879

<400> SEQUENCE: 8
gagaatatac atggaagtgc                                                20

<210> SEQ ID NO 9
<211> LENGTH: 20
<212> TYPE: DNA
<213> ORGANISM: Artificial Sequence
<220> FEATURE:
<223> OTHER INFORMATION: guide-PAM sequence for sgRNA No. A-ACC2186

<400> SEQUENCE: 9
atagcactca atgcggtctg                                                20
```